(12) United States Patent
Wood et al.

(10) Patent No.: US 8,147,836 B2
(45) Date of Patent: Apr. 3, 2012

(54) COMPOSITIONS AND METHODS FOR TREATING OSTEOLYTIC DISORDERS COMPRISING MMP-14 BINDING PROTEINS

(75) Inventors: Clive R. Wood, Boston, MA (US);
Daniel T. Dransfield, Hanson, MA (US);
Laetitia Devy, Somerville, MA (US)

(73) Assignee: Dyax Corp., Cambridge, MA (US)

( * ) Notice: Subject to any disclaimer, the term of this patent is extended or adjusted under 35 U.S.C. 154(b) by 205 days.

(21) Appl. No.: 12/337,140

(22) Filed: Dec. 17, 2008

(65) Prior Publication Data

US 2009/0186031 A1     Jul. 23, 2009

Related U.S. Application Data

(60) Provisional application No. 61/008,153, filed on Dec. 17, 2007, provisional application No. 61/025,032, filed on Jan. 31, 2008, provisional application No. 61/107,510, filed on Oct. 22, 2008.

(51) Int. Cl.
*A61K 39/395* (2006.01)

(52) U.S. Cl. ............... 424/146.1; 424/130.1; 424/133.1; 424/138.1; 530/350; 530/387.1; 530/387.3; 530/387.7; 530/388.26

(58) Field of Classification Search ............... 424/130.1, 424/133.1, 138.1, 146.1; 530/350, 387.1, 530/387.3, 387.7, 388.26
See application file for complete search history.

(56) References Cited

U.S. PATENT DOCUMENTS

| | | |
|---|---|---|
| 2006/0275294 A1 | 12/2006 | Omoigui |
| 2007/0172482 A1 | 7/2007 | Sagi |
| 2007/0217997 A1 | 9/2007 | Devy et al. |
| 2009/0203060 A1 | 8/2009 | Wood et al. |
| 2009/0297449 A1 | 12/2009 | Devy |
| 2009/0311245 A1 | 12/2009 | Devy et al. |

FOREIGN PATENT DOCUMENTS

| | | |
|---|---|---|
| EP | 1981538 | 10/2008 |
| WO | 2007079218 | 7/2007 |
| WO | 2009079581 | 6/2009 |
| WO | 2009111450 | 9/2009 |
| WO | 2009111508 | 9/2009 |
| WO | 2010048432 | 4/2010 |

OTHER PUBLICATIONS

Stancoviski et al. (Proceedings of the National Academy of Science USA. 1991; 88: 8691-8695).*
Jiang et al. (J. Biol. Chem. Feb. 11, 2005; 280 (6): 4656-4662).*
Riemer et al. (Mol. Immunol. 2005; 42: 1121-1124).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Paquette et al. (Br. J. Cancer. Dec. 3, 2007; 97 (11): 1505-1512).*
Rosen (Oncology. May 2004; 18 (5 Suppl 3): 26-32).*
Itoh (IUBMB Life; Oct. 2006; 58 (10): 589-596).*
Jiang et al. (Int. J. Mol. Med. 2006; 17: 583-590.*
Lee et al., "A matrix metalloproteinase inhibitor, batimastat, retards the development of osteolytic bone metastase by MDA-MB-231 human breast cancer cells in Balb C nu/nu mice," Eur. J. Cancer, Jan. 2001, 37(1):106-13.
Sato et al., "Identification of the membrane-type matrix metalloproteinase MT1-MMP in osteoclasts," J. Cell Sci. (1997) vol. 110:589-596.
Sanchez-Sweatman et al., "Human Metastatic Prostate PC3 Cell Lines Degrade Bone Using Matrix Metalloproteinases," Invasion Metastasis (1998/99) vol. 18:297-305.
Winding et al., "Synthetic Matrix Metalloproteinase Inhibitors Inhibit Growth of Established Breast Cancer Osteolytic Lesions and Prolong Survival in Mice," Clinical Cancer Research, Jun. 2002, vol. 8:1932-1939.
Galvez, B.G. et al., "Membrane Type 1-Matrix Metalloproteinase Is Activated During Migration of Human Endothelial Cells and Modulates Endothelial Motility and Matrix Remodeling", J. Biol. Chem., 276(40):37491-37500 (2001).

* cited by examiner

*Primary Examiner* — Stephen Rawlings
(74) *Attorney, Agent, or Firm* — Lando & Anastasi LLP

(57) ABSTRACT

Provided are methods and compositions for using MMP-14 or MMP-9 binding proteins alone or in combination with other therapeutic agents to treat osteolytic disorders such as osteotropic cancer and osteoporosis.

16 Claims, 8 Drawing Sheets

FIGURE 1

```
  1 M0031-C02  SC=SC-001  Round=SC-001-SR-003
HC
       1     5      0          5     0           5        0             5        0           5        0
   1 EVQLLESGGG LVQPGGSLRL SCAASGFTFS PYPMGWVRQA PGKGLEWVSS 5     5      6          6     7           7      8 8      8 8         8 8      9 9
       1     a      5          0     5           0      0  2abc3 5           7 9      2 5
  51 IVSSGGLTLY ADSVKGRFTI SRDNSKNTLY LQMNSLRAED TAVYYCARGG 1         1 1         1
       9     0             0 0       1
       7     2abcd  efghi3 5          0
 101 RLYDILTGQG APFDYWGQGT LVTVSS LC
   1 QDIQMTQSPL SLPVTPGEPA SISCRSSQSL LHSNGYYYLD WYLQKPGQSP
  51 QLLIYLGSYR ASGVPDRFSG SGSGTDFTLK ISSVEAEDVG VYYCMQALQT
 101 PLTFGGGTRV DIK ------
  2 M0031-F01  SC=SC-001  Round=SC-001-SR-003
HC
   1 EVQLLESGGG LVQPGGSLRL SCAASGFTFS TYEMHWVRQA PGKGLEWVSS
  51 IYSSGGWTGY ADSVKGRFTI SRDNSKNTLY LQMNSLRAED TAVYYCARSQ
 101 QYYDFSSRYY GMDVWGQGTT VTVSS
LC
   1 QSELTQPPSV SGTPGQRVTI SCSGTSANIG RNAVHWYQQL PGTAPKLLIH
  51 SNNRRPSGVP DRFSGSKSGT SASLAISGLQ SEDEADYYCA AWENSLNAFY
 101 VFGTGTKVTV L ------
  3 M0033-H07  SC=SC-001  Round=SC-001-SR-003
HC
   1 EVQLLESGGG LVQPGGSLRL SCAASGFTFS VYGMVWVRQA PGKGLEWVSV
  51 ISSSGGSTWY ADSVKGRFTI SRDNSKNTLY LQMNSLRAED TALYYCARPF
 101 SRRYGVFDYW GQGTLVTVSS
LC
   1 QDIQMTQSPS SLSASVGDRV TITCRASQGI RNFLAWYQQK PGKVPKLLVF
  51 GASALQSGVP SRFSGSGSGT DFTLTISGLQ PEDVATYYCQ KYNGVPLTFG
 101 GGTKVEIK ------
  4 M0037-C09  SC=SC-001  Round=SC-001-SR-003
HC
   1 EVQLLESGGG LVQPGGSLRL SCAASGFTFS HYEMFWVRQA PGKGLEWVSS
  51 ISPSGGQTHY ADSVKGRFTI SRDNSKNTLY LQMNSLRAED TAVYYCATDR
 101 TYYDFWSGYG PLWYWGQGTL VTVSS
LC
   1 QDIQMTQSPL SLPVTLGESA SVSCRSSQSL LHENGHNYLD WYLQKPGQSP
  51 QLLIYLGSNR ASGVPDRFSG SGSGTDFTLK ISRVEAEDVG VYYCMQSLKT
 101 PPTFGPGTKV EIK
```

FIGURE 1 (cont.)

```
   5 M0037-D01 SC=SC-001 Round=SC-001-SR-003
HC
    1 EVQLLESGGG LVQPGGSLRL SCAASGFTFS MYMMIWVRQA PGKGLEWVSS
   51 IYPSGGNTMY ADSVKGRFTI SRDNSKNTLY LQMNSLRAED TAVYYCATGV
  101 LRYFDWDAGS GMDVWGQGTT VTVSS
LC
    1 QDIQMTQSPS SLSASVGDRV TITCRASQGI RNDLGWYQQK PGKAPKRLIY
   51 VASSLQSGVP SRFSGSGSGT EFTLTISSLQ PEDFATYYCL QHNSYPWTFG
  101 QGTKVEIK 6 M0038-E06 SC=SC-001 Round=SC-001-SR-003
HC
    1 EVQLLESGGG LVQPGGSLRL SCAASGFTFS PYVMHWVRQA PGKGLEWVSS
   51 ISPSGGWTYY ADSVKGRFTI SRDNSKNTLY LQMNSLRAED MAVYYCARGT
  101 GAYGMDVWGQ GTTVTVSS
LC
    1 QDIQMTQSPG TLSLSPGDRA TLSCGASQLV VSNYIAWYQQ KPGQAPRLLM
   51 YAGSIRATGI PDRFSGSGSG TDFTLTISRL EPEDFAIYYC QQRSNWPWTF
  101 GQGTKVEIK 7 M0038-F01 SC=SC-001 Round=SC-001-SR-003
HC
    1 EVQLLESGGG LVQPGGSLRL SCAASGFTFS LYSMNWVRQA PGKGLEWVSS
   51 IYSSGGSTLY ADSVKGRFTI SRDNSKNTLY LQMNSLRAED TAVYYCARGR
  101 AFDIWGQGTM VTVSS
LC
    1 QDIQMTQSPS SLSAFVGDKV TITCRASQSV GTYLNWYQQK AGKAPELLIY
   51 ATSNLRSGVP SRFSGSGSGT DFTLTINTLQ PEDFATYYCQ QSYSIPRFTF
  101 GPGTKVDIK 8 M0038-F08 SC=SC-001 Round=SC-001-SR-003
HC
    1 EVQLLESGGG LVQPGGSLRL SCAASGFTFS RYKMWWVRQA PGKGLEWVSG
   51 IRPSGGLTRY ADSVKGRFTI SRDNSKNTLY LQMNSLRAED TAVYYCARRG
  101 DYVGGFDYWG QGTLVTVSS
LC
    1 QDIQMTQSPG TLSLSPGERA TLSCRASQSV SSSYLAWYQQ KPGQAPRLLI
   51 YGASSRATGI PDRFSGSGSG TDFTLTISRL EPEDFAVYYC QHYGGSQAFG
  101 GGTKVEIK 9 M0039-H08 SC=SC-001 Round=SC-001-SR-003
HC
    1 EVQLLESGGG LVQPGGSLRL SCAASGFTFS AYNMGWVRQA PGKGLEWVSS
   51 ISSSGGYTGY ADSVKGRFTI SRDNSKNTLY LQMNSLRAED TAVYYCARDL
  101 YRGFDYWGQG TLVTVSS
LC
    1 QDIQMTQSPA TLSVSPGERA TLSCRASESV KNNLAWYQQK PGQAPRLLIY
   51 GVSTRAPGIP ARFSGSGSGT DFTLTISSLE PEDFAVYYCQ QRSNWPPVTF
  101 GQGTRLEIK
```

```
 10 M0040-A06  SC=SC-001  Round=SC-001-SR-003
HC
    1 EVQLLESGGG LVQPGGSLRL SCAASGFTFS YYGMYWVRQA PGKGLEWVSS
   51 ISSSGGYTDY ADSVKGRFTI SRDNSKNTLY LQMNSLRAED TAVYYCARRI
  101 KYYDIEGEGA FDIWGQGTMV TVSS
LC
    1 QDIVMTQTPP SLPVNPGEPA SISCRSSQSL LHRNGYNYLD WYLQKPGQSP
   51 QLLIHLGSYR ASGVPDRFSG SGSGTDFTLK ISRVEAEDVG VYYCMQPLQT
  101 PFTFGPGTKV DIK
```

---

```
 11 M0040-A11  SC=SC-001  Round=SC-001-SR-003
HC
    1 EVQLLESGGG LVQPGGSLRL SCAASGFTFS HYVMFWVRQA PGKGLEWVSR
   51 IVPSGGATMY ADSVKGRFTI SRDNSKNTLY LQMNSLRAED TAVYYCARDR
  101 PLYDSSGYVD YWGQGTLVTV SS
LC
    1 QSALTQPPSA SGSPGQSVTI SCTGTSSDVG AYNYVSWYQQ HPDKAPKLII
   51 YNVNERPSGV PDRFSGSKSG NTASLTVSGL QAEDEADYYC TSYAGSNKIG
  101 VSGTGTKVTV L
```

---

```
 12 M0043-G02  SC=SC-001  Round=SC-001-SR-003
HC
    1 EVQLLESGGG LVQPGGSLRL SCAASGFTFS WYPMFWVRQA PGKGLEWVSG
   51 IYSSGGPTDY ADSVKGRFTI SRDNSKNTLY LQMNSLRAED TAVYYCAKDT
  101 LGRYYDFWSG YSYGMDVWGQ GTTVTVSS
LC
    1 QDIQMTQSPG TLSLSPGERA TLSCRASQSV SSSYLAWYQQ KPGQAPRLLI
   51 YGASSRATGI PDRFSGSGSG TDFTLTISRL EPEDFAVYYC QSGVTFGGGT
  101 KVEIK
```

FIGURE 3

| Initial Name | LV-CDR1 | LV-CDR2 | LV-CDR3 | HV-CDR1 | HV-CDR2 | HV-CDR3 |
|---|---|---|---|---|---|---|
| 539A-M0072-H10 | RASQSVSSYLA | DASNRAT | QQRGNWPIT | PYRMS | SIGSSGGQTSYADSVKG | EPPGYYFDS |
| 539A-M0072-G08 | RASQSVSSYLA | DASNRAT | QQRSNWPIT | AYGMV | VIRSSGGPTSYADSVKG | AGGGTYLDY |
| 539A-M0071-E10 | RASQSVSSYLA | DASNRAT | QQRSNWPLT | HYRMY | YIGSSGGMTSYADSVKG | |
| 539A-M0076-D07 | RASQSVSTFLA | DASNRAT | QQYASPPRT | GYYMS | | DSGQTFYYAFDI |
| 539A-M0081-G03 | RTSHNVANFLA | DAYNRAT | QQRANWPLS | RYPME | YISSSGGWTSYADSVKG | DGLELFGGWLES |
| 539A-M0075-D06 | RTSQSVSDSLA | DASNRAT | QQRGSWPIT | NYRMM | YIGSSGGMTSYADSVKG | ETNWNDLGRYFDY |
| 539A-M0071-D03 | RASQSISSSFLA | GASSRAT | QQTYSTPLT | KYSMV | VISPSGGYTGYADSVKG | MRVPAAIGGWLDP |
| 539A-M0072-H07 | RASQSVSSNLA | GASTRAT | HQYNDWPLT | PYKMY | YIGSSGGMTSYADSVKG | RGYSSGPLRY |
| 539A-M0081-D05 | RASESISRNLA | | | MYRMS | YIGSSGCPTAYADSVKG | ECDARVPAAICY |
| 539A-M0071-E02 | KSSQNVLLSSNSKNYLA | WASTRES | QQYYSIPWS | NYRMS | SIGSSGGQTMYADSVKG | SHPVSGGVFDF |
| 539A-M0075-B09 | KSSQSILYSSNNRNYLA | WASTRES | QFYYTAPYT | GYSMH | SIWPSGGYTRYADSVKG | GNDSDSFAYRF |
| 539A-M0075-G09 | KSSQSVLYSSNNKNYLA | WASTRES | QQYYSTPLT | EYRMT | YIGSSGGMTTYADSVKG | GSGSGYDS |
| 539A-M0074-D05 | KSSQSVLYSSNNKNYLA | WASTRES | QQSYSTPLT | AYRMH | YIGSSGGMTTYADSVKG | STVTTLDY |
| 539A-M0073-G12 | RASQSVSSNLA | GASTRAT | QQYNKWPQT | IYRMH | YIGSSGGNTSYADSVKG | EWVGSSAALDY |
| 539A-M0074-G03 | RASQTISSYYLA | GASSRAA | QQYGVSPPYS | YYNMV | VISPSGGWTPYADSVKG | EVGGSGWLGDAFDI |
| 539A-M0075-F03 | RASQSVGSDYLA | AASTRAT | QQRSSWPPT | KYYMV | YISPSGGTYYADSVKG | NYYDSSGTRGAFDI |
| 539A-M0071-G11 | RASETVRYGQVA | DASKRAT | QQRSNWPLT | LYRMN | YIGSSGGATAYADSVKG | SMRGGHLDS |
| 539A-M0075-D11 | RASHSVGGYLA | DAFNRAT | QQRSEWPWT | RYKMS | YIGSSGGMTSYADSVKG | DLTATGYFDY |
| 539A-M0072-F05 | RASQSISSELA | GASNRAT | QQRSNWPPT | AYRMQ | YIGSSGGQTSYADSVKG | DPVGAKYYGMDV |
| 539A-M0073-C11 | RASQSVSSSYLA | DASNRAT | QQRSNWPIT | NYRMH | WISSSGGPTSYADSVKG | GCSYRHNNVFDI |
| 539A-M0074-E11 | RASQSVSSSYLA | GASSR | | QYRMF | YIGSSGGMTSYADSVKG | SMGYGDAFDI |

FIGURE 3 (cont'd)

| | | | | | | |
|---|---|---|---|---|---|---|
| 539A-M0073-G10 | RASQTVSRNYLA | DASKRAT | QQRSNWPPT | | | |
| 539A-M0078-G07 | RASQSVSSDLA | GVSTKAT | QQYHNWPPLT | SYTME | WISPSGGYTFYADSVKG | GYSYGSIDL |
| 539A-M0071-A06 | RSSQSLVSSNGNTYLN | YKVSNRDS | MQGTHWPYT | MYRMM | YIGSSGGMTSYADSVKG | DSVFRGERDAFDI |
| 539A-M0071-D11 | RASQNIGKFLA | GASTLQL | QKYDSALWT | GYGMW | SISPSGGWTFYADSVKG | VKVRHGGGFDY |
| 539A-M0071-A04 | RSSESLLQSSGHTRFD | LGFNRAS | MHALFPPYT | YYQMM | YISPSGGMTLYADSVKG | GWGYFDY |
| 539A-M0084-E03 | RASQSIDTYLN | AASKLED | QQSYSSPCIT | HYDMS | SIWPSGGVTWYADSVKG | GGYNNYYYALDV |
| 539A-M0072-C12 | RASQDIRSSIA | AASSTQS | QQANSFPPT | SYRMQ | YIGSSGGMTSYADSVKG | GSWRGGSQYFDY |
| 539A-M0081-E01 | RASQSISSYLN | AASSLQS | QQSYSTPRT | HYVMS | SIGSSGGDTHYADSVKG | VWISGSYLDAFDI |
| 539A-M0082-F03 | RASQSTSNSLS | AASRLQS | QQSWRTPLT | QYWMT | GIGPSGGPTTYADSVKG | ESTTVTTNFDY |
| 539A-M0076-D03 | RASQGIRNDLD | SASNLQS | LQHNSFPLT | LYRMN | YIGSSGGATAYADSVKG | GAWYLDS |
| 539A-M0075-G12 | RASQGIRNDLG | AASSLQS | QQTITFPLT | SYRMM | WISSSGGSTGYADSVKG | TTVTRVGSFYFDL |
| 539A-M0072-C04 | RASQGIRNDIG | AASSTQS | QQLNSYPPT | PYRMH | RIGSSGGATSYADSVKG | DGIAVAGIAFDI |
| 539A-M0075-A07 | RASQGISSALA | DASSLES | QQFHTYPFT | TYRMV | YIGSSGGQTAYADSVKG | ENRAIGTFDY |
| 539A-M0076-H03 | RASQGVSNYLA | AASTLQS | QKYNSAPYT | NYSMG | GIYSSGGYTQYADSVKG | GLYVWDSGWYSAFDI |
| 539A-M0085-H01 | RASQNIAGLLA | KASTLES | QQYSFNSGT | KYHMH | SISPSGGVTSYADSVKG | |
| 539A-M0085-G04 | RASQRISIYLN | AAYNLQS | QQSDSSPZT | | | |
| 539A-M0071-E12 | RASQSISSDLN | AASSLQS | QQSYSTPVT | DYRMF | SISSSGGFTNYADSVKG | DQGGTVVVVATADY |
| 539A-M0072-H08 | RASQSISSTITYLN | AASNRAT | QQRSNWPPT | DYKMW | SIRSSGGPIGYADSVKG | ETNQMGMDV |
| 539A-M0071-F10 | RASQSTSSWIA | KASSLES | QQYNSYPWT | KYKMF | SIGSSGGATSYADSVKG | GGFWSGYYGY |
| 539A-M0083-A05 | RASQSISSYLN | AASSLQS | QQSYSTPRT | HYPMS | YIYSSGGDTEYADSVKG | YGSGGWMTYGLDV |
| 539A-M0082-G08 | RASQSISSYIN | AASSLQS | QQSYSTPRT | MYYMY | SIRSSGGETQYADSVKG | VWISGSYLDAFDI |
| 539A-M0072-F02 | RASQSISSYLN | AASSLQS | QQSYSTPRT | HYVMS | SIGSSGGDTHYADSVKG | VWISGSYLDAFDI |
| 539A-M0071- | RASQSISSYLN | GASSLQS | QQSYSIPRT | WYKMA | VIYPSGGPTFYADSVKG | GQRGYNYDRSSYSYEYYYGMDV |

FIGURE 3 (cont'd)

| ID | | | | | | |
|---|---|---|---|---|---|---|
| F09 539A-M0082-G09 | RATQYISNYVN | AASSLQS | QQANSFPPT | AYSMH | RLGSSGGPTSYADSVKG | RSSYGRGFDY |
| 539A-M0071-A05 | RASQGISNYLA | AASNLQS | QQYKTYPFT | PYRMH | YIGSSGGPTAYADSVKG | ARAGTFFDS |
| 539A-M0076-E11 | RASQGISRWLA | DASNRAT | QQRSNWPPRLT | FYHMS | SIGPSGGWTNYADSVKG | DGGLEGMDV |
| 539A-M0081-B03 | RASQGISSWLA | AASSLQS | QQANSFPYLT | TYMMM | SIWSSGGSTFYADSVKG | GVVVPALDY |
| 539A-M0071-H10 | RASQGISSWLA | AASTLQS | QPTYSTSWT | TYSMV | RIGSSGGDTFYADSVKG | DRADTVVTAGGDYYYYYGMDV |
| 539A-M0075-D12 | RASQGISSWLA | GASSLES | QQANSFPPT | DYRMT | WIGSSGGQTSYADSVKG | GTPRVASYFDY |
| 539A-M0072-B02 | RASQSTSSWLA | KASSLFS | QQYNSYPWT | NYKMH | STGSSGGMTSYADSVKG | RDWQFLAGDAFDF |
| 539A-M0071-E03 | RASQGISSWLA | YATSSLQS | QQSKSFPPT | RYRMN | YIGSSGGNTAYADSVKG | RRIGVGAKGGGTFDI |
| 539A-M0082-G01 | QASQDIGNYLN | DTSILKK | QQANSFzLT | LYNMW | WISSSGGNTKYADSVKG | GAPYYLQL |
| 539A-M0074-D09 | | DVSNRAT | QQRSNWPLT | MYRMI | WIGSSGGQTSYADSVKG | GLWCDN |
| 539A-M0071-H05 | SGDKLGDKYAS | QDRKRPS | QAWDSNTVV | HYDMW | RIVPSGGLTTYADSVKG | HSFWSGYYGAFDI |
| 539A-M0075-H05 | TGTSSDVGYYNYVS | DVSARPS | CSYAGSYTYV | MYYMQ | SIRSSGGFTSYADSVKG | GLRLDM |
| 539A-M0113-A08 | | | | RYHMF | YTSPSGGVTMYADSVKG | GAPSGTFFDY |
| 539A-M0116-E02 | RASQSVSSYLA | DASTRAT | HQRSNWPQT | RYRML | | RAKKGAFDI |
| 539A-M0131-F06 | RASQSVTNNLA | GASTRAT | QQYNNWPRT | EYMMW | RIGSSGGITSYADSVKG | QHYGDYDY |
| 539A-M0131-B05 | RASQSISSYLN | AASSLQS | | IYNMY | YIYSSGGPTAYADSVKG | RGYYDSSGYWGAFDI |
| 539A-M0133-H11 | RASQSVSSSYLA | GASSRAT | QQYGSSHT | HYLMV | GIVSSGGYTAYADSVKG | GAYDSSGIVFDY |
| 539A-M0113-F03 | RASQSVSINLA | GASTRAT | QQYDNWWT | QYVMS | SIVPSGGYTSYADSVKG | SLRFGFGELPGY |
| 539A-M0114-D01 | RSSQSLLHNNGYNYLD | LGSYRAS | MQALQTPIT | EYAML | YISPSGGSTFYADSVKG | GGTKKSI |
| 539A-M0133-A06 | RSSQSLLHRNGQNYLD | LGSNRAS | MQGLQTPRT | MYEMQ | GISPSGGKTGYADSVKG | SRYSGSYFPPGGSHFDY |
| 539A-M0133-H10 | RASQSISSYLN | AASSLQS | QQSYSTPWT | PYAMV | WISPSGGDTDYADSVKG | CFGWFDDAFDI |
| 539A-M0133-B09 | WASQDVSSFFA | SASTLQG | QQYNTFPWT | MYNMI | VIRSSGGPTSYADSVKG | VVGAAGILQPFDY |
| 539A-M0114 | RASQSIDTYLN | AASKLED | QQSYSSPCIT | RYGMG | VIWPSGGSTYYADSVKG | VRDYYDSSGHYFSDAFDI |

FIGURE 3 (cont'd)

| | | | | | | |
|---|---|---|---|---|---|---|
| A05 539A-M0131-A08 | QASQDISNYLN | DASSLQS | EQANSFPLT | SYDMN | GIGSSGGLTEYADSIKG | DRGYNNYYYYGMDV |
| 539A-M0133-C11 | RASHCARVDLA | CTSSLQR | LQENSYPLT | MYDMS | YISSSCCFTMYADSVKG | DLNSSSPPCSNDAFDI |
| 539A-M0113-H02 | RASQDISNYLA | AASTLQS | QQSYSAPFT | KYIMN | SISPSGGMTAYADSVKG | MMKETEYDTNWYFAFDY |
| 539A-M0114-F01 | RASQGISTFLA | GASTLQS | QKYNSAPFT | KYQMQ | YIVPSGGLTDYADSVKG | GGRGGYTHFDF |
| 539A-M0132-C03 | RASQSISRYLN | AAASLQS | QQSYSTPPLT | GYGMA | GIYSSGGWTAYADSVKG | DLSGSYSD |
| 539A-M0132-C05 | RASQGISNWLA | FGASNLQS | QQADSFPIT | HYSMV | YIWPSGGTTKYADSVKG | GWFTDAFDI |
| 539A-M0114-E08 | RANQRISTYLA | AGSTLQS | QQTITFPLT | SYTMS | SISSSGGFTVYADSAKG | EGGTFPVYYFDN |
| 539A-M0113-G09 | RASQGISSWLA | AASSLQS | QQANSFPLT | | YIGPSGGYTAYADSVKG | DPSYYDSSGYDAFDI |
| 539A-M0133-B06 | RASQCISSWLA | AASSLQS | QQANSFPIT | PYDMH | SIGPSCGVTFYADSVKG | EIPCDSCYDDY |
| 539A-M0133-C02 | RASQGITTWLA | SASTLHS | QQANNFPYT | AYSMG | VIGSSGGYTNYADSVKG | RPHSTGTDAFDI |
| 539A-M0113-E04 | RASQSIGSWLA | KASSLEG | QQSYSTPLT | GYIMG | SISPSGGITMYADSVKG | DNWNDGAFDI |
| 539A-M0133-D09 | RASQYIRNDLG | AASTLQS | LQDYSYPQT | YYPMG | SIYSSGGKTQYADSVKG | GRYGDFDY |
| 539A-M0114-H04 | RSSQSLVHSDGNTYLN | KVSNRDS | MQGTHWPWT | NYTMF | VISPSGGNTAYADSVKG | FAGKN |
| 539A-M0132-F12 | SGSSSNIGSNTVY | RNNQRPL | AAWDDSLSTWV | VYDMM | GISPSGGYTKYADSVKG | HRLRFLEDAFDI |

COMPOSITIONS AND METHODS FOR TREATING OSTEOLYTIC DISORDERS COMPRISING MMP-14 BINDING PROTEINS

CROSS REFERENCE TO RELATED APPLICATIONS

This application claims priority to U.S. Application Ser. No. 61/008,153, filed on Dec. 17, 2007, U.S. Application Ser. No. 61/025,032, filed on Jan. 31, 2008, and U.S. Application Ser. No. 61/107,510, filed on Oct. 22, 2008. The disclosures of the prior applications are considered part of (and are incorporated by reference in) the disclosure of this application.

BACKGROUND

Osteoclasts, which mediate bone resorption, are involved in normal and abnormal bone remodeling processes, including osteolytic disorders. Osteoclasts are multinucleated cells differentiating from haemopoietic cells. It is generally accepted that osteoclasts are formed by the fusion of mononuclear precursors derived from haemopoietic stem cells in the bone marrow, rather than incomplete cell division. The differentiation of osteoclast precursors into mature multinucleated osteoclasts requires different factors including hormonal and local stimuli and living bone and bone cells have been shown to play a critical role in osteoclast development. Osteoblastic or bone marrow stromal cells are also required for osteoclast differentiation. Osteoclasts are responsible for dissolving both the mineral and organic bone matrix. Osteoclasts represent terminally differentiated cells expressing a unique polarized morphology with specialized membrane areas and several membrane and cytoplasmic markers.

Several molecular mechanisms bring about cancer cells to metastasize to bone, and osteotropic cancer cells are believed to acquire bone cell-like properties which improve homing, adhesion, proliferation and survival in the bone microenvironment. Signaling pathways involved in tumor growth and development of osteolytic lesions include RANK, RANKL, osteoprotegerin (OPG), IGF and the membrane type (MT)-matrix metalloproteinases (MMPs). The initial phase of bone degradation consists of removal of the unmineralized type I collagenous layer followed by degradation of the mineralized matrix, which also comprises type I collagen. Tumor expansion in bone requires the removal of this matrix that is particularly abundant and resistant to degradation. The assistance of osteoclasts appears to be mandatory because osteoclasts are the primary cells involved in bone matrix solubilization. The capacity of osteoclasts to degrade bone resides in their ability to secrete protons, cathepsin K and MMPs. A generalized increase in MMPs levels within the bone environment when cancer cells are present is due, in part, to production of MMPs by the cancer cells themselves.

Since osteoclasts play a major role in osteolytic bone metastases and other osteolytic diseases, there is a need in the art for new agents and methods for preventing osteoclast stimulation and function. Several therapeutic strategies targeting osteolytic disease are currently being used or under development, where efforts have mainly focused on the development of drugs to block bone resorption through inhibiting the formation or activity of osteoclasts. The bisphosphonates (BPs), pyrophosphate analogs that concentrate in bone, are to date the most effective inhibitor of bone resorption. BPs are taken up by osteoclasts, inhibiting their activity and causing the cells to undergo apoptosis, thereby inhibiting bone resorption. Advanced cancers are prone to metastasize. Effective treatments for bone metastases are not yet available—existing treatments such as bisphosphonates, chemotherapy and radiotherapy improve the quality of life with no life-prolonging benefits and have significant side effects.

SUMMARY

Disclosed herein are methods for the treatment of osteolytic disorders, in particular osteotropic cancer and osteoporosis. In one aspect, the invention provides methods for the treatment or prevention of an osteolytic disorder comprising administration of an effective amount of a MMP-14 or MMP-9 binding protein. In certain embodiments wherein the osteolytic disorder is osteotropic cancer, the methods act specifically to decrease and/or prevent the occurrence of osteolytic lesions which can occur due to metastatic spread to bone of a number of cancers including but not limited to breast, lung and prostate, by administration of a MMP-14 or MMP-9 binding protein. In other embodiments, the methods act specifically to prevent osteolytic lesions from forming in subjects having bone metastases, by administration of a MMP-14 or MMP-9 binding protein.

In one embodiment, an MMP-14 binding protein is administered in combination with an MMP-9 binding protein. In one embodiment, the MMP-14 or MMP-9 binding protein is administered in combination with an additional cancer therapeutic or treatment, such as, for example, bisphosphonates (e.g., amino and non-amino bisphosphonates), hormone-related compounds (e.g., estrogens and SERMs), RANKL antagonists, $\alpha_v\beta_3$ antagonists, Src inhibitors, cathepsin K inhibitors, calcitonin, chemotherapy and radiotherapy.

In one embodiment, an MMP-14 binding protein is administered in combination with an MMP-9 binding protein and an additional cancer therapeutic or treatment, such as, for example, bisphosphonates (e.g., amino and non-amino bisphosphonates), hormone-related compounds (e.g., estrogens and SERMs), RANKL antagonists, $\alpha_v\beta_3$ antagonists, Src inhibitors, cathepsin K inhibitors, calcitonin, chemotherapy and radiotherapy.

In one aspect, the invention provides kits for the treatment of an osteolytic disorder. The kits include a MMP-14 and/or MMP-9 binding protein, and instructions for administering the MMP-14 and/or MMP-9 binding protein to a subject having an osteolytic disorder. In one embodiment, the kit further includes instructions for administration of an additional therapeutic for the treatment of an osteolytic disorder, and may optionally contain the additional therapeutic. In one embodiment, the instructions provide a dosing regimen, dosing schedule, and/or route of administration of the MMP-14 and/or MMP-9 binding protein that differs from the dosing regimen, dosing schedule and/or route of administration for the inhibitor in the absence of the additional therapeutic.

In another aspect, provided herein is the use of a MMP-14 and/or MMP-9 binding protein for the manufacture of a medicament for the treatment of an osteolytic disorder. The medicament may optionally include an additional therapeutic for the treatment of an osteolytic disorder, such as a bisphosphonate.

The MMP-14 and/or MMP-9 binding protein used in any disclosed method, kit or composition can have one or more of the characteristics described below in the Detailed Description. Preferred compositions, e.g., used in any method or kit described herein, may further comprise one or more pharmaceutically acceptable buffers, carriers, and excipients, which may provide a desirable feature to the composition including, but not limited to, enhanced administration of the composition to a patient, enhanced circulating half-life of the inhibitor, enhanced compatibility of the composition with patient blood chemistry, enhanced storage of the composition, and/or enhanced efficacy of the composition upon administration to a patient.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts amino acid sequences (SEQ ID NOS 44-55, 22 and 56-66, respectively, in order of appearance) of Fab heavy chain (HC) and light chain (LC) variable regions of some exemplary MMP-14 binding proteins which may be used in the provided methods and compositions for treating osteolytic disorders. The standard numbering of the HC V domain is shown. The length of HC CDR3 varies considerably. By convention, the second cysteine is numbered 92 and the W of the conserved WG motif of FR4 is number 103. If there are more than 9 residues between C92 and W103, then residues after 102 are numbered 102a, 102b, etc.=

FIG. 3 depicts amino acid sequences (SEQ ID NOS 67-72, 67-68, 73-76, 67-68, 77-80, 68, 81-90, 68, 91-92, 79, 93-103, 79, 104-115, 110, 116-120, 110, 121-124, 120, 110, 125-126, 123, 127, 100-101, 128-145, 77, 146-152, 79, 153-160, 68, 73, 161-163, 160, 164-165, 79, 166-167, 145, 156, 168-177, 79, 178-200, 79, 201-202, 198, 203-215, 146-147, 216-217, 198, 218-221, 217, 198, 222-246, 198, 247-252, 156, 253-261, 202, 198, 203, 262-264, 202, 198, 203, 265-266, 206, 202, 198, 203-206, 202, 267-272, 198-199, 273-278, 223, 107, 279-280, 68, 281-285, 198, 286-289, 285, 233, 290-293, 285, 294, 199, 295-297, 256-258, 298-300, 285, 301-312, 77, 313, 296, 314-329, 67, 330-334, 101, 335-338, 202, 198, 339-341, 160, 95, 342-346, 101, 347-362, 202, 198, 363-370, 75, 371, 191-193, 372-387, 233, 388-411, 218, 412-414, 285, 198, 415-417, 285, 198, 418-429, 125, 430-433, 233 and 434-449, respectively, in order of appearance) of Fab heavy chain (HC) and light chain (LC) variable regions of some exemplary MMP-9 binding proteins which may be used in the provided methods and compositions for treating osteolytic disorders.

DETAILED DESCRIPTION

Figure 2:
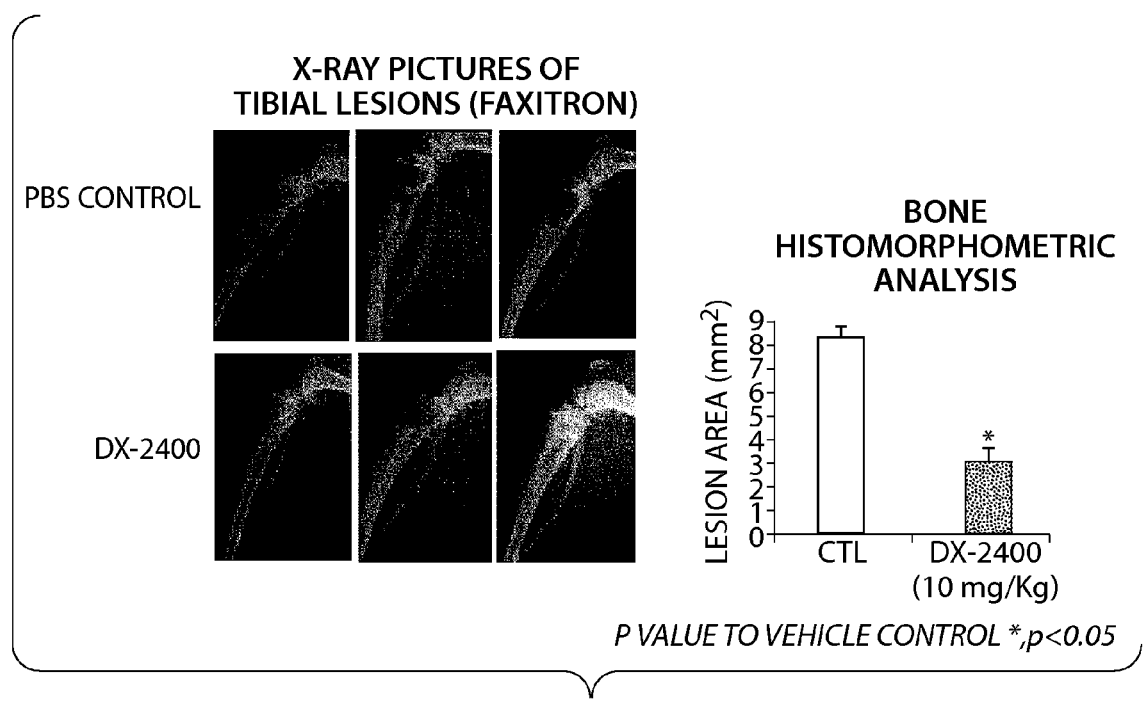
FIG. 2 depicts (left) X-ray analysis of the size of osteolytic tibial lesions treated with a PBS control (top) or DX-2400 (bottom) and (right) bone histomorphometric analysis of the size of osteolytic tibial lesions treated with a PBS control or DX-2400, as indicated.

Expression of MMP-2, MMP-9 and MMP-14 in sections from core bone biopsy specimens from patients with bone-metastatic prostate cancer has been observed. Further, expression of RANKL, MMP-2, MMP-13 and MMP-14 has been observed to be markedly elevated in bone with metastasis of breast cancer MDA-MB-231 cells in vivo. The disclosure provides methods of using MMP-14 or MMP-9 binding proteins, including MMP-14 or MMP-9 binding proteins that inhibit MMP-14 or MMP-9 binding activity, in the treatment and prevention of osteolytic disorders such as osteotropic cancer and osteoporosis, as well as compositions and kits for the same.

DEFINITIONS

For convenience, before further description of the present invention, certain terms employed in the specification, examples and appended claims are defined here.

The singular forms "a", "an", and "the" include plural references unless the context clearly dictates otherwise.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A. et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917. Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 10 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, "binding affinity" refers to the apparent association constant or $K_a$. The $K_a$ is the reciprocal of the dissociation constant ($K_d$). A binding protein may, for example, have a binding affinity of at least $10^5, 10^6, 10^7, 10^8, 10^9, 10^{10}$ and $10^{11}$ M$^{-1}$ for a particular target molecule, e.g., MMP-14, MMP-16, or MMP-24. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM CaCl$_2$ at pH 7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N \cdot [Free]/((1/Ka)+[Free]).$$

It is not always necessary to make an exact determination of $K_a$, though, since sometimes it is sufficient to obtain a quantitative measurement of affinity, e.g., determined using a method such as ELISA or FACS analysis, that is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding protein" refers to a protein or polypeptide that can interact with a target molecule. This term is used interchangeably with "ligand." An "MMP-14 binding protein" refers to a protein that can interact with MMP-14, and includes, in particular, proteins that preferentially interact with and/or inhibit MMP-14. For example, the MMP-14 binding protein may be an antibody. An "MMP-9 binding protein" refers to a protein that can interact with MMP-9, and includes, in particular, proteins that preferentially interact with and/or inhibit MMP-9. For example, the MMP-9 binding protein may be an antibody.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

The term "cognate ligand" refers to a naturally occurring ligand of an MMP-14 or MMP-9, including naturally occurring variants thereof (e.g., splice variants, naturally occurring mutants, and isoforms).

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An MMP-14 or MMP-9 binding protein may have mutations (e.g., at least one, two, or four, and/or less than 15, 10, 5, or 3) relative to a binding protein described herein (e.g., a conservative or non-essential amino acid substitutions), which do not have a substantial effect on protein function. Whether or not a particular substitution will be tolerated, i.e., will not adversely affect biological properties, such as binding activity can be predicted, e.g., by evaluating whether the mutation is conservative or by the method of Bowie; et al. (1990) *Science* 247:1306-1310.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with an MMP-14 or MMP-9 protein, e.g., the MMP-14 or MMP-9 catalytic domain.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

As used herein, the phrase "metastatic cancer" is defined as a cancer that has potential to spread to other areas of the body, particularly bone. A variety of cancers can metastasize to the bone, but the most common metastasizing cancers are breast, lung, renal, multiple myeloma, thyroid and prostate. By way of example, other cancers that have the potential to metastasize to bone include but are not limited to adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma and squamous cell cancer. The present invention especially contemplates prevention and treatment of tumor-induced osteolytic lesions in bone.

As used herein, an "osteolytic disorder" is any condition resulting from increased osteoclast activity. A subject at risk of an osteolytic disorder may be a subject in a group predisposed to develop an osteolytic disorder, or a subject suffering from a disease that causes or contributes to increased osteoclastic activity. In exemplary embodiments of the invention, the osteolytic disorder maybe a metabolic bone disease associated with relatively increased osteoclast activity, including an endocrinopathy (hypercortisolism, hypogonadism, primary or secondary hyperparathyroidism, hyperthyroidism), hypercalcemia, deficiency state (rickets/osteomalacia, scurvy, malnutrition), chronic disease (malabsorption syndromes, chronic renal failure (renal osteodystrophy), chronic liver disease (hepatic osteodystrophy)), drugs (glucocorticoids (glucocorticoid-induced osteoporosis), heparin, alcohol), or hereditary disease (osteogenesis imperfecta, homocystinuria), cancer, osteoporosis, osteopetrosis, inflammation of bone associated with arthritis and rheumatoid arthritis, periodontal disease, fibrous dysplasia, and/or Paget's disease. In other exemplary embodiments, the osteolytic disorder may be a metastatic cancer to bone (osteotropic cancer), wherein the metastatic cancer is breast, lung, renal, multiple myeloma, thyroid, prostate, adenocarcinoma, blood cell malignancy, including leukemia and lymphoma; head and neck cancer; gastrointestinal cancer, including esophageal cancer, stomach cancer, colon cancer, intestinal cancer, colorectal cancer, rectal cancer, pancreatic cancer, liver cancer, cancer of the bile duct or gall bladder; malignancy of the female genital tract, including ovarian carcinoma, uterine endometrial cancer, vaginal cancer, or cervical cancer; bladder cancer; brain cancer, including neuroblastoma; sarcoma, osteosarcoma; or skin cancer, including malignant melanoma or squamous cell cancer. In some embodiments, increased osteoclast activity, e.g., in a subject, refers to osteoclast activity that is increased as compared to the levels of osteoclast activity in a standard, e.g., the osteoclast activity in a cohort of subjects, e.g., a cohort of subjects without a symptom of an osteoclast disorder, or the levels of osteoclast activity of a random sampling of subjects. Osteoclast activity can increase by, e.g., about 10%, about 20%, about 30%, about 40%, about 50%, about 60%, about 70%, about 80%, about 90%, or more, as compared to the standard. Osteoclast activity can be measured, e.g., by tartrate resistant acid phosphatase (TRAP) staining; ELISA analysis of Receptor Activator for Nuclear Factor κB Ligand (RANKL) concentration in blood serum; and/or Alizarin Red staining of osteoblastic cells which were isolated from bone marrow. Additional methods are described, e.g., in WO 2003/031597.

The term "osteoporosis" refers to a disease in which the bones become extremely porous, are subject to fracture, and heal slowly, occurring especially in women following menopause and often leading to curvature of the spine from vertebral collapse.

The term "osteotropic cancer" refers to metastatic cancer of the bone, i.e., a secondary cancer present in bone that originates from a primary cancer, such as that of the breast, lung, or prostate.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen. Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Motif sequences for biopolymers can include positions which can be varied amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes.

For example, "(A/W/F/N/Q)" means that alanine, tryptophan, phenylalanine, asparagine, and glutamine are allowed at that particular position.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value<0.05 or 0.02).

The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition is outweighed by the therapeutically beneficial effects.

A "therapeutically effective dosage" preferably modulates a measurable parameter, e.g., levels of circulating IgG antibodies by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions, e.g., a cancer (e.g., metastatic cancer, e.g., metastatic breast cancer, e.g., osteotropic cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation. Alternatively, this property of a composition can be evaluated by examining the ability of the compound to modulate a parameter in vitro.

"Treating" a disease in a subject or "treating" a subject having a disease refers to subjecting the subject to a pharmaceutical treatment, e.g., the administration of a drug, such that at least one symptom of the disease is cured, alleviated or decreased.

"Tumor", as used herein, refers to all neoplastic cell growth and proliferation, whether malignant or benign, and all precancerous and cancerous cells and tissues.

MMP-14 Binding Proteins

MMP-14 expression is observed in bone samples from patients with bone-metastatic prostate cancer. Any MMP-14 binding protein, e.g., an MMP-14 binding protein described herein, may be used in the methods and compositions for treating osteolytic disorders that are disclosed herein. MMP-14 is encoded by a gene designated as MMP14, matrix metalloproteinase-14 precursor. Synonyms for MMP-14 include matrix metalloproteinase 14 (membrane-inserted), membrane-type-1 matrix metalloproteinase, membrane-type matrix metalloproteinase 1, MMP-14, MMP14, MMP-X1, MT1MMP, MT1-MMP, MTMMP1, MT-MMP 1. MT-MMPs have similar structures, including a signal peptide, a pro-domain, a catalytic domain, a hinge region, and a hemopexin domain (Wang, et al., 2004, J Biol Chem, 279:51148-55).

According to SwissProt entry P50281, the signal sequence of MMP-14 precursor includes amino acid residues 1-20. The pro-peptide includes residues 21-111. Cys93 is annotated as a possible cysteine switch. Residues 112 through 582 make up the mature, active protein. The catalytic domain includes residues 112-317. The hemopexin domains includes residues 318-523. The transmembrane segment comprises residues 542 through 562.

MMP-14 can be shed from cells or found on the surface of cells, tethered by a single transmembrane amino-acid sequence. See, e.g., Osnkowski et al. (2004, J Cell Physiol, 200:2-10).

The MMP-14 binding protein may be an isolated protein (e.g., at least 70, 80, 90, 95, or 99% free of other proteins).

The MMP-14 binding protein may additionally inhibit MMP-14, e.g., human MMP-14. In one embodiment, the protein binds the catalytic domain of human MMP-14, e.g., the protein contacts residues in or near the active site of MMP-14.

In certain embodiments, proteins that bind to MMP-14 (e.g., human MMP-14) and include at least one immunoglobulin variable region are used in the methods and compositions. For example, the MMP-14 binding protein includes a heavy chain (HC) immunoglobulin variable domain sequence and a light chain (LC) immunoglobulin variable domain sequence. A number of exemplary MMP-14 binding proteins are described herein.

MMP-14 binding proteins may also be antibodies. MMP-14 binding antibodies may have their HC and LC variable domain sequences included in a single polypeptide (e.g., scFv), or on different polypeptides (e.g., IgG or Fab). For example, antibodies may be raised against any of the following sequences:

An exemplary amino acid sequence of human MMP-14 is shown in Table 1:

Table 1: Amino-acid sequence of human MMP-14
MSPAPRPPRCLLLPLLTLGTALASLG-
SAQSSSFSPEAWLQQYGYLPPGDLRTHTQ RSPQSL-
SAAIAAMQKFYGLQVTGKADADTMKAMR-
RPRCGVPDKFGAEIKANV
RRKRYAIQGLKWQHNEITFCIQNYTP-
KVGEYATYEAIRKAFRVWESATPLRFRE
VPYAYIREGHEKQADIMIFFAEGFHGD-
STPFDGEGGFLAHAYFPGPNIGGDTHFD SAEP-
WTVRNEDLNGNDIFLVAVHELGHALGLE-
HSSDPSAIMAPFYQWMDTENF
VLPDDDRRGIQQLYGGESGFPTKMP-
PQPRTTSRPSVPDKPKNPTYGPNICDGNFD TVAML-
RGEMFVFKERWFWRVRNNQVMDGYP-
MPIGQFWRGLPASINTAYERK
DGKFVFFKGDKHWVFDEASLEPGYPKHIKELGR
FYKGNKYWKFNNQKLKVEP GYPKSALRDWMGCP
SGGRPDEGTEEETEVI I IEVDEEGGGAVSAAAVVL
PVLLLLLVLAVGLAVFFFRRHGTPRRL-
LYCQRSLLDKV (SEQ ID NO:1; GENBANK®" Accession No. CAA88372.1).

An exemplary amino acid sequence of mouse MMP-14 is shown in Table 2.

Table 2: Amino-acid sequence of mouse MMP-14
MSPAPRPSRSLLLPLLTLGTALASLG-
WAQGSNFSPEAWLQQYGYLPPGD LRTHTQRSPQSL-
SAAIAAMQKFYGLQVTGKADLATMMAMR-
RPRCGVP
DKFGTEIKANVRRKRYAIQGLKWQH-
NEITFCIQNYTPKVGEYATFEAIR KAFRVWESATPLR-
FREVPYAYIREGHEKQADIMILFAEGFHGDSTPFDG
EGGFLAHAYFPGPNIGGDTHFDSAEP- WTVQNEDLNGNDIFLVAVHELG HALGLEHSNDP-
SAIMSPFYQWMDTENFVLPDDDRRGIQQ-
LYGSKSGSPT
KMPPQPRTTSRPSVPDKPKNPAYGP-
NICDGNFDTVAMLRGEMFVFKER WFWRVRN-
NQVMDGYPMPIGQFWRGLPASINTVD-
SEYPKNIKVWEGIPE
SPRGSFMGSDEVFTYFYKGNKYWKFN-
NQKLKVEPGYPKSALRDWMGC PSGRRPDEG-
TEEETEVIIIEVDEEGSGAVSAAAVV-
LPVLLLLLVLAVGLA
VFFFRRHGTPKRLLYCQRSLLDKV SEQ ID NO:2; GEN-
BANK®" Accession No. NP_032634.2.

An exemplary MMP-14 protein against which MMP-14 binding proteins may be developed can include the human or mouse MMP-14 amino acid sequence, a sequence that is 80%, 85%, 90%, 95%, 96%, 97%, 98%, or 99% identical to one of these sequences, or a fragment thereof, e.g., a fragment without the signal sequence or prodomain.

Exemplary MMP-14 binding proteins include M0031-C02, M0031-F01, M0033-H07, M0037-C09, M0037-D01, M0038-E06, M0038-F01, M0038-F08, M0039-H08, M0040-A06, M0040-A11, and M0043-G02. The amino acid sequences of exemplary Fab heavy chain (HC) and light chain (LC) variable regions of these binding proteins are shown in FIG. 1, and further description of them and their discovery and production is provided in pending application U.S. Ser. No. 11/648,423 (U.S. 2007-0217997), which is hereby incorporated by reference in its entirety. Other exemplary MMP-14 binding proteins include DX-2400 and DX-2410. DX-2400 and M0038-F01 share HC and LC CDR amino acid sequences. The amino acid sequences of the heavy chain and light chain variable regions of these proteins are provided in the Examples.

Other MMP-14 inhibitors known in the art include, but are not limited to, those disclosed in the following patents and patent applications: U.S. Pat. No. 6,114,159; U.S. Pat. No. 6,399,348; JP 3802560 and EP 0750672 (all in the name of Max Delbrueck Center for Molecular Medicine); U.S. Pat. No. 6,184,022; U.S. Pat. No. 6,825,024; EP 0685557; JP 2694604 (all in the name of Daiichi Fine Chemicals); and U.S. Provisional Application Ser. Nos. 60/755,376 and 60/805,567 (both in the name of Dyax Corp.).

MMP-9 and MMP-9 Binding Entities

Any MMP-9 binding protein may be used in the methods and compositions for treating osteolytic disorders that are disclosed herein.

MMP-9 is encoded by a gene designated as MMP9 with full name Matrix metalloproteinase-9 precursor. Synonyms for MMP-9 include matrix metalloproteinase 9, gelatinase B (GELB), 92 kDa gelatinase (CLG4B), 92 kDa type IV collagenase (EC 3.4.24.35). The DNA sequence is known for *Homo sapiens* and *Mus musculus*. An exemplary cDNA sequence encoding human MMP9 and the amino acid sequence are shown below. Exemplary cDNA sequences encoding murine MMP9 and amino acid sequences are also shown below. An exemplary MMP-9 protein can include the human or mouse MMP-9 amino acid sequence, a sequence that is 80%, 85%, 90%, 95%, 96%, 97%, 98%, or 99% identical to one of these sequences, or a fragment thereof, e.g., a fragment without the signal sequence or prodomain.

Table 3 shows the similar genes in other organisms and the percentage of similarity with human MMP-9. No similarity-to-human data found for MMP9 for: chimpanzee (*Pan troglodytes*), pig (*Sus scrofa*), cow (*Bos taurus*), fruit fly (*Drosophila melanogaster*), worm (*Caenorhabditis elegans*), baker's yeast (*Saccharomyces cerevisiae*), tropical clawed frog (*Silurana tropicalis*), African malaria mosquito (*Anopheles gambiae*), green algae (*Chlamydomonas reinhardtii*), soybean (*Glycine max*), barley (*Hordeum vulgare*), tomato (*Lycopersicon esculentum*), rice blast fungus (*Magnaporthe grisea*), sugarcane (*Saccharum officinarum*), loblolly pine (*Pinus taeda*), corn (*Zea mays*), wheat (*Triticum aestivum*), Alicante grape (*Vitis vinifera*), bread mold (*Neurospora crassa*), fission yeast (*Schizosaccharomyces pombe*), sea squirt (*Ciona intestinalis*), amoeba (*Dictyostelium discoideum*), *A. gosspyii* yeast (*Ashbya gossypii*), *K. lactis* yeast (*Kluyveromyces lactis*), medicago trunc (*Medicago truncatula*), malaria parasite (*Plasmodium falciparum*), schistosome parasite (*Schistosoma mansoni*), sorghum (*Sorghum bicolor*), toxoplasmosis (*Toxoplasma gondii*).

```
cDNA and amino acid sequences of human MMP9
ACCESSION            AK123156
VERSION              AK123156.1         GI: 34528630
                                                  (SEQ ID NO: 3)
translation = "MARKGARRPRQGPGSHKWLQPGSRREKERIPQPPPPARPPRDAAPRRVLPAVRR

VPESGHFAGRPWAPQCHPKGLRRPSAESHSVAQAGVQCHDLGSLQPPPPSSGDSPASASRVAGITSTVPG

TLSALDDCCLITELPYKPPAVLY"

(SEQ ID NO: 4)
   1 acactttgcg ttccgcggcc ccggcccctt ggtttcctag tcctggctcc attcccctct 61 caggcctagg gctgggaccc ctcccgccc ccggtcttgg ccctgccccc ttcaacagac 121 ggtccgcccc ggcccctccc cctcgtcccg cccggccctg gcaggccccg cccctgcgg 181 cctctacctt tgacgtcttc ccccgggagg tggcgggggt ctgcgaccga atgccggcgg 241 gactctgggt cagggcttct ggcgggccct gcgggggggca gcgaggtgac cgtgaacctg 301 cggctcatgg cgcggaaagg agccaggcgg ccgcggcaag gtccgggatc gcacaagtgg 361 ctgcaaccag gctctaggag ggagaaagag cggatccccc aaccccctcc gcccgcccgc 421 ccccgcgag acgcggcgcc gcgcagggtc ctagtgcccg ctgtgcgaag ggttcctgaa 481 tctggccact tcgctgggag gccctgggct ccccagtgcc acccgaaggg cctgaggagg
```

-continued

```
541 ccatctgcag aatctcactc tgtcgcccag gccggagtgc agtgtcatga tcttggctca 601 ctgcaacctc cgcctcccag ttcaggagat tctcctgcct cagcctcccg ggtggctggg 661 attacaagca cagtgcctgg cacattatcg gcacttgatg actgttgtct aataactgag 721 cttccataca aaccacctgc cgtcctgtac tgaaggagaa agagcttcca gccggggagg 781 caggaaatct gggtcctggt cttggttgca tccctgactt cctaaatgac ctggagaagg 841 cctctgcctc tgctgggatc ttgtctgtgc tggggcattt gtttccattt ccaagggctt 901 tttcttcctc gctcagaatt tgaccactca ctaagaggag cttagtgtgg tgtctcacga 961 agggatcctc ctcagccctc acctcggtac tggaagacgt cgtgcgtgtc caaaggcacc 1021 ccggggaaca tccggtccac ctcgctggcg ctccggggat ccaccatctg cgccttcacg 1081 tcgaacctgc gggcaggcgc ggaggagaca ggtgctgagc cggctagcgg acggaccgac 1141 ggcgcccggg ctccccctgc cggcggccgc ggcggcgctc acctcagag cgccgcccg 1201 ctgaacagca gcatcttccc cctgccactc cggagggccc cggtcacctg gccacgtcg 1261 gcgcccaggc ccagcttgtc cagacgcctc gggcccagca ccgacgcgcc tgtgtacacc 1321 cacacctggc gccctgcagg ggaggagggt cacgtcggtt tgggggcgca gagggagcac 1381 gtactcctag aacgcgagga gggagattcc ggcgaggcct ttcctagccc gcgtgcccgc 1441 agtccctgca acccaggggc agaggcgctg ggtagagcga cgcgagggcg tggagaggag 1501 ggggcagaaa ctcagccgcc cctacgtttg ctaaactgcg tccgccaggg ggcgtatttt 1561 tctaaaacgc acaagacgtt tcgtgggtta tcgatggtct cttgagcctc cttgactgat 1621 ggggattgac cggggcggggg agggaaagta ggtaactaac cagagaagaa gaaaagcttc 1681 ttggagagcg gctcctcaaa gaccgagtcc agcttgcggg gcagcgcggg ccacttgtcg 1741 gcgataagga aggggccctg cggccggctc cccctgccct cagagaatcg ccagtacttc 1801 ctgagaaagc gaggagggaa aggacgggct ctaagccttg gacacaggc cagtgggcgg 1861 gaagggacgg gcagccctc cgcaaagccc cctcccgcat ccacacaacc ccgcctcctc 1921 acccatcctt gaacaaatac agctggttcc caatc
``` cDNA and amino acid sequences of mouse MMP9
ACCESSION          NM_013599
VERSION            NM_013599.2           GI: 31560795

(SEQ ID NO: 5)
translation = "MSPWQPLLLALLAFGCSSAAPYQRQPTFVVFPKDLKTSNLTDTQLAEAYLYRYGY
TRAAQMMGEKQSLRPALLMLQKQLSLPQTGELDSQTLKAIRTPRCGVPDVGRFQTFKGLKWDHHNITYWI
QNYSEDLPRDMIDDAFARAFAVWGEVAPLTFTRVYGPEADIVIQFGVAEHGDGYPFDGKDGLLAHAFPPG
AGVQGDAHFDDDELWSLGKGVVIPTYYGNSNGAPCHFPFTFEGRSYSACTTDGRNDGTPWCSTTADYDKD
GKFGFCPSERLYTEHGNGEGKPCVFPFIFEGRSYSACTTKGRSDGYRWCATTANYDQDKLYGFCPTRVDA
TVVGGNSAGELCVFPFVFLGKQYSSCTSDGRRDGRLWCATTSNFDTDKKWGFCPDQGYSLFLVAAHEFGH
ALGLDHSSVPEALMYPLYSYLEGFPLNKDDIDGIQYLYGRGSKPDPRPPATTTTEPQPTAPPTMCPTIPP
TAYPTVGPTVGPTGAPSPGPTSSPSPGPTGAPSPGPTAPPTAGSSEASTESLSPADNPCNVDVFDAIAEI
QGALHFFKDGWYWKFLNHRGSPLQGPFLTARTWPALPATLDSAFEDPQTKRVFFFSGRQMWVYTGKTVLG
PRSLDKLGLGPEVTHVSGLLPRRLGKALLFSKGRVWRFDLKSQKVDPQSVIRVDKEFSGVPWNSHDIFQY
QDKAYFCHGKFFWRVSFQNEVNKVDHEVNQVDDVGYVTYDLLQCP"

(SEQ ID NO: 6)
```
  1 ctcaccatga gtccctggca gcccctgctc ctggctctcc tggctttcgg ctgcagctct 61 gctgcccctt accagcgcca gccgactttt gtggtcttcc ccaaagacct gaaaacctcc 121 aacctcacgg acacccagct ggcagaggca tacttgtacc gctatggtta cacccgggcc
```

-continued

```
 181 gcccagatga tgggagagaa gcagtctcta cggccggctt tgctgatgct tcagaagcag
 241 ctctccctgc cccagactgg tgagctggac agccagacac taaaggccat tcgaacacca
 301 cgctgtggtg tcccagacgt gggtcgattc caaaccttca aaggcctcaa gtgggaccat
 361 cataacatca catactggat ccaaaactac tctgaagact tgccgcgaga catgatcgat
 421 gacgccttcg cgcgcgcctt cgcggtgtgg ggcgaggtgg caccctcac cttcacccgc
 481 gtgtacggac ccgaagcgga cattgtcatc cagtttggtg tcgcggagca cggagacggg
 541 tatcccttcg acggcaagga cggccttctg gcacacgcct ttcccctgg cgccggcgtt
 601 cagggagatg cccatttcga cgacgacgag ttgtggtcgc tgggcaaagg cgtcgtgatc
 661 cccacttact atggaaactc aaatggtgcc ccatgtcact ttcccttcac cttcgaggga
 721 cgctcctatt cggcctgcac cacagacggc cgcaacgacg gcacgccttg gtgtagcaca
 781 acagctgact acgataagga cggcaaattt ggtttctgcc ctagtgagag actctacacg
 841 gagcacggca acgagaagg caaaccctgt gtgttcccgt tcatctttga gggccgctcc
 901 tactctgcct gcaccactaa aggccgctcg gatggttacc gctggtgcgc caccacagcc
 961 aactatgacc aggataaact gtatggcttc tgccctaccc gagtggacgc gaccgtagtt
1021 gggggcaact cggcaggaga gctgtgcgtc ttccccttcg tcttcctggg caagcagtac
1081 tcttcctgta ccagcgacgg ccgcagggat gggcgcctct ggtgtgcgac acatcgaac
1141 ttcgacactg acaagaagtg gggttctgt ccagaccaag ggtacagcct gttcctggtg
1201 gcagcgcacg agttcggcca tgcactgggc ttagatcatt ccagcgtgcc ggaagcgctc
1261 atgtacccgc tgtatagcta cctcgagggc ttccctctga ataaagacga catagacggc
1321 atccagtatc tgtatggtcg tggctctaag cctgacccaa ggcctccagc caccaccaca
1381 actgaaccac agccgacagc acctcccact atgtgtccca ctatacctcc cacggcctat
1441 cccacagtgg gccccacggt tggccctaca ggcgcccct cacctggccc cacaagcagc
1501 ccgtcacctg gccctacagg cgccccctca cctggcccta cagcgccccc tactgcgggc
1561 tcttctgagg cctctacaga gtctttgagt ccggcagaca atccttgcaa tgtggatgtt
1621 tttgatgcta ttgctgagat ccagggcgct ctgcatttct tcaaggacgg ttggtactgg
1681 aagttcctga atcatagagg aagcccatta cagggcccct tccttactgc ccgcacgtgg
1741 ccagcccctgc ctgcaacgct ggactccgcc tttgaggaic cgcagaccaa gagggttttc
1801 ttcttctctg gacgtcaaat gtgggtgtac acaggcaaga ccgtgctggg ccccaggagt
1861 ctggataagt tgggtctagg cccagaggta acccacgtca gcgggcttct cccgcgtcgt
1921 ctcgggaagg ctctgctgtt cagcaagggg cgtgtctgga gattcgactt gaagtctcag
1981 aaggtggatc cccagagcgt cattcgcgtg gataaggagt tctctggtgt gccctggaac
2041 tcacacgaca tcttccagta ccaagacaaa gcctatttct gccatggcaa attcttctgg
2101 cgtgtgagtt tccaaaatga ggtgaacaag gtggaccatg aggtgaacca ggtgacgac
2161 gtgggctacg tgacctacga cctcctgcag tgcccttgaa ctagggctcc ttctttgctt
2221 caaccgtgca gtgcaagtct ctagagacca ccaccaccac caccacacac aaacccatc
2281 cgagggaaag gtgctagctg ccaggtaca gactgggigat ctcttctaga gactgggaag
2341 gagtggaggc aggcagggct ctctctgccc accgtccttt cttgttggac tgtttctaat
2401 aaacacggat ccccaacctt ttccagctac tttagtcaat cagcttatct gtagttgcag
2461 atgcatccga gcaagaagac aactttgtag ggtggattct gacctttat ttttgtgtgg
2521 cgtctgagaa ttgaatcagc tggcttttgt gacaggcact tcaccggcta aaccacctct
2581 cccgactcca gccctttat ttattatgta tgaggttatg ttcacatgca tgtatttaac
```

-continued

```
2641 ccacagaatg cttactgtgt gtcgggcgcg gctccaaccg ctgcataaat attaaggtat 2701 tcagttgccc ctactggaag gtattatgta actatttctc tcttacattg gagaacacca 2761 ccgagctatc cactcatcaa acatttattg agagcatccc tagggagcca ggctctctac 2821 tgggcgttag ggacagaaat gttggttctt ccttcaagga ttgctcagag attctccgtg 2881 tcctgtaaat ctgctgaaac cagaccccag actcctctct ctcccgagag tccaactcac 2941 tcactgtggt tgctggcagc tgcagcatgc gtatacagca tgtgtgctag agaggtagag 3001 ggggtctgtg cgttatggtt caggtcagac tgtgtcctcc aggtgagatg acccctcagc 3061 tggaactgat ccaggaagga taaccaagtg tcttcctggc agtctttttt aaataaatga 3121 ataaatgaat atttacttaa aaaaaaaaaa aaaaaaaaaa aaaaaaaaaa aaaaaaaaaa 3181 aaaaa ACCESSION           NP_038627
VERSION             NP_038627.1              GI: 7305277
                                                      (SEQ ID NO: 7)
  1 mspwqpllla llafgcssaa pyqrqptfvv fpkdlktsnl tdtqlaeayl yrygytraaq 61 mmgekqslrp allmlqkqls lpqtgeldsq tlkairtprc gvpdvgrfqt fkglkwdhhn 121 itywiqnyse dlprdmidda farafavwge vapltftrvy gpeadiviqf gvaehgdgyp 181 fdgkdgllah afppgagvqg dahfdddelw slgkgvvipt yygnsngapc hfpftfegrs 241 ysacttdgrn dgtpwcstta dydkdgkfgf cpserlyteh gngegkpcvf pfifegrsys 301 acttkgrsdg yrwcattany dqdklygfcp trvdatvvgg nsagelcvfp fvflgkqyss 361 ctsdgrrdgr lwcattsnfd tdkkwgfcpd qgyslflvaa hefghalgld hssvpealmy 421 plysylegfp lnkddidgiq ylygrgskpd prppatttte pqptapptmc ptipptaypt 481 vgptvgptga pspgptssps pgptgapspg ptapptagss easteslspa dnpcnvdvfd 541 aiaeiqgalh ffkdgwywkf lnhrgsplqg pfltartwpa lpatldsafe dpqtkrvfff 601 sgrqmwvytg ktvlgprsld klglgpevth vsgllprrlg kallfskgrv wrfdlksqkv 661 dpqsvirvdk efsgvpwnsh difqyqdkay fchgkffwrv sfqnevnkvd hevnqvddvg 721 yvtydllqcp
```

TABLE 3

MMP-9 orthologs from nine species

| Organism | Gene | Locus | Description | Human Similarity | s |
|---|---|---|---|---|---|
| dog (Canis familiaris) | MMP9[1] | — | matrix metallopeptidase 9 (gelatinase B, 92 kDa gelatinase | 85.46(n) 80.97(a) | 403885 NM_001003219.1 NP_001003219.1 |
| rat (Rattus norvegicus) | Mmp9[1] | — | matrix metallopeptidase 9 | 79.15(n) 74.89(a) | 81687 NM_031055.1 NP_112317.1 |
| mouse (Mus musculus) | Mmp9[1,4] | 2 (96.00 cM)[4] | matrix metallopeptidase 9[1,4] | 78.69(n)[1] 75(a)[1] | 17395[1] NM_013599.2[1] NP_038627.1[1] AK004651[4] AK142787[4] (see all 16) |
| chicken (Gallus gallus) | LOC395387[1] | — | matrix metallopeptidase 9 (gelatinase B, 92 kDa gelatinase | 66.96(n) 62.54(a) | 395387 NM_204667.1 NP_989998.1 |
| zebrafish (Danio rerio) | wufb02g06[1−] | — | Danio rerio cDNA clone MGC64165 IMAGE6797338, complete | 70.96(n) | BC053292.1 |
| African clawed frog (Xenopus laevis) | MGC69080[1−] | — | hypothetical protein MGC69080 | 72.25(n) | BC057745.1 |

TABLE 3-continued

MMP-9 orthologs from nine species

| Organism | Gene | Locus | Description | Human Similarity | s |
|---|---|---|---|---|---|
| rainbow trout (*Oncorhynchus mykiss*) | Omy.10476[1-] | — | *Oncorhynchus mykiss* mRNA for matrix metalloproteinase | 74.67(n) | AJ320533.1 |
| thale cress (*Arabidopsis thaliana*) | MMP[1] | — | MMP (MATRIX METALLOPROTEINASE); metalloendopeptidase/ | 53(n) 46.85(a) | 843353 NM_105685.3 NP_177174.1 |
| rice (*Oryza sativa*) | P0516G10.18[1] | — | putative zinc metalloproteinase | 51.98(n) 41.81(a) | 3063368 XM_467714.1 XP_467714.1 |

Domains of MMP-9. MMP-9 belongs to the peptidase M10A family. MMP-9 consists of five domains; the amino-terminal and zinc-binding domains shared by all members of the secreted metalloprotease gene family, the collagen-binding fibronectin-like domain also present in the 72-kDa type IV collagenase, a carboxyl-terminal hemopexin-like domain shared by all known enzymes of this family with the exception of PUMP-1, and a unique 54-amino-acid-long proline-rich domain homologous to the alpha 2 chain of type V collagen (Wilhelm et al. (1989) *J. Biol. Chem.* 264, 17213-17221) (Table 4).

TABLE 4

MMP-9 domains

| FT | SIGNAL | 1 | 19 | |
|---|---|---|---|---|
| FT | PROPEP | 20 | 93 | Activation peptide. |
| FT | CHAIN | 94 | ? | 67 kDa matrix metalloproteinase-9. |
| FT | CHAIN | 107 | 707 | 82 kDa matrix metalloproteinase-9. |
| FT | PROPEP | ? | 707 | Removed in 64 kDa matrix |
| FT | | | | metalloproteinase-9 and 67 kDa |
| FT | | | | matrix |
| FT | | | | metalloproteinase-9. |
| FT | DOMAIN | 225 | 273 | Fibronectin type-II 1. |
| FT | DOMAIN | 283 | 331 | Fibronectin type-II 2. |
| FT | DOMAIN | 342 | 390 | Fibronectin type-II 3. |
| FT | DOMAIN | 513 | 707 | Hemopexin-like. |
| FT | ACT_SITE | 402 | 402 | |
| FT | METAL | 131 | 131 | Calcium 1. |
| FT | METAL | 165 | 165 | Calcium 2 (via carbonyl oxygen). |
| FT | METAL | 175 | 175 | Zinc 1 (structural). |
| FT | METAL | 177 | 177 | Zinc 1 (structural). |
| FT | METAL | 182 | 182 | Calcium 3. |
| FT | METAL | 183 | 183 | Calcium 3 (via carbonyl oxygen). |
| FT | METAL | 185 | 185 | Calcium 3 (via carbonyl oxygen). |
| FT | METAL | 187 | 187 | Calcium 3 (via carbonyl oxygen). |
| FT | METAL | 190 | 190 | Zinc 1 (structural). |
| FT | METAL | 197 | 197 | Calcium 2 (via carbonyl oxygen). |
| FT | METAL | 199 | 199 | Calcium 2 (via carbonyl oxygen). |
| FT | METAL | 201 | 201 | Calcium 2. |
| FT | METAL | 203 | 203 | Zinc 1 (structural). |
| FT | METAL | 205 | 205 | Calcium 3. |
| FT | METAL | 206 | 206 | Calcium 1. |
| FT | METAL | 208 | 208 | Calcium 1. |
| FT | METAL | 208 | 208 | Calcium 3. |
| FT | METAL | 401 | 401 | Zinc 2 (catalytic). |
| FT | METAL | 405 | 405 | Zinc 2 (catalytic). |
| FT | METAL | 411 | 411 | Zinc 2 (catalytic). |
| FT | SITE | 59 | 60 | Cleavage (by MMP3). |
| FT | SITE | 99 | 99 | Cysteine switch (By similarity). |
| FT | SITE | 106 | 107 | Cleavage (by MMP3). |
| FT | CARBOHYD | 38 | 38 | N-linked (GlcNAc . . . ) (Potential). |
| FT | CARBOHYD | 120 | 120 | N-linked (GlcNAc . . . ) (Potential). |
| FT | CARBOHYD | 127 | 127 | N-linked (GlcNAc . . . ) (Potential). |
| FT | DISULFID | 230 | 256 | By similarity. |
| FT | DISULFID | 244 | 271 | By similarity. |
| FT | DISULFID | 288 | 314 | By similarity. |
| FT | DISULFID | 302 | 329 | By similarity. |
| FT | DISULFID | 347 | 373 | By similarity. |
| FT | DISULFID | 361 | 388 | By similarity. |
| FT | DISULFID | 516 | 704 | |
| FT | VARIANT | 20 | 20 | A -> V (in dbSNP: rs1805088). |
| FT | VARIANT | 82 | 82 | E -> K (in dbSNP: rs1805089). |
| FT | VARIANT | 127 | 127 | N -> K (in dbSNP: rs3918252). |
| FT | VARIANT | 239 | 239 | R -> H. |
| FT | VARIANT | 279 | 279 | R -> Q (common polymorphism; dbSNP: rs17576). |
| FT | VARIANT | 571 | 571 | F -> V. |
| FT | VARIANT | 574 | 574 | P -> R (in dbSNP: rs2250889). |
| FT | VARIANT | 668 | 668 | R -> Q (in dbSNP: rs17577). |
| FT | TURN | 32 | 33 | |
| FT | HELIX | 41 | 51 | |
| FT | TURN | 52 | 53 | |
| FT | HELIX | 68 | 78 | |
| FT | TURN | 79 | 79 | |
| FT | HELIX | 88 | 94 | |
| FT | TURN | 95 | 95 | |
| FT | STRAND | 103 | 105 | |
| FT | STRAND | 119 | 125 | |
| FT | STRAND | 130 | 132 | |
| FT | HELIX | 134 | 149 | |
| FT | TURN | 150 | 150 | |
| FT | STRAND | 151 | 153 | |
| FT | STRAND | 155 | 158 | |
| FT | TURN | 162 | 163 | |
| FT | STRAND | 164 | 171 | |
| FT | STRAND | 176 | 178 | |
| FT | STRAND | 183 | 186 | |
| FT | STRAND | 189 | 191 | |
| FT | STRAND | 194 | 196 | |
| FT | TURN | 197 | 200 | |
| FT | STRAND | 202 | 205 | |
| FT | TURN | 206 | 207 | |
| FT | STRAND | 213 | 219 | |
| FT | HELIX | 220 | 231 | |
| FT | TURN | 232 | 233 | |
| FT | TURN | 240 | 241 | |
| FT | TURN | 243 | 244 | |
| FT | STRAND | 245 | 247 | |
| FT | STRAND | 255 | 261 | |
| FT | HELIX | 262 | 265 | |
| FT | STRAND | 268 | 270 | |
| FT | TURN | 274 | 276 | |
| FT | STRAND | 279 | 283 | |
| FT | TURN | 284 | 285 | |
| FT | STRAND | 290 | 294 | |
| FT | TURN | 295 | 296 | |
| FT | STRAND | 297 | 301 | |
| FT | TURN | 305 | 306 | |
| FT | STRAND | 313 | 319 | |
| FT | HELIX | 320 | 323 | |
| FT | STRAND | 326 | 328 | |
| FT | HELIX | 333 | 335 | |
| FT | TURN | 340 | 344 | |
| FT | STRAND | 349 | 353 | |

TABLE 4-continued

MMP-9 domains

| | | | |
|---|---|---|---|
| FT | TURN | 354 | 355 |
| FT | STRAND | 356 | 358 |
| FT | TURN | 364 | 365 |
| FT | STRAND | 372 | 378 |
| FT | HELIX | 379 | 382 |
| FT | STRAND | 385 | 387 |
| FT | HELIX | 395 | 406 |
| FT | TURN | 407 | 408 |
| FT | TURN | 415 | 416 |
| FT | TURN | 418 | 419 |
| FT | HELIX | 433 | 442 |
| FT | STRAND | 512 | 517 |
| FT | HELIX | 515 | 517 |
| FT | STRAND | 522 | 527 |
| FT | TURN | 528 | 529 |
| FT | STRAND | 530 | 535 |
| FT | TURN | 536 | 537 |
| FT | STRAND | 538 | 542 |
| FT | STRAND | 545 | 547 |
| FT | STRAND | 551 | 555 |
| FT | HELIX | 556 | 559 |
| FT | TURN | 561 | 562 |
| FT | STRAND | 568 | 572 |
| FT | TURN | 574 | 576 |
| FT | STRAND | 579 | 583 |
| FT | TURN | 584 | 585 |
| FT | STRAND | 586 | 591 |
| FT | TURN | 592 | 593 |
| FT | STRAND | 594 | 600 |
| FT | HELIX | 601 | 604 |
| FT | TURN | 605 | 605 |
| FT | TURN | 608 | 609 |
| FT | STRAND | 615 | 618 |
| FT | TURN | 621 | 622 |
| FT | STRAND | 623 | 628 |
| FT | TURN | 629 | 630 |
| FT | STRAND | 631 | 636 |
| FT | TURN | 637 | 640 |
| FT | HELIX | 644 | 646 |
| FT | HELIX | 650 | 653 |
| FT | TURN | 655 | 656 |
| FT | STRAND | 662 | 667 |
| FT | TURN | 668 | 669 |
| FT | STRAND | 670 | 675 |
| FT | TURN | 676 | 677 |
| FT | STRAND | 678 | 683 |
| FT | TURN | 686 | 687 |
| FT | STRAND | 690 | 696 |
| FT | TURN | 697 | 700 |
| FT | TURN | 702 | 703 |

The catalytic activity of MMP-9 is inhibited by histatin-3 1/24 (histatin-5). MMP-9 is activated by urokinase-type plasminogen activator; plasminogen; IL-1beta, 4-aminophenylmercuric acetate and phorbol ester. MMP-9 exists as monomer, disulfide-linked homodimer, and as a heterodimer with a 25 kDa protein. Macrophages and transformed cell lines produce only the monomeric MMP-9, the hetrodimeric form is produced by normal alveolar macrophages and granulocytes. The processing of the precursor yields different active forms of 64, 67 and 82 kDa. Sequentially processing by MMP-3 yields the 82 kDa matrix metalloproteinase-9. In arthritis patients, this enzyme can contribute to the pathogenesis of joint destruction and can be a useful marker of disease status.

Endogenous inhibitors of MMP-9. MMP-9 has a number of endogenous inhibitors. Like other MMPs, MMP-9 is inhibited by TIMPs (Murphy, G., and Willenbrock, F. (1995) *Methods Enzymol.* 248, 496-510). A characteristic of MMP-9 (and MMP-2) is the ability of their zymogens to form tight non-covalent and stable complexes with TIMPs. It has been shown that pro-MMP-2 binds TIMP-2 (Goldberg et al. (1989) *Proc. Natl. Acad. Sci. U.S.A.* 86, 8207-8211), whereas pro-MMP-9 binds TIMP-1 (Wilhelm et al. (1989) *J. Biol. Chem.* 264, 17213-17221). TIMPs typically are slow, tight binding inhibitors. A MMP-9 binding protein (e.g., antibody, peptide, Kunitz domain) selected from a library of phage-displayed proteins can be selected have more rapid kinetics. For example, recombinant TIMP-1 can be administered to inhibit MMP-9, e.g., in combination with a MMP-9 binding protein described herein.

Small molecule inhibitors of MMP-9. Skiles et al. (2004, Curr Med Chem, 11:2911-77) reported that first generation small-molecule MMP inhibitors had poor bioavailability and the second generation had caused musculoskeletal pain and inflammation. Most small-molecule MMP inhibitors interact with the catalytic zinc but have fairly low affinity. Thus, a higher concentration is needed to have effect. The interaction with the catalytic zinc leads to inhibition of other MMPs and toxic side effects. A MMP-9 binding protein described herein can be used in combination with a small molecule inhibitor. For example, because the inhibitors are used in combination, the dose of the small molecule used can be decreased and therefore result in fewer side effects. Examples of small molecule MMP-9 inhibitors include small synthetic anthranilic acid-based inhibitors (see, e.g., CALBIOCHEM® Inhibitor-I, catalogue #444278 and Levin et al., 2001, *Bioorg. Med. Chem. Lett.* 11:2975-2978).

Small interfering RNA inhibitors of MMP-9. MMP-9 can be inhibited by small interfering RNA (siRNA). Examples of siRNA that can be used include:

```
MMP-9 siRNA
  5'-GACUUGCCGCGAGACAUGAtt-3'      (SEQ ID NO: 8)

3'-ttCUGAACGGCGCUCUGUACU-5'      (SEQ ID NO: 9)

Control RNA (mismatch)
  5'-GACUUCGCGGGACACAUGAtt-3'      (SEQ ID NO: 10)

3'-ttCUGAAGCGCCCUGUGUACU-5'      (SEQ ID NO: 11)
```

See also Kawasaki et al., Feb. 10, 2008, *Nat. Med.* advance on-line publication doi:10.1038/nm1723. The siRNA can be administered to inhibit MMP-9, e.g., in combination with a MMP-9 binding protein described herein.

MMP-9 Binding Proteins

Provided also are proteins that bind to MMP-9 (e.g., human MMP-9) and are either peptides, polypeptides that include at least one immunoglobin variable region, or Kunitz domains. Methods for discovering and selecting and improving such binding proteins are described further below. MMP-9 expression is observed in bone samples from patients with bone-metastatic prostate cancer. An MMP-9 binding protein, e.g., an MMP-9 binding protein described herein, can be used in the methods described herein, e.g., to treat an osteolytic disorder.

In a preferred embodiment, the MMP-9 binding protein includes at least one immunoglobulin variable domain. For example, the MMP-9 binding protein includes a heavy chain (HC) immunoglobulin variable domain sequence and a light chain (LC) immunoglobulin variable domain sequence. A number of exemplary MMP-9 binding proteins are described herein. MMP-9 binding proteins may be antibodies. MMP-9 binding antibodies may have their HC and LC variable domain sequences included in a single polypeptide (e.g., scFv), or on different polypeptides (e.g., IgG or Fab).

The MMP-9 binding protein may be an isolated peptide or protein (e.g., at least 70, 80, 85, 90, 91, 92, 93, 94, 95, 96, 97, 98, or 99% free of other proteins).

The MMP-9 binding protein may additionally inhibit MMP-9, e.g., human MMP-9. The binding protein can inhibit the catalytic activity of MMP-9 (e.g., human MMP-9). In one embodiment, the protein binds the catalytic domain of human MMP-9, e.g., the protein contacts residues in or near the active site of MMP-9. In some embodiments, the protein does not contact residues in or near the active site of MMP-9 but instead binds elsewhere on MMP-9 and causes a steric change in MMP-9 that affects (e.g., inhibits) its activity.

The protein can bind to MMP-9, e.g., human MMP-9, with a binding affinity of at least $10^5$, $10^6$, $10^7$, $10^8$, $10^9$, $10^{10}$ and $10^{11}$ M$^{-1}$. In one embodiment, the protein binds to MMP-9 with a K$_{off}$ slower than $1\times10^{-3}$, $5\times10^{-4}$ s$^{-1}$, or $1\times10^{-4}$ s$^{-1}$. In one embodiment, the protein binds to MMP-12 with a K$_{on}$ faster than $1\times10^2$, $1\times10^3$, or $5\times10^3$ M$^{-1}$ s$^{-1}$. In one embodiment, the protein inhibits human MMP-9 activity, e.g., with a Ki of less than $10^{-5}$, $10^{-6}$, $10^{-7}$, $10^{-8}$, $10^{-9}$, and $10^{-10}$ M. The protein can have, for example, an IC50 of less than 100 nM, 10 nM or 1 nM. In some embodiments, the protein has an IC50 of about 1.8 nM. The affinity of the protein for MMP-9 can be characterized by a K$_D$ of less than 100 nm, less than 10 nM, or about 3 nM (e.g., 3.1 nM), about 5 nM (e.g., 5 nM), about 6 nm (e.g., 5.9 nM), about 7 nM (e.g., 7.1 nM), or about 10 nM (e.g., 9.6 nM).

In some embodiments, the protein has a K$_D$<200 nM.

In some embodiments, the protein has a t½ of at least about 10 minutes (e.g., 11 minutes), at least about 20 minutes (e.g., 18 minutes), at least about 25 minutes (e.g., 25 minutes), at least about 35 minutes (e.g., 33 minutes), or at least about 60 minutes (e.g., 57 minutes).

In one embodiment, the protein binds the catalytic domain of human MMP-9, e.g., the protein contacts residues in or near the active site of MMP-9.

In some embodiments, the protein does not contact residues in or near the active site of MMP-9 but instead binds elsewhere on MMP-9 and causes a steric change in MMP-9 that affects (e.g., inhibits) its activity.

Exemplary MMP-9 binding proteins include antibodies with a heavy chain (HC) and/or light chain (LC), and in some embodiments, an HC and/or LC variable domain, that is selected from the group of antibodies consisting of: 539A-M0240-B03, M0078-G07, M0081-D05, M0076-D03, M0072-H07, M0075-D12, and M0166-F10, or proteins that comprise the HC and/or LC CDRs of 539A-M0240-B03, M0078-G07, M0081-D05, M0076-D03, M0072-H07, M0075-D12, and M0166-F10. These MMP-9 binding proteins are further described in U.S. Ser. No. 61/033,075, filed Mar. 3, 2008 and U.S. Ser. No. 61/054,938, filed May 21, 2008, the content of which applications are hereby incorporated by reference in their entireties. Amino acid sequences for these and additional binding proteins are also provided in FIG. 3 and the Examples herein.

The protein, if an antibody, can include one or more of the following characteristics: (a) a human CDR or human framework region; (b) the HC immunoglobulin variable domain sequence comprises one or more CDRs that are at least 85, 88, 90, 91, 92, 93, 94, 95, 96, 97, 98, 99, or 100% identical to a CDR of a HC variable domain described above; (c) the LC immunoglobulin variable domain sequence comprises one or more CDRs that are at least 85, 88, 90, 91, 92, 93, 94, 95, 96, 97, 98, 99, or 100% identical to a CDR of a LC variable domain described above; (d) the LC immunoglobulin variable domain sequence is at least 85, 88, 90, 91, 92, 93, 94, 95, 96, 97, 98, 99, or 100% identical to a LC variable domain described above; (e) the HC immunoglobulin variable domain sequence is at least 85, 88, 90, 91, 92, 93, 94, 95, 96, 97, 98, 99, or 100% identical to a HC variable domain described above; (f) the protein binds an epitope bound by a protein described herein, or an epitope that overlaps with such epitope; and (g) a primate CDR or primate framework region.

In one embodiment, the HC and LC variable domain sequences are components of the same polypeptide chain. In another, the HC and LC variable domain sequences are components of different polypeptide chains. For example, the protein is an IgG, e.g., IgG1, IgG2, IgG3, or IgG4. The protein can be a soluble Fab (sFab). In other implementations the protein includes a Fab$_2$', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab$_2$, Fab$_2$', scFv, PEGylated Fab, PEGylated scFv, PEGylated Fab$_2$, VH::CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions. In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In certain embodiments, the protein includes no sequences from mice or rabbits (e.g., is not a murine or rabbit antibody).

MMP-9/MMP-2 Binding Proteins

MMP-9/2 binding proteins are binding proteins that bind to MMP-9 (e.g., human MMP-9) and MMP-2 (e.g., human MMP-2) and are either peptides, polypeptides that include at least one immunoglobin variable region, or Kunitz domains. Methods for discovering and selecting and improving such binding proteins are described further below. Both MMP-9 and MMP-2 expression is observed in bone samples from patients with bone-metastatic prostate cancer. An MMP-9/MMP-2 binding protein, e.g., an MMP-9/MMP-2 binding proteins described herein, can be used in the methods described herein, e.g., to treat an osteolytic disorder.

In a preferred embodiment, the MMP-9/2 binding protein includes at least one immunoglobin variable region. For example, the MMP-9/MMP-2 binding protein includes a heavy chain (HC) immunoglobulin variable domain sequence and a light chain (LC) immunoglobulin variable domain sequence. MMP-9/MMP-2 binding proteins may be antibodies. MMP-9/MMP-2 binding antibodies may have their HC and LC variable domain sequences included in a single polypeptide (e.g., scFv), or on different polypeptides (e.g., IgG or Fab).

The MMP-9/MMP-2 binding protein may be an isolated protein (e.g., at least 70, 80, 85, 90, 91, 92, 93, 94, 95, 96, 97, 98, or 99% free of other proteins).

The MMP-9/MMP-2 binding protein may additionally inhibit MMP-9, e.g., human MMP-9 and/or MMP-2, e.g., human MMP-2. The binding protein can inhibit the catalytic activity of MMP-9 (e.g., human MMP-9) and/or MMP-2 (e.g., human MMP-2). In one embodiment, the protein binds the catalytic domain of human MMP-9, e.g., the protein contacts residues in or near the active site of MMP-9 and/or the protein binds the catalytic domain of human MMP-2, e.g., the protein contacts residues in or near the active site of MMP-2. In some embodiments, the protein does not contact residues in or near the active site of MMP-9 but instead binds elsewhere on MMP-9 and causes a steric change in MMP-9 that affects (e.g., inhibits) its activity. In other embodiments, the protein does not contact residues in or near the active site of MMP-2 but instead binds elsewhere on MMP-2 and causes a steric change in MMP-2 that affects (e.g., inhibits) its activity.

The protein can bind to MMP-9 and/or MMP-2 with a binding affinity of at least $10^5$, $10^6$, $10^7$, $10^8$, $10^9$, $10^{10}$ and $10^{11}$ $M^{-1}$. In one embodiment, the protein binds to MMP-9 and/or MMP-2 with a $K_{off}$ slower than $1\times10^{-3}$, $5\times10^{-4}$ $s^{-1}$, or $1\times10^{-4}$ $s^{-1}$. In one embodiment, the protein binds to MMP-12 with a $K_{on}$ faster than $1\times10^2$, $1\times10^3$, or $5\times10^3$ $M^{-1}$ $s^{-1}$. In one embodiment, the protein inhibits human MMP-9 and/or MMP-2 activity, e.g., with a Ki of less than $10^{-5}$, $10^{-6}$, $10^{-7}$, $10^{-8}$, $10^{-9}$, and $10^{-10}$ M. The protein can have, for example, an IC50 of less than 100 nM, 10 nM or 1 nM. In some embodiments, the protein has an IC50 of about 1.8 nM. The affinity of the protein for MMP-9 can be characterized by a $K_D$ of less than 100 nm, less than 10 nM, or about 3 nM (e.g., 3.1 nM), about 5 nM (e.g., 5 nM), about 6 nm (e.g., 5.9 nM), about 7 nM (e.g., 7.1 nM), or about 10 nM (e.g., 9.6 nM).

In some embodiments, the protein has a $K_D$<200 nM.

In some embodiments, the protein has a t½ of at least about 10 minutes (e.g., 11 minutes), at least about 20 minutes (e.g., 18 minutes), at least about 25 minutes (e.g., 25 minutes), at least about 35 minutes (e.g., 33 minutes), or at least about 60 minutes (e.g., 57 minutes).

An exemplary MMP-9/2 binding protein includes an antibody with a heavy chain (HC) and/or light chain (LC), and in some embodiments, an HC and/or LC variable domain, that is selected from the group of antibodies consisting of: M0237-D02. Such MMP-9/2 binding proteins are further described in U.S. Ser. No. 61/033,068, filed on Mar. 3, 2008, U.S. Ser. No. 61/033,075, filed Mar. 3, 2008 and U.S. Ser. No. 61/054,938, filed May 21, 2008, the content of which applications are hereby incorporated by reference in their entireties. Amino acid sequences are also provided in the Examples herein.

In one embodiment, the HC and LC variable domain sequences are components of the same polypeptide chain. In another, the HC and LC variable domain sequences are components of different polypeptide chains. For example, the protein is an IgG, e.g., IgG1, IgG2, IgG3, or IgG4. The protein can be a soluble Fab (sFab). In other implementations the protein includes a Fab$_2$', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab$_2$, Fab$_2$', scFv, PEGylated Fab, PEGylated scFv, PEGylated Fab$_2$, VH::CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions. In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In certain embodiments, the protein includes no sequences from mice or rabbits (e.g., is not a murine or rabbit antibody). Methods for Discovering MMP-14 or MMP-9 Binding Proteins MMP-14 or MMP-9 binding proteins may be discovered by any method of ligand discovery known in the art. In certain embodiments, MMP-14 or MMP-9 binding proteins may be discovered by screening a library. In certain embodiments, the library is a display library. A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of a soluble Fab (sFab). In one exemplary implementation, a display library can be used to identify proteins that bind to MMP-14 or MMP-9. In a selection, the polypeptide component of each member of the library is probed with MMP-14 or MMP-9 (e.g., the catalytic domain of MMP-14 or MMP-9 or other fragment) and if the polypeptide component binds to the MMP-14 or MMP-9, the display library member is identified, typically by retention on a support.

After selecting candidate library members that bind to a target, each candidate library member can be further analyzed, e.g., to further characterize its binding properties for the target, e.g., MMP-14 or MMP-9, or for binding to another protein, e.g., another metalloproteinase. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties include ELISAs, homogenous binding assays, surface plasmon resonance (SPR) and cellular assays, the practice of which are well-known to those of skill in the art.

In addition to the use of display libraries, other methods can be used to obtain a MMP-14 or MMP-9 binding antibody. For example, MMP-14 or MMP-9 protein or a region thereof can be used as an antigen in a non-human animal, e.g., a rodent. Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762. Those methods include isolating, manipulating, and expressing the nucleic acid sequences that encode all or part of immunoglobulin Fv variable regions from at least one of a heavy or light chain. Numerous sources of such nucleic acid are available. For example, nucleic acids may be obtained from a hybridoma producing an antibody against a predetermined target, as described above. The recombinant DNA encoding the humanized antibody, or fragment thereof, can then be cloned into an appropriate expression vector.

Immunoglobin MMP-14 or MMP-9 binding proteins (e.g., IgG or Fab MMP-14 or MMP-9 binding proteins) may be modified to reduce immunogenicity. Reduced immunogenicity is desirable in MMP-14 or MMP-9 binding proteins intended for use as therapeutics, as it reduces the chance that the subject will develop an immune response against the therapeutic molecule. Techniques useful for reducing immunogenicity of MMP-14 or MMP-9 binding proteins include deletion/modification of potential human T-cell epitopes and 'germlining' of sequences outside of the CDRs (e.g., framework and Fc).

An MMP-14 or MMP-9-binding antibody may be modified by specific deletion of human T-cell epitopes or "deimmunization" by the methods disclosed in WO 98/52976 and WO 00/34317. Briefly, the heavy and light chain variable regions of an antibody are analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T-cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al., 1992, *J. Mol. Biol.* 227:776-798; Cook, G. P. et al., 1995, *Immunol. Today* Vol. 16 (5): 237-242; Chothia, D. et al., 1992, *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases a potential T-cell epitope will include residues which are known or predicted to be important for antibody function. For example, potential T-cell epitopes are usually biased towards the CDRs. In addition, potential T-cell epitopes can occur in framework residues important for antibody structure and binding. Changes to eliminate these potential epitopes will in some cases require more scrutiny, e.g., by making and testing chains with and without the change. Where possible, potential T-cell epitopes that overlap the CDRs were eliminated by substitutions outside the CDRs. In some cases, an alteration within a CDR is the only option, and thus variants with and without this substitution should be tested. In other cases, the substitution required to remove a potential T-cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T-cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

MMP-14 or MMP-9 binding antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

Antibodies that bind to MMP-14 or MMP-9, e.g., an antibody described herein, may be modified in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) are then made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity as measured by $K_A$) can be within a factor or 100, 10, 5, 2, 0.5, 0.1, and 0.001 of the original antibody.

Germline sequences of human immunoglobin genes have been determined and are available from a number of sources, including the international IMMUNOGENETICS INFORMATION SYSTEM® (IMGT®), available via the world wide web at imgt.cines.fr, and the V BASE directory (compiled by Tomlinson, L A. et al. MRC Centre for Protein Engineering, Cambridge, UK, available via the world wide web at vbase.mrc-cpe.cam.ac.uk).

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, *EMBO J.* 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

In one embodiment, an MMP-14 or MMP-9 binding protein is physically associated with a moiety that improves its stabilization and/or retention in circulation, e.g., in blood, serum, lymph, or other tissues, e.g., by at least 1.5, 2, 5, 10, or 50 fold. For example, an MMP-14 or MMP-9 binding protein can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an MMP-14 or MMP-9 binding protein can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

An MMP-14 or MMP-9 binding protein can also be associated with a carrier protein, e.g., a serum albumin, such as a human serum albumin. For example, a translational fusion can be used to associate the carrier protein with the MMP-14 or MMP-9 binding protein.

Pharmaceutical Compositions of MMP-14 or MMP-9 Binding Proteins

In another aspect, the disclosure provides compositions, e.g., pharmaceutically acceptable compositions or pharmaceutical compositions, which include an MMP-14 or MMP-9-binding protein, e.g., an antibody molecule, other polypeptide or peptide identified as binding to MMP-14 or MMP-9 described herein. The MMP-14 or MMP-9 binding protein can be formulated together with a pharmaceutically acceptable carrier and/or pharmaceutically acceptable salt. Pharmaceutical compositions include therapeutic compositions and diagnostic compositions, e.g., compositions that include labeled MMP-14 or MMP-9 binding proteins for in vivo imaging.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion), although carriers suitable for inhalation and intranasal administration are also contemplated. Depending on the route of administration, the MMP-14 or MMP-9 binding protein may be coated in a material to protect the compound from the action of acids and other natural conditions that may inactivate the compound.

A pharmaceutically acceptable salt is a salt that retains the desired biological activity of the parent compound and does not impart any undesired toxicological effects (see e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the MMP-14 or MMP-9 binding protein is administered by intravenous infusion or injection. In another preferred embodiment, the MMP-14 or MMP-9 binding protein is administered by intramuscular or subcutaneous injection.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An MMP-14 or MMP-9 binding protein can be administered by a variety of methods, although for many applications, the preferred route/mode of administration is intravenous injection or infusion. For example, for therapeutic applications, the MMP-14 or MMP-9 binding protein can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an MMP-14 or MMP-9 binding protein can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody disclosed herein is 0.1-20 mg/kg, more preferably 1-10 mg/kg. An anti-MMP-14 or MMP-9 antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. For binding proteins smaller in molecular weight than an antibody, appropriate amounts can be proportionally less. Dosage values may vary with the type and severity of the condition to be alleviated. For a particular subject, specific dosage regimens can be adjusted over time according to the individual need and the professional judgment of the person administering or supervising the administration of the compositions.

The pharmaceutical compositions disclosed herein may include a "therapeutically effective amount" or a "prophylactically effective amount" of an MMP-14 or MMP-9 binding protein disclosed herein.

Methods of Treating Osteolytic Disorders

Proteins that bind to MMP-14 or MMP-9 and identified by the method described herein and/or detailed herein have therapeutic and prophylactic utilities, particularly in human subjects. These binding proteins are administered to a subject to treat, prevent, and/or diagnose osteolytic disorders. In certain embodiments, the MMP-14 or MMP-9 binding proteins are administered to a subject, or even to osteotropic cancer cells in culture, e.g. in vitro or ex vivo, to treat or prevent osteotropic cancer. In other embodiments, the MMP-14 or MMP-9 binding proteins are administered to a subject to treat or prevent osteoporosis. Treating includes administering an amount effective to alleviate, relieve, alter, remedy, ameliorate, improve or affect the disorder, at least one symptom of the disorder or the predisposition toward the disorder, whereas preventing includes administering an amount effective to stop or slow the manifestation of the disorder, e.g., as compared to what is expected in the absence of the treatment. The treatment may also delay onset, e.g., prevent onset, or prevent deterioration of the osteolytic disorder, e.g., as compared to what is expected in the absence of the treatment.

As used herein, an amount of a MMP-14 or MMP-9 binding protein effective to prevent an osteolytic disorder, such as osteotropic cancer or osteoporosis, or a prophylactically effective amount of the MMP-14 or MMP-9 binding protein, refers to an amount of a MMP-14 or MMP-9 binding protein, e.g., an anti-MMP-14 or MMP-9 antibody described herein, which is effective, upon single- or multiple-dose administration to the subject, for preventing or delaying the occurrence of the onset or recurrence of the osteolytic disorder. Stated another way, a therapeutically effective amount of an MMP-14 or MMP-9 binding protein is the amount which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition are outweighed by the therapeutically beneficial effects. A therapeutically effective dosage preferably modulates a measurable parameter favorably relative to untreated subjects. The ability of a compound to inhibit a measurable parameter can be evaluated in an animal model system predictive of efficacy in a human disorder. Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Guidance for determination of a therapeutically effective amount for treatment of an osteolytic disorder may be obtained by reference to in vivo models of the particular osteolytic disorder. For example, for osteotropic cancer, the amount of a MMP-14 or MMP-9 binding protein that is a therapeutically effective amount in a rodent or Libechov minipig model of cancer may be used to guide the selection of a dose that is a therapeutically effective amount. A number of rodent models of human cancers are available, including nude mouse/tumor xenograft systems. Cancer cell lines such as PC-3 or the human breast cancer cell line, MDA-MB-231, with either a high potential to cause bone metastasis (MDA-231#16) or a low potential (MDA-MB-231#17), may be used in the preparation of such animal models, or may be used on their own as models.

A MMP-14 or MMP-9 binding protein described herein can be used to reduce an osteolytic disorder in a subject, e.g., to treat an osteotropic cancer (e.g., a solid tumor or lesion, or to kill circulating cancer cells) or osteoporosis (e.g., to reduce the porosity of the bones). The method includes administering the MMP-14 or MMP-9 binding protein to the subject, e.g., in an amount effective to modulate the osteolytic disorder (e.g., for osteotropic cancer, a tumor or lesion size), a symptom of the disorder, or progression of the disorder. The MMP-14 or MMP-9 binding protein may be administered multiple times (e.g., at least two, three, five, or ten times) before a therapeutically effective amount is attained. In one embodiment, the MMP-14 or MMP-9 binding proteins are used to inhibit an activity (e.g., inhibit at least one activity, reduce proliferation, migration, growth or viability) of a cell, e.g., a cancer cell in vivo. The binding proteins can be used by themselves or conjugated to an agent, e.g., a cytotoxic drug, cytotoxin enzyme, or radioisotope. This method includes: administering the binding protein alone or attached to an agent (e.g., a cytotoxic drug), to a subject requiring such treatment. For example, MMP-14 or MMP-9 binding proteins that do not substantially inhibit MMP-14 or MMP-9 may be used to deliver nanoparticles containing agents, such as toxins, to MMP-14 or MMP-9 associated cells or tissues, e.g., tumors.

Accordingly, the disclosure provides methods of treating (e.g., slowing, eliminating, or reversing tumor growth or bone porosity, preventing or reducing, either in number or size, metastases, reducing or eliminating tumor cell invasiveness, providing an increased interval to tumor progression, or increasing disease-free survival time, e.g., relative to a standard, e.g., as compared to what is expected in the absence of treatment or as compared to the condition of a subject (or cohort of subjects) with an osteolytic disorder that was not treated for the disease) an osteolytic disorder such as osteotropic cancer or osteoporosis by administering an effective amount of an MMP-14 or MMP-9 binding protein (e.g., an anti-MMP-14 or MMP-9 IgG or Fab). In some embodiments, the MMP-14 or MMP-9 binding protein inhibits MMP-14 or MMP-9 activity. In certain embodiments, the MMP-14 or MMP-9 binding protein is administered as a single agent treatment. In other embodiments, the MMP-14 or MMP-9 binding protein is administered in combination with an additional anti-cancer agent.

Also provided are methods of preventing or reducing risk of developing an osteolytic disorder, by administering an effective amount of an MMP-14 or MMP-9 binding protein to a subject at risk of developing an osteolytic disorder, thereby reducing the subject's risk of developing the osteolytic disorder. For example, MMP-14 or MMP-9 binding proteins may be administered to prevent osteolytic lesions in a subject having osteotropic cancer, e.g., bone metastasis. As another example, to prevent or reduce the risk of developing an osteolytic disorder, an MMP-14 or MMP-9 binding protein may be administered to a subject who has been diagnosed with a cancer (e.g., breast, lung or prostate cancer) that has the potential to metastasize to bone.

The disclosure further provides methods of modulating (e.g., reducing or preventing) osteotropic cancer at a tumor site by administering an effective amount of an MMP-14 or MMP-9 binding protein, thereby reducing or preventing the tumor size or growth. The MMP-14 or MMP-9 binding protein may be administered to the tumor site as a single agent therapy or in combination with additional agents.

Also provided are methods for reducing extracellular matrix (ECM) degradation by a tumor, comprising administering an effective amount of an MMP-14 or MMP-9 binding protein to a subject, thereby reducing ECM degradation by a tumor in the subject.

Methods of administering MMP-14 or MMP-9 binding proteins and other agents are also described in "Pharmaceutical Compositions." Suitable dosages of the molecules used can depend on the age and weight of the subject and the particular drug used. The binding proteins can be used as competitive agents to inhibit, reduce an undesirable interaction, e.g., between a natural or pathological agent and the MMP-14 or MMP-9. The dose of the MMP-14 or MMP-9 binding protein can be the amount sufficient to block 90%, 95%, 99%, or 99.9% of the activity of MMP-14 or MMP-9 in the patient, especially at the site of disease. Depending on the disease, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

Because the MMP-14 or MMP-9 binding proteins recognize MMP-14 or MMP-9-expressing cells and can bind to cells that are associated with (e.g., in proximity of or intermingled with) osteotropic cancer cells, MMP-14 or MMP-9 binding proteins can be used to inhibit (e.g., inhibit at least one activity, reduce growth and proliferation, or kill) any such cells and inhibit the progression of the osteolytic disorder. Reducing MMP-14 or MMP-9 activity near a cancer can indirectly inhibit (e.g., inhibit at least one activity, reduce growth and proliferation, or kill) the cancer cells which may be dependent on the MMP-14 or MMP-9 activity for metastasis, activation of growth factors, and so forth.

Alternatively, the binding proteins bind to cells in the vicinity of the cancerous cells, but are sufficiently close to the cancerous cells to directly or indirectly inhibit (e.g., inhibit at least one activity, reduce growth and proliferation, or kill) the cancers cells. Thus, the MMP-14 or MMP-9 binding proteins (e.g., modified with a toxin, e.g., a cytotoxin) can be used to selectively inhibit cells in cancerous tissue (including the cancerous cells themselves and cells associated with or invading the cancer).

The MMP-14 or MMP-9 binding proteins may be used to deliver or aid or enhance the delivery of an agent (e.g., any of a variety of cytotoxic and therapeutic drugs) to cells and tissues where MMP-14 or MMP-9 is present. Exemplary agents include a compound emitting radiation, molecules of plants, fungal, or bacterial origin, biological proteins, and mixtures thereof. The cytotoxic drugs can be intracellularly acting cytotoxic drugs, such as toxins or short range radiation emitters, e.g., short range, high energy α-emitters.

To target MMP-14 or MMP-9 expressing osteotropic cancer cells, a prodrug system can be used. For example, a first binding protein is conjugated with a prodrug which is activated only when in close proximity with a prodrug activator. The prodrug activator is conjugated with a second binding protein, preferably one which binds to a non competing site on the target molecule. Whether two binding proteins bind to competing or non competing binding sites can be determined by conventional competitive binding assays. Exemplary drug prodrug pairs are described in Blakely et al., (1996) Cancer Research, 56:3287 3292.

The MMP-14 or MMP-9 binding proteins can be used directly in vivo to eliminate antigen-expressing cells via natural complement-dependent cytotoxicity (CDC) or antibody dependent cellular cytotoxicity (ADCC). The binding proteins described herein can include a complement binding effector domain, such as the Fc portions from IgG1, -2, or -3 or corresponding portions of IgM which bind complement. In one embodiment, a population of target cells is ex vivo treated with a binding agent described herein and appropriate effector cells. The treatment can be supplemented by the addition of complement or serum containing complement. Further, phagocytosis of target cells coated with a binding protein described herein can be improved by binding of complement proteins. In another embodiment, target cells coated with the binding protein which includes a complement binding effector domain are lysed by complement.

The MMP-14 or MMP-9 binding protein can be used to deliver macro and micromolecules, e.g., a gene into the cell for gene therapy purposes into the endothelium or epithelium and target only those tissues expressing the MMP-14 or MMP-9.

In the case of polypeptide toxins, recombinant nucleic acid techniques can be used to construct a nucleic acid that encodes the binding protein (e.g., antibody or antigen-binding fragment thereof) and the cytotoxin (or a polypeptide component thereof) as translational fusions. The recombinant nucleic acid is then expressed, e.g., in cells and the encoded fusion polypeptide isolated.

Alternatively, the MMP-14 or MMP-9 binding protein can be coupled to high energy radiation emitters, for example, a radioisotope, such as $^{131}$I, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, $^{213}$Bi, and $^{211}$At, and b emitters, such as $^{186}$Re and $^{90}$Y. Moreover, $^{177}$Lu may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Combination Therapies

The MMP-14 or MMP-9 binding proteins described herein, e.g., anti-MMP-14 or MMP-9 Fabs or IgGs, can be administered in combination with one or more of the other therapies for treating the particular osteolytic disorder of interest. For example, an MMP-14 or MMP-9 binding protein can be used therapeutically or prophylactically with surgery, another MMP-14 or MMP-9 inhibitor, e.g., a small molecule inhibitor, another anti-MMP-14 or MMP-9 Fab or IgG (e.g., another Fab or IgG described herein), peptide inhibitor, or small molecule inhibitor. Examples of MMP-14 or MMP-9 inhibitors that can be used in combination therapy with an MMP-14 or MMP-9 binding protein described herein include neovastat, marimastat, BAY 12-9566 and prinomastat. One or more small-molecule MMP inhibitors can be used in combination with one or more MMP-14 or MMP-9 binding proteins described herein. For example, the combination can result in a lower dose of the small-molecule inhibitor being needed, such that side effects are reduced. The combination may result in enhanced delivery and efficacy of one or both agents.

In certain embodiments, the MMP-14 or MMP-9 binding proteins described herein can be administered in combination with one or more of the other therapies for treating osteotropic cancer, including, but not limited to: surgery; radiation therapy, chemotherapy, and other anti-cancer therapeutic agents. For example, proteins that inhibit MMP-14 or MMP-9 or that inhibit a downstream event of MMP-14 or MMP-9 activity (e.g., cleavage of pro-MMP-2 to MMP-2) can also be used in combination with other anti-cancer therapies, such as radiation therapy, chemotherapy, surgery, or administration of a second agent. For example, the second agent can be a Tie-1 inhibitor (e.g., Tie-1 binding proteins; see e.g., U.S. Ser. No. 11/199,739 and PCT/US2005/0284, both filed Aug. 9, 2005). As another example, the second agent can be one that targets or negatively regulates the VEGF signaling pathway. Examples of this latter class include VEGF antagonists (e.g., anti-VEGF antibodies such as bevacizumab) and VEGF receptor antagonists (e.g., anti-VEGF receptor antibodies). One particularly preferred combination includes bevacizumab. The combination can further include 5-FU and leucovorin, and/or irinotecan. Other additional cancer therapeutic or treatments, include bisphosphonates (e.g., amino and non-amino bisphosphonates), hormone-related compounds (e.g., estrogens and SERMs), RANKL antagonists, RANKL pathway inhibitors, $\alpha_v\beta_3$ antagonists, Src inhibitors, cathepsin K inhibitors and calcitonin.

In other embodiments, the MMP-14 or MMP-9 binding proteins described herein can be administered in combination with one or more of the other therapies for treating osteoporosis, including, but not limited to, bisphosphonates (e.g., amino and non-amino bisphosphonates), hormone-related compounds (e.g., estrogens and SERMs), calcitonin, Teriparatide (FORTEO™), tamoxifen and RANKL pathway inhibitors.

The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of an MMP-14 or MMP-9 binding protein described herein can also be used to reduce the dosage of another therapy, e.g., to reduce the side-effects associated with another agent that is being administered, e.g., to reduce the side-effects of an anti-VEGF antibody such as bevacizumab. Accordingly, a combination can include administering a second agent at a dosage at least 10, 20, 30, or 50% lower than would be used in the absence of the MMP-14 or MMP-9 binding protein.

The second agent or therapy can also be another anti-cancer agent or therapy. Non-limiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5 fluorouracil (5 FU), methotrexate, 6 mercaptopurine, 6 thioguanine, fludarabine phosphate, cytarabine/Ara C, trimetrexate, gemcitabine, acivicin, alanosine, pyrazofurin, N-Phosphoracetyl-L-Asparate=PALA, pentostatin, 5 azacitidine, 5 Aza 2' deoxycytidine, ara A, cladribine, 5 fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4 ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example anti-androgens such as 4'-cyano-3-(4-fluorophenylsulphonyl)-2-hydroxy-2-methyl-3'-(trifluoromethyl) propionanilide.

Other additional cancer therapeutic or treatments that may be used in treating metastatic bone cancers include bisphosphonates (e.g., amino and non-amino bisphosphonates), hormone-related compounds (e.g., estrogens and SERMs), RANKL antagonists, $\alpha_v\beta_3$ antagonists, Src inhibitors, cathepsin K inhibitors and calcitonin. All of these therapeutics may serve as bone resorption inhibitors, in addition to having other activities.

Bisphosphonates (also called: diphosphonates) are a class of drugs that inhibits osteoclast action and the resorption of bone. Their uses include the prevention and treatment of osteoporosis, osteitis deformans ("Paget's disease of bone"), bone metastasis (with or without hypercalcemia), multiple myeloma and other conditions that feature bone fragility. Exemplary bisphosphonates (also known as diphosphonates) include both amino and non-amino bisphosphonates. Specific examples of bisphosphonates that may be used in the disclosed methods include, but are not limited to, non-amino bisphosphonates such as Etidronate (DIDRONEL®), Clodronate (BONEFOS®, LORON®) and Tiludronate (SKELID®); and amino bisphosphonates such as Pamidronate (APD, AREDIA®), Neridronate, Olpadronate, Alendronate (FOSAMAX®), Ibandronate (BONIVA®), Risedronate (ACTONEL®) and Zoledronate (ZOMETA®).

Hormone-related compounds include, but are not limited to, estrogens, selective estrogen receptor modulators (SERMs) and LH-RH agonists such as Leuprolide (LUPRON®, VIADUR®, ELIGARD®), Goserelin (Zoladex®), Raloxifene (EVISTA®) and Triptorelin (TRELSTAR®).

RANKL antagonists may be used to block RANK-RANKL interactions. Exemplary RANKL antagonists include, but are not limited to, TRANCE-Fc, OPG and OPG-Fc.

Exemplary RANKL pathway inhibitors include, but are not limited to, Denosumab (Body, et al. (2006) Clin. Cancer Res. 12:1221-1228).

$\alpha_v\beta_3$ antagonists may be used to block osteoclast adhesion to bone. Exemplary $\alpha_v\beta_3$ antagonists include small molecule and peptide antagonists, examples of which include but are not limited to, Vitaxin, Cilengitide, (S)-3-Oxo-8-[2-[6-(methylamino)-pyridin-2-yl]-1-ethoxy]-2-(2,2,2-trifluoroethyl)-2,3,4,5-tetrahydro-1H-2-benzazepine-4-acetic acid and 3-[2-oxo-3-[3-(5,6,7,8-tetrahydro-[1,8]naphthyridin-2-yl) propyl]-imidazolidin-1-yl]-3(S)-(6-methoxy-pyridin-3-yl) propionic acid.

Src inhibitors may be used to block steps leading to osteoclast activation. Exemplary Src inhibitors include, but are not limited to, SKI-606 (WYETH™), AZD0530 (ASTRAZENECA™) and BMS-453825 (Dasatinib (SPRYCEL®)).

Cathepsin K inhibitors may be used to block activity of osteoclast-specific collagenase. Exemplary cathepsin K inhibitors include, but are not limited to, balicatib.

A combination therapy can include administering an agent that reduces the side effects of other therapies. In embodiments where the osteolytic disorder is osteotropic cancer, the agent can be an agent that reduces the side effects of anticancer treatments. For example, the agent can be leucovorin.

Kits

An MMP-14 or MMP-9 binding protein described herein can be provided in a kit, e.g., as a component of a kit. For example, the kit includes (a) an MMP-14 or MMP-9 binding protein, e.g., a composition that includes an MMP-14 or MMP-9 binding protein, and, optionally (b) informational material. The informational material can be descriptive, instructional, marketing or other material that relates to the methods described herein and/or the use of an MMP-14 or MMP-9 binding protein for the methods described herein.

The informational material of the kits is not limited in its form. In one embodiment, the informational material can include information about production of the compound, molecular weight of the compound, concentration, date of expiration, batch or production site information, and so forth.

In one embodiment, the informational material relates to using the binding protein to treat, prevent, or diagnose an osteolytic disorder.

In one embodiment, the informational material can include instructions to administer an MMP-14 or MMP-9 binding protein in a suitable manner to perform the methods described herein, e.g., in a suitable dose, dosage form, or mode of administration (e.g., a dose, dosage form, or mode of administration described herein). In another embodiment, the informational material can include instructions to administer an MMP-14 or MMP-9 binding protein to a suitable subject, e.g., a human, e.g., a human having, or at risk for, an osteolytic disorder. For example, the material can include instructions to administer an MMP-14 or MMP-9 binding protein to a patient with osteotropic cancer or osteoporosis. The informational material of the kits is not limited in its form. In many cases, the informational material, e.g., instructions, is provided in print but may also be in other formats, such as computer readable material.

An MMP-14 or MMP-9 binding protein can be provided in any form, e.g., liquid, dried or lyophilized form. It is preferred that an MMP-14 or MMP-9 binding protein be substantially pure and/or sterile. When an MMP-14 or MMP-9 binding protein is provided in a liquid solution, the liquid solution preferably is an aqueous solution, with a sterile aqueous solution being preferred. When an MMP-14 or MMP-9 binding protein is provided as a dried form, reconstitution generally is by the addition of a suitable solvent. The solvent, e.g., sterile water or buffer, can optionally be provided in the kit.

The kit can include one or more containers for the composition containing an MMP-14 or MMP-9 binding protein. In some embodiments, the kit contains separate containers, dividers or compartments for the composition and informational material. For example, the composition can be contained in a bottle, vial, or syringe, and the informational material can be contained in association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an MMP-14 or MMP-9 binding protein. For example, the kit includes a plurality of syringes, ampules, foil packets, or blister packs, each containing a single unit dose of an MMP-14 or MMP-9 binding protein. The containers of the kits can be air tight, waterproof (e.g., impermeable to changes in moisture or evaporation), and/or light-tight.

The kit optionally includes a device suitable for administration of the composition, e.g., a syringe, inhalant, dropper (e.g., eye dropper), swab (e.g., a cotton swab or wooden swab), or any such delivery device. In one embodiment, the device is an implantable device that dispenses metered doses of the binding protein. The disclosure also features a method of providing a kit, e.g., by combining components described herein.

EXEMPLIFICATIONS

The following examples provide further illustration and are not limiting.

Example 1

DX-2400 Reduces Osteolytic Lesions in the PC-3 Prostate Cancer Model

PC-3 prostate cancer cells were inoculated intra-tibially into mice. Treatment was initiated 3 days after intra-tibial inoculation of the cells. DX-2400 (10 mg/kg) and a PBS control were administered Q2D for 14 days. X-ray analysis and bone histomorphometric analysis indicated that DX-2400 reduced the area of the osteolytic lesions about 3-fold (FIG. 2). DX-2400 is a selective inhibitor of MMP-14.

Example 2

Exemplary MMP-9 Binding Antibodies

Experiments were performed to evaluate the in vitro effects of 539A-M0240-B03 and 539A-M0237-D02 in bone metastasis models.

Cells. Raw 264.7 cells (Mouse leukemia monocyte/macrophage cell line) were obtained from ATCC (Catalog #TIB-71) and maintained in ATCC recommended complete medium (Catalog #30-2020). Cells between passage 3-7 were used in this study.

Materials. Osteologic discs were purchased from BD biosciences (Catalog #354609). Tartrate-resistant acid phosphatase (TRAP) staining kit was obtained from KAMIYA BIOMEDICA COMPANY™, Seattle Wash. (Catalog #KT-008). GM6001 was obtained from MILLIPORE™.

Methods. Approximately 2000 Raw 264.7 cells per slide were seeded onto osteologic multitest slides with complete growth medium. On the following day, cells were replaced with fresh medium containing 100 ng/ml recombinant murine soluble RANK ligand (PEPROTECH INC. UK) along with the broad spectrum MMP inhibitor GM6001 (5 µM, 10 µM, 25 µM concentrations tested), 539A-M0240-B03 (10 µg/ml, 50 µg/ml concentrations tested), or 539A-M0237-D02 (10 µg/ml, 100 µg/ml concentrations tested). The slides were then incubated at 37° C. for 6 days, replacing fresh media on day 3 as described above. At the end of incubation time, one side of the slide was stained for TRAP and the other side of the slide was bleached (10% bleach), washed several times with water, and air dried. The slides were then viewed under the microscope for either multinucleated TRAP positive cells or resorbed areas (pits). Cells incubated with media only and recombinant osteoprotegerin (rH OPG) (100 ng/ml) served as negative and positive controls, respectively.

Conclusion. These in vitro experiments suggest that GM6001, 539A-M0240-B03, and 539A-M0237D02 have inhibitory effects on osteoclastogenesis and bone resorption at the concentrations tested (data not shown). The results showed that the inhibitory effect was dose-dependent. As the concentration of GM6001, 539A-M0240-B03, or 539A-M0237D02 increased, the amount of TRAP-positive staining and the number of resorbed areas decreased.

Example 3

Exemplary MMP-9 Binding Antibodies

539A-M0166-F10. An exemplary MMP-9 antibody is 539A-M0166-F10. The amino acid sequences of variable regions of 539A-M0166-F10 sFAB are as follows:

```
539A-M0166-F10 (phage/SFAB) VL leader + VL
                                    (SEQ ID NO: 12)
FYSHSAQSELTQPPSASAAPGQRVTILSCSGSSSNIGSNTVTWYQKLPGT

APKLLIYNNYERPSGVPARFSGSKSGTSASLAISGLQSEDEADYYCATWD

DSLIANYVFGSGTKVTVLGQPKANP

539A-M0166-F10 (phage/SFAB) VH leader + VH
```

```
                                                        (SEQ ID NO: 13)
MKKLLFAIPLVVPFVAQPAMAEVQLLESGGGLVQPGGSLRLSCAASGFTF

SPYLMNWVRQAPGKGLEWVSSIYSSGGGTGYADSVKGRFTISRDNSKNTL

YLQMNSLRAEDTAVYYCARIYHSSSGPFYGMDVWGQGTTVTVSSASTKGP

SVFPLAPSSKS
```

539A-M0240-B03. Another exemplary MMP-9 antibody is 539A-M0240-B03. 539A-M0240-B03 is a selective inhibitor of MMP-9. 539A-M0240-B03 can decrease or inhibit the activity of human and mouse MMP-9. The sequences of the complementarity determining regions (CDRs) of 539A-M0240-B03 light chain (LC) and heavy chain (HC) are as follows:

```
    LC CDR1: TGTSSDVGGYNYVS          (SEQ ID NO: 14)
    LC CDR2: DVSKRPS                 (SEQ ID NO: 15)
    LC CDR3: CSYAGSYTLV              (SEQ ID NO: 16)
    HC CDR1: TYQMV                   (SEQ ID NO: 17)
    HC CDR2: VIYPSGGPTVYADSVKG       (SEQ ID NO: 18)
    HC CDR3: GEDYYDSSGPGAFDI         (SEQ ID NO: 19)
```

Example 4

Exemplary MMP-9/2 Binding Antibody

M0237-D02. An exemplary MMP-9/2 antibody is M0237-D02. The amino acid sequences of variable regions of 539A-M0237-D02 sFAB are as follows:

```
539A-M0237-D02 (phage/SFAB) VL leader + VL
                                                        (SEQ ID NO: 20)
FYSHSAQDIQMTQSPATLSLSPGERATLSCRASQSISSFLAWYQQKPGQA

PRLLIYDASYRATGIPARFSGSGSGTDPTLTISSLEPEDYAVYYCQQRGN

WPITFGQGTRLEIKRTVAAPS

539A-M0237-D02 (phage/SFAB) VH leader + VH
                                                        (SEQ ID NO: 21)
MKKLLFAIPLVVPFVAQPAMAEVQLLESGGGLVQPGGSLRLSCAASGFTF

SQYPMWWVRQAPGKGLEWVSYIVPSGGRTYYADSVKGRFTISRDNSKNTL

YLQMNSLRAEDTAVYYCAKDRAYGDYVGWNGFDYWGQGTLVTVSSASTKG

PSVFPLAPSSKS
```

Example 5

Exemplary MMP-14 Binding Antibodies

DX-2400. An exemplary MMP-14 antibody is DX-2400. The variable domain sequences for DX-2400 are:

```
VH:
                                                        (SEQ ID NO: 22)
DX-2400 FR1------------------------- CDR1- FR2----------- CDR2-------
        EVQLLESGGGLVQPGGSLRLSCAASGFTFS LYSMN WVRQAPGKGLEWVS SIYSSGGSTLY

DX-2400 CDR2-- FR3---------------------------- CDR3-- FR4---------
        ADSVKG RFTISRDNSKNTLYLQMNSLRAEDTAVYYCAR GRAFDI WGQGTMVTVSS

CDR regions are in bold.

VL:
                                                        (SEQ ID NO: 23)
DX-2400 FR1-------------------- CDR1------- FR2------------ CDR2---
        DIQMTQSPSSLSASVGDRVTITC RASQSVGTYLN WYQQKPGKAPKLLIY ATSNLRS GVPS

DX-2400 FR3------------------------- CDR3------ FR4-------
        RFSGSGSGTDFTLTISSLQPEDFATYYC QQSYSIPRFT FGPGTKVDIK

CDR regions are in bold.
```

DX-2410. Another exemplary MMP-14 antibody is DX-2410. The variable domain sequences for DX-2410 are:

```
VH:
                                                        (SEQ ID NO: 24)
DX2410 FR1------------------------- CDR1- FR2----------- CDR2-------
       EVQLLESGGGLVQPGGSLRLSCAASGFTFS VYGMV WVRQAPGKGLEWVS VISSSGGSTWY

DX2410 CDR2-- FR3---------------------------- CDR3------- FR4--------
       ADSVKG RFTISRDNSKNTLYLQMNSLRAEDTAVYYCAR PFSRRYGVFDY WGQGTLVTVSS

CDR regions are in bold.

VL:
                                                        (SEQ ID NO: 25)
DX2410 FR1-------------------- CDR1------- FR2------------ CDR2---
       DIQMTQSPSSLSASVGDRVTITC RASQGIRNFLA WYQQKPGKVPKLLIY GASALQS

DX2410 FR3--------------------------- CDR3----- FR4-------
       GVPSRFSGSGSGTDFTLTISSLQPEDVATYYC QKYNGVPLT FGGGTKVEIK

CDR regions are in bold.
```

Example 6

Additional Exemplary MMP-9 Binding Antibodies

A protein containing the HC CDR sequences of 539A-M0240-B03 and the light chain sequence shown below can be used in the methods described herein. A protein containing the LC CDRs shown below and the HC CDRs of 539A-M0240-B03, or a protein containing the LC variable region (light V gene) shown below and the 539A-M0240-B03 HC CDRs can also be used in the methods described herein. The protein can include a constant region sequence, such as the constant region (LC-lambda1) shown below.

```
Light V gene = VL2_2e; J gene = JL3
                                                    (SEQ ID NO: 26)
      FR1-L                CDR1-L              FR2-L
QSALTQPRSVSGSPGQSVTISC TGTSSDVGGYNYVS WYQQHPGKAPKL

CDR2-L              FR3-L
MIY DVSKRPS GVPD RFSGSKSGNTASLTISGLQAEDEADYYC

CDR3-L        FR4-L
CSYAGSYTLV FGGGTKLTVL

-------------------

LC-lambda1
                                                    (SEQ ID NO: 27)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTECS
```

CDR regions are in bold.

The amino acid and nucleic acid sequences for another exemplary protein that can be used in the methods described herein are provided below. A protein containing the LC and HC CDRs shown below, or a protein containing the light chain and heavy chain variable regions (LV and HV, respectively) shown below can also be used in the methods described herein.

---

Light Chain

```
Light V gene = VL2_2e 2e.2.2/V1-3/DPL12
Light J gene = JL3

FR1-L                CDR1-L              FR2-L          CDR2-L
Antibody A: QYELTQPRSVSGSPGQSVTISC TGTSSDVGGYNYVS WYQQHPGKAPKLMIY DVSKRPS GVPD FR3-L                      CDR3-L        FR4-L                (SEQ ID NO: 28)
Antibody A: RFSGSKSGNTASLTISGLQAEDEADYYC CSYAGSYTLV FGGGTKLTVL
```

Heavy Chain

```
Heavy V gene: VH3_3-23 DP-47/V3-23
Heavy J gene: JH3

FR1-H                       CDR1-H    FR2-H           CDR2-H
Antibody A: EVQLLESGGGLVQPGGSLRLSCAASGFTFS TYQMV WVRQAPGKGLEWVS VIYPSGGPTVYADSVKG FR3-H                            CDR3-H           FR4-H       (SEQ ID NO: 29)
Antibody A: RFTISRDNSKNTLYLQMNSLRAEDTAVYYCAR GEDYYDSSGPGAFDI WGQGTMVTVSS
```

Light Variable

```
Antibody A-Light: Parental clone (sFab; IgG in pBh1(f)) light variable

Q   Y   E   L   T   Q   P   R   S   V   S   G   S   P   G   Q   S   V   T   I
Antibody A: CAGTACGAATTGACTCAGCCTCGCTCAGTGTCCGGGTCTCCTGGACAGTCAGTCACCATC
              S   C   T   G   T   S   S   D   V   G   G   Y   N   Y   V   S   W   Y   Q   Q
Antibody A: TCCTGCACTGGAACCAGCAGTGATGTTGGTGGTTATAACTATGTCTCCTGGTACCAACAG
              H   P   G   K   A   P   K   L   M   I   Y   D   V   S   K   R   P   S   G   V
Antibody A: CACCCAGGCAAAGCCCCCAAACTCATGATTTATGATGTCAGTAAGCGGCCCTCAGGGGTC
              P   D   R   F   S   G   S   K   S   G   N   T   A   S   L   T   I   S   G   L
Antibody A: CCTGATCGCTTCTCTGGCTCCAAGTCTGGCAACACGGCCTCCCTGACCATCTCTGGGCTC
              Q   A   E   D   E   A   D   Y   Y   C   C   S   Y   A   G   S   Y   T   L   V
Antibody A: CAGGCTGAGGATGAGGCTGATTATTACTGCTGCTCATATGCAGGCAGCTACACTTTGGTG F   G   G   G   T   K   L   T   V   L                        (SEQ ID NO: 30)
Antibody A: TTCGGCGGAGGGACCAAGCTGACCGTCCTA                                  (SEQ ID NO: 31)
```

Heavy Variable

-continued

```
Antibody A-Heavy: Parental clone (sFab; IgG in pBh1(f)) Heavy variable

E   V   Q   L   L   E   S   G   G   G   L   V   Q   P   G   G   S   L   R   L
Antibody A: GAAGTTCAATTGTTAGAGTCTGGTGGCGGTCTTGTTCAGCCTGGTGGTTCTTTACGTCTT
            S   C   A   A   S   G   F   T   F   S   T   Y   Q   M   V   W   V   R   Q   A
Antibody A: TCTTGCGCTGCTTCCGGATTCACTTTCTCTACTTACCAGATGGTTTGGGTTCGCCAAGCT
            P   G   K   G   L   E   W   V   S   V   I   Y   P   S   G   G   P   T   V   Y
Antibody A: CCTGGTAAAGGTTTGGAGTGGGTTTCTGTTATCTATCCTTCTGGTGGCCCTACTGTTTAT
            A   D   S   V   K   G   R   F   T   I   S   R   D   N   S   K   N   T   L   Y
Antibody A: GCTGACTCCGTTAAAGGTCGCTTCACTATCTCTAGAGACAACTCTAAGAATACTCTCTAC
            L   Q   M   N   S   L   R   A   E   D   T   A   V   Y   Y   C   A   R   G   E
Antibody A: TTGCAGATGAACAGCTTAAGGGCTGAGGACACGGCCGTGTATTACTGTGCGAGAGGGGAG
            D   Y   Y   D   S   S   G   P   G   A   F   D   I   W   G   Q   G   T   M   V   T   V   S   S    (SEQ ID NO: 32)
Antibody A: GACTACTATGATAGTAGTGGCCCGGGGGCTTTTGATATCTGGGGCCAAGGGACAATGTGCACCGTCTCAAGC    (SEQ ID NO: 33)
```

The amino acid and nucleic acid sequences for another exemplary protein that can be used in the methods described herein are provided below. A protein containing the LC and HC CDRs shown below, or a protein containing the light chain and heavy chain variable regions (LV and HV, respectively) shown below can also be used in the methods described herein. A protein containing the light chain and heavy chain (designated as LV+LC and HV+HC, respectively, below) sequences can also be used.

```
Light Chain

Light V gene = VL2_2e 2e.2.2/V1-3/DPL12
Light J gene = JL3

FR1-L                       CDR1-L          FR2-L              CDR2-L
Antibody B: QSALTQPRSVSGSPGQSVTISC  TGTSSDVGGYNYVS  WYQQHPGKAPKLMIY  DVSKRPS  GVPD FR3-L                      CDR3-L       FR4-L                                   (SEQ ID NO: 34)
Antibody B: RFSGSKSGNTASLTISGLQAEDEADYYC  CSYAGSYTLV  FGGGTKLTVL Heavy Chain Heavy V gene: VH3_3-23 DP-47/V3-23
Heavy J gene: JH3

FR1-H                     CDR1-H   FR2-H             CDR2-H
Antibody B: EVQLLESGGGLVQPGGSLRLSCAASGFTFS  TYQMV  WVRQAPGKGLEWVS  VIYPSGGPTVYADSVKG FR3-H                        CDR3-H              FR4-H                         (SEQ ID NO: 35)
Antibody B: RFTISRDNSKNTLYLQMNSLRAEDTAVYYCAR  GEDYYDSSGPGAFDI  WGQGTMVTVSS Light Variable Antibody B-Light: Germlined, codon optimized in GS vector Antibody B: CAGAGCGCCCTGACCCAGCCCAGAAGCGTGTCCGGCAGCCCAGGCCAGAGCGTGACCATC
             Q  S  A  L  T  Q  P  R  S  V  S  G  S  P  G  Q  S  V  T  I
Antibody B: AGCTGCACCGGCACCAGCAGCGACGTGGGCGGCTACAACTACGTGTCCTGGTATCAGCAG
             S  C  T  G  T  S  S  D  V  G  G  Y  N  Y  V  S  W  Y  Q  Q
Antibody B: CACCCCGGCAAGGCCCCCAAGCTGATGATCTACGACGTGTCCAAGAGGCCCAGCGGCGTG
             H  P  G  K  A  P  K  L  M  I  Y  D  V  S  K  R  P  S  G  V
Antibody B: CCCGACAGGTTCAGCGGCAGCAAGAGCGGCAACACCGCCAGCCTGACCATCTCCGGACTG
             P  D  R  F  S  G  S  K  S  G  N  T  A  S  L  T  I  S  G  L
Antibody B: CAGGCCGAGGACGAGGCCGACTACTACTGCTGCAGCTACGCCGGCAGCTACACCCTGGTG
             Q  A  E  D  E  A  D  Y  Y  C  C  S  Y  A  G  S  Y  T  L  V
Antibody B: TTCGGCGGAGGGACCAAGCTGACCGTGCTG                                        (SEQ ID NO: 36)
             F  G  G  G  T  K  L  T  V  L                                       (SEQ ID NO: 37)

Heavy Variable
```

-continued

Antibody B-Heavy: Germlined, codon optimized in GS vector

```
Antibody B: GAGGTGCAATTGCTGGAAAGCGGCGGAGGACTGGTGCAGCCAGGCGGCAGCCTGAGGCTG
             E   V   Q   L   L   E   S   G   G   G   L   V   Q   P   G   G   S   L   R   L
Antibody B: TCCTGCGCCGCCAGCGGCTTCACCTTCAGCACCTACCAGATGGTGTGGGTGCGCCAGGCC
             S   C   A   A   S   G   F   T   F   S   T   Y   Q   M   V   W   V   R   Q   A
Antibody B: CCAGGCAAGGGCCTGGAATGGGTGTCCGTGATCTACCCCAGCGGCGGACCCACCGTGTAC
             P   G   K   G   L   E   W   V   S   V   I   Y   P   S   G   G   P   T   V   Y
Antibody B: GCCGACAGCGTGAAGGGCAGGTTCACCATCAGCAGGGACAACAGCAAGAACACCCTGTAC
             A   D   S   V   K   G   R   F   T   I   S   R   D   N   S   K   N   T   L   Y
Antibody B: CTGCAGATGAACAGCCTGAGGGCCGAGGACACCGCCGTGTACTACTGCGCCAGGGGCGAG
             L   Q   M   N   S   L   R   A   E   D   T   A   V   Y   Y   C   A   R   G   E Antibody B: GACTACTACGACAGCAGCGGCCCAGGCGCCTTCGACATCTGGGGCCAGGGCACAATGGTGACCGTGTCCAGC    (SEQ ID NO: 38)
             D   Y   Y   D   S   S   G   P   G   A   F   D   I   W   G   Q   G   T   M   V   T   V   S   S       (SEQ ID NO: 39)
```

>Antibody B: LV + LC dna (SEQ ID NO: 40)
```
CAGAGCGCCCTCACCCAGCCCAGAAGCGTGTCCGGCAGCCCAGGCCAGAGCGTGACCATCAGCTGCACCGGCACCAGCAGCGACGTGGGCGGCTACAACTAC
GTGTCCTGGTATCAGCAGCACCCCGGCAAGGCCCCCAAGCTGATGATCTACGACGTGTCCAAGAGGCCCAGCGGCGTGCCCGACAGGTTCAGCGGCAGCAAG
AGCGGCAACACCGCCAGCCTGACCATCTCCGGACTGCAGGCCGAGGACGAGGCCGACTACTACTGCTGCAGCTACGCCGGCAGCTACACCCTGGTGTTCGGC
GGAGGGACCAAGCTGACCGTGCTGGGCCAGCCCAAGGCTGCCCCCAGCGTGACCCTGTTCCCCCCCAGCAGCGAGGAACTGCAGGCCAACAAGGCCACACTG
GTGTGCCTGATCAGCGACTTCTACCCAGGCGCCGTGACCGTGGCCTGGAAGGCCGACAGCAGCCCCGTGAAGGCCGGCGTGGAGACAACCACCCCCAGCAAG
CAGAGCAACAACAAGTACGCCGCCAGCAGCTACCTGAGCCTGACCCCCGAGCAGTGGAAGTCCCACAGGTCCTACAGCTGCCAGGTGACCCACGAGGGCAGC
ACCGTGGAGAAAACCGTGGCCCCCACCGAGTGTAGCTGATGA
```
> Antibody B: HV + HC dna (SEQ ID NO: 41)
```
GAGGTGCAATTGCTGGAAAGCGGCGGAGGACTGGTGCAGCCAGGCGGCAGCCTGAGGCTGTCCTGCGCCGCCAGCGGCTTCACCTTCAGCACCTACCAGATG
GTGTGGGTGCGCCAGGCCCCAGGCAAGGGCCTGGAATGGGTGTCCGTGATCTACCCCAGCGGCGGACCCACCGTGTACGCCGACAGCGTGAAGGGCAGGTTC
ACCATCAGCAGGGACAACAGCAAGAACACCCTGTACCTGCAGATGAACAGCCTGAGGGCCGAGGACACCGCCGTGTACTACTGCGCCAGGGGCGAGGACTAC
TACGACAGCAGCGGCCCAGGCGCCTTCGACATCTGGGGCCAGGGCACAATGGTGACCGTGTCCAGCGCTAGCACCAAGGGCCCAGCGGTGTTCCCGCTAGCA
CCTTCCTCCAAGTCCACCTCTGGCGGCACCGCCGCTCTGGGCTGCCTGGTGAAGGACTACTTCCCTGAGCCTGTGACCGTGAGCTGGAACTCTGGCGCCCTG
ACCTCCGGCGTGCATACCTTCCCTGCCGTGCTGCAGTCCTCCGGCCTGTACTCCCTGTCCTCCGTGGTGACAGTGCCTTCCTCCTCCCTGGGCACCCAGACC
TACATCTGCAACGTGAACCACAAGCCTTCCAACACCAAGGTGGACAAGCGGGTGGAGCCTAAGTCCTGCGACAAGACCCACACCTGCCCTCCCTGCCCTGCC
CCTGAGCTGCTGGGCGGACCCTCCGTGTTCCTGTTCCCTCCTAAGCCTAAGGACACCCTGATGATCTCCCGGACCCCTGAGGTGACCTGCGTGGTGGTGGAC
GTGTCCCACGAGGACCCAGAGGTGAAGTTTAATTGGTATGTGGACGGCGTGGAGGTCCACAACGCCAAGACCAAGCCTCGGGAGGAACAGTACAACTCCACC
TACCGGGTGGTGTCCGTGCTGACCGTGCTGCACCAGGACTGGCTGAACGGCAAGGAATACAAGTGCAAAGTCTCCAACAAGGCCCTGCCTGCCCCCATCGAG
AAAACCATCTCCAAGGCCAAGGGCCAGCCTCGCGAGCCTCAGGTGTACACCCTGCCTCCTAGCCGGGAGGAAATGACCAAGAACCAGGTGTCCCTGACCTGT
CTGGTGAAGGGCTTCTACCCTTCCGATATCGCCGTGGAGTGGGAGTCCAACGGCCAGCCTGAGAACAACTACAAGACCACCCCTCCTGTGCTGGACTCCGAC
GGCTCCTTCTTCCTGTACTCCAAGCTGACCGTGGACAAGTCCCGGTGGCAGCAGGGCAACGTGTTCTCCTGCTCCGTGATGCACGAGGCCCTGCACAACCAC
TACACCCAGAAGTCCCTGTCCCTGAGCCCTGGCAAGTGA
```
> Antibody B: LV + LC aa (SEQ ID NO: 42)
```
QSALTQPRSVSGSPGQSVTISCTGTSSDVGGYNYVSWYQQHPGKAPKLMIYDVSKRPSGVPDRFSGSKSGNTASLTISGLQAEDEADYYCCSYAGSYTLVFG
GGTKLTVLGQPKAAPSVTLFPPSSEELQANKATLVCLISDFYPGAVTVAMKADSSPVKAGVETTTPSKQSNNKYAASSYLSLTPEQWKSHRSYSCQVTHEGS
TVEKTVAPTECSss
```
> Antibody B: HV + HC aa (SEQ ID NO: 43)
```
EVQLLESGGGLVQPGGSLRLSCAASGFTFSTYQMVWVRQAPGKGLEWVSVIYPSGGPTVYADSVKGRFTISRDNSKNTLYLQMNSLRAEDTAVYYCARGEYD
YDSSGPGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQT
YICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGKs
```

REFERENCES

The contents of all cited references including literature references, issued patents, published or non-published patent applications cited throughout this application are hereby expressly incorporated by reference in their entireties. In case of conflict, the present application, including any definitions herein, will control.

EQUIVALENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating osteotropic cancer arising from metastatic prostate cancer in a subject, the method comprising administering to said subject an effective amount of an antibody that specifically binds to a MMP-14 polypeptide comprising SEQ ID NO: 1, wherein the antibody inhibits the activity of MMP-14 and comprises a heavy chain immunoglobulin variable domain sequence and a light chain immunoglobulin variable domain, wherein the heavy chain immunoglobulin variable domain sequence comprises the heavy chain CDR1, CDR2 and CDR3 of SEQ ID NO:22 and the light chain immunoglobulin variable domain sequence comprises the CDR1, CDR2 and CDR3 of SEQ ID NO: 23, thereby treating the osteotropic cancer in the subject.

2. The method of claim 1, further comprising administering an additional therapeutic to said subject.

3. The method of claim 2, wherein the additional therapeutic is selected from the group consisting of: a bisphosphonate a hormone-related compound, a RANKL antagonist, a $\alpha_v\beta3$ antagonist, a Src inhibitor, a cathepsin K inhibitor and calcitonin.

4. A method for reducing the development of osteolytic lesions arising from metastatic prostate cancer in a subject, the method comprising administering to said subject an effective amount of an antibody that specifically binds to a MMP-14 polypeptide comprising SEQ ID NO: 1, wherein the antibody inhibits the activity of MMP-14 and comprises a heavy chain immunoglobulin variable domain sequence and a light chain immunoglobulin variable domain sequence, wherein the heavy chain immunoglobulin variable domain sequence comprises the heavy chain CDR1, CDR2 and CDR3 of SEQ ID NO:22 and the light chain immunoglobulin variable domain sequence comprises the CDR1, CDR2 and CDR3 of SEQ ID NO:23, thereby reducing the development of said osteolytic lesions in the subject.

5. The method of claim 4, further comprising administering an additional therapeutic to said subject.

6. The method of claim 5, wherein the additional therapeutic is selected from the group consisting of: a bisphosphonate a hormone-related compound, a RANKL antagonist, a $\alpha_v\beta3$ antagonist, a Src inhibitor, a cathepsin K inhibitor and calcitonin.

7. The method of claim 1 or claim 4, wherein the antibody is an antibody fragment selected from the group consisting of a Fab fragment, an soluble Fab (sFab) fragment, an F(ab')2 fragment, an Fd fragment, and an Fv fragment.

8. The method of claim 1 or 4, wherein the prostate cancer is androgen-independent prostate cancer.

9. The method of claim 1 or claim 4, wherein the antibody comprises the heavy chain variable region comprising SEQ ID NO:22.

10. The method of claim 1 or claim 4, wherein the antibody comprises the light chain variable region comprising SEQ ID NO:23.

11. The method of claim 1 or claim 4, wherein the antibody comprises the heavy chain variable region comprising SEQ ID NO:22 and the light chain variable region comprising SEQ ID NO:23.

12. The method of claim 1 or claim 4, wherein the antibody is an IgG-1 antibody.

13. The method of claim 1 or claim 4, wherein the antibody is a humanized antibody or a deimmunized antibody.

14. The method of claim 1 or 4, wherein the antibody is PEGylated.

15. The method of claim 1 or claim 4, wherein the antibody is a primate antibody or a chimeric antibody comprising a primate Fc domain.

16. The method of claim 1 or 4, wherein the antibody is a scFv.

* * * * *

SEQUENCE LISTING

<160> NUMBER OF SEQ ID NOS: 449

<210> SEQ ID NO 1
<211> LENGTH: 582
<212> TYPE: PRT
<213> ORGANISM: Homo sapiens

<400> SEQUENCE: 1

```
Met Ser Pro Ala Pro Arg Pro Pro Arg Cys Leu Leu Leu Pro Leu Leu
 1               5                  10                  15

Thr Leu Gly Thr Ala Leu Ala Ser Leu Gly Ser Ala Gln Ser Ser Ser
             20                  25                  30

Phe Ser Pro Glu Ala Trp Leu Gln Gln Tyr Gly Tyr Leu Pro Pro Gly
         35                  40                  45

Asp Leu Arg Thr His Thr Gln Arg Ser Pro Gln Ser Leu Ser Ala Ala
     50                  55                  60

Ile Ala Ala Met Gln Lys Phe Tyr Gly Leu Gln Val Thr Gly Lys Ala
 65                  70                  75                  80

Asp Ala Asp Thr Met Lys Ala Met Arg Arg Pro Arg Cys Gly Val Pro
                 85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415
```

```
Ala Ala Leu Phe Trp Met Pro Asn Gly Lys Thr Tyr Phe Arg Gly
            420                 425                 430

Asn Lys Tyr Tyr Arg Phe Asn Glu Glu Leu Arg Ala Val Asp Ser Glu
            435                 440                 445

Tyr Pro Lys Asn Ile Lys Val Trp Glu Gly Ile Glu Ser Pro Arg
450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
            485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Ile Glu
            515                 520                 525

Val Asp Glu Glu Gly Gly Gly Ala Val Ser Ala Ala Val Val Leu
            530                 535                 540

Pro Val Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
            565                 570                 575

Ser Leu Leu Asp Lys Val
            580

<210> SEQ ID NO 2
<211> LENGTH: 582
<212> TYPE: PRT
<213> ORGANISM: Mus musculus

<400> SEQUENCE: 2

Met Ser Pro Ala Pro Arg Pro Ser Arg Ser Leu Leu Pro Leu Leu
1               5                   10                  15

Thr Leu Gly Thr Ala Leu Ala Ser Leu Gly Trp Ala Gln Gly Ser Asn
            20                  25                  30

Phe Ser Pro Glu Ala Trp Leu Gln Gln Tyr Gly Tyr Leu Pro Pro Gly
            35                  40                  45

Asp Leu Arg Thr His Thr Gln Arg Ser Pro Gln Ser Leu Ser Ala Ala
50                  55                  60

Ile Ala Ala Met Gln Lys Phe Tyr Gly Leu Gln Val Thr Gly Lys Ala
65                  70                  75                  80

Asp Leu Ala Thr Met Met Ala Met Arg Arg Pro Arg Cys Gly Val Pro
            85                  90                  95

Asp Lys Phe Gly Thr Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
            115                 120                 125

Gln Asn Tyr Thr Pro Lys Val Gly Glu Tyr Ala Thr Phe Glu Ala Ile
            130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
            165                 170                 175

Ile Met Ile Leu Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
            195                 200                 205
```

```
Ile Gly Gly Asp Thr His Phe Asp Ser Ala Glu Pro Trp Thr Val Gln
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Asn Asp Pro Ser Ala Ile
                245                 250                 255

Met Ser Pro Phe Tyr Gln Trp Met Asp Thr Glu Asn Phe Val Leu Pro
            260                 265                 270

Asp Asp Asp Arg Arg Gly Ile Gln Gln Leu Tyr Gly Ser Lys Ser Gly
        275                 280                 285

Ser Pro Thr Lys Met Pro Pro Gln Pro Arg Thr Thr Ser Arg Pro Ser
    290                 295                 300

Val Pro Asp Lys Pro Lys Asn Pro Ala Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Phe Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Arg
            500                 505                 510

Arg Pro Asp Glu Gly Thr Glu Glu Thr Glu Val Ile Ile Ile Glu
        515                 520                 525

Val Asp Glu Glu Gly Ser Gly Ala Val Ser Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Lys Arg Leu Leu Tyr Cys Gln Arg
                565                 570                 575

Ser Leu Leu Asp Lys Val
            580

<210> SEQ ID NO 3
<211> LENGTH: 148
<212> TYPE: PRT
<213> ORGANISM: Homo sapiens

<400> SEQUENCE: 3
```

```
Met Ala Arg Lys Gly Ala Arg Arg Pro Arg Gln Gly Pro Gly Ser His
1               5                   10                  15

Lys Trp Leu Gln Pro Gly Ser Arg Arg Glu Lys Glu Arg Ile Pro Gln
            20                  25                  30

Pro Pro Pro Pro Ala Arg Pro Pro Arg Asp Ala Ala Pro Arg Arg Val
                35                  40                  45

Leu Val Pro Ala Val Arg Val Pro Glu Ser Gly His Phe Ala Gly
    50                  55                  60

Arg Pro Trp Ala Pro Gln Cys His Pro Lys Gly Leu Arg Arg Pro Ser
65                  70                  75                  80

Ala Glu Ser His Ser Val Ala Gln Ala Gly Val Gln Cys His Asp Leu
                85                  90                  95

Gly Ser Leu Gln Pro Pro Pro Ser Ser Gly Asp Ser Pro Ala Ser
                100                 105                 110

Ala Ser Arg Val Ala Gly Ile Thr Ser Thr Val Pro Gly Thr Leu Ser
            115                 120                 125

Ala Leu Asp Asp Cys Cys Leu Ile Thr Glu Leu Pro Tyr Lys Pro Pro
            130                 135                 140

Ala Val Leu Tyr
145
```

<210> SEQ ID NO 4
<211> LENGTH: 1955
<212> TYPE: DNA
<213> ORGANISM: Homo sapiens

<400> SEQUENCE: 4

| | | | | |
|---|---|---|---|---|
| acactttgcg | ttccgcggcc | ccggcccctt | ggtttcctag | tcctggctcc | attccctct | 60 |
| caggcctagg | gctgggaccc | ctccccgccc | ccggtcttgg | ccctgccccc | ttcaacagac | 120 |
| ggtccgcccc | ggcccctccc | cctcgtcccg | cccggccctg | gcaggccccg | cccccctgcgg | 180 |
| cctctacctt | tgacgtcttc | ccccgggagg | tggcggggggt | ctgcgaccga | atgccggcgg | 240 |
| gactctgggt | cagggcttct | ggcgggccct | gcgggggca | gcgaggtgac | cgtgaacctg | 300 |
| cggctcatgg | cgcggaaagg | agccaggcgg | ccgcggcaag | gtccgggatc | gcacaagtgg | 360 |
| ctgcaaccag | gctctaggag | ggagaaagag | cggatccccc | aaccccctcc | gcccgcccgc | 420 |
| cccccgcgag | acgcggcgcc | gcgcagggtc | ctagtgcccg | ctgtgcgaag | ggttcctgaa | 480 |
| tctggccact | tcgctgggag | gccctgggct | cccagtgcc | acccgaaggg | cctgaggagg | 540 |
| ccatctgcag | aatctcactc | tgtcgcccag | gccggagtgc | agtgtcatga | tcttggctca | 600 |
| ctgcaacctc | cgcctcccag | ttcaggagat | tctcctgcct | cagcctcccg | ggtggctggg | 660 |
| attacaagca | cagtgcctgg | cacattatcg | gcacttgatg | actgttgtct | aataactgag | 720 |
| cttccataca | aaccacctgc | cgtcctgtac | tgaaggagaa | agagcttcca | gccggggagg | 780 |
| caggaaatct | gggtcctggt | cttggttgca | tccctgactt | cctaaatgac | ctggagaagg | 840 |
| cctctgcctc | tgctgggatc | ttgtctgtgc | tggggcattt | gtttccattt | ccaagggctt | 900 |
| tttcttcctc | gctcagaatt | tgaccactca | ctaagaggag | cttagtgtgg | tgtctcacga | 960 |
| agggatcctc | ctcagccctc | acctcggtac | tggaagacgt | cgtgcgtgtc | caaaggcacc | 1020 |
| ccggggaaca | tccggtccac | ctcgctgcg | ctccgggat | ccaccatctg | cgccttcacg | 1080 |
| tcgaacctgc | gggcaggcgc | ggaggagaca | ggtgctgagc | cggctagcgg | acggaccgac | 1140 |
| ggcgcccggg | ctcccctgc | cggcggccgc | ggcggcgctc | acctccagag | cgccgcccg | 1200 |
| ctgaacagca | gcatcttccc | cctgccactc | cggagggccc | cggtcacctg | ggccacgtcg | 1260 |

```
gcgcccaggc ccagcttgtc cagacgcctc gggcccagca ccgacgcgcc tgtgtacacc    1320
cacacctggc gccctgcagg ggaggagggt cacgtcggtt tggggggcgca gagggagcac    1380 gtactcctag aacgcgagga gggagattcc ggcgaggcct ttcctagccc gcgtgcccgc    1440
agtccctgca acccaggggc agaggcgctg ggtagagcga cgcgagggcg tggagaggag    1500
ggggcagaaa ctcagccgcc cctacgtttg ctaaactgcg tccgccaggg ggcgtatttt    1560
tctaaaacgc acaagacgtt tcgtgggtta tcgatggtct cttgagcctc cttgactgat    1620
ggggattgac cgggcggggg agggaaagta ggtaactaac cagagaagaa gaaaagcttc    1680
ttggagagcg gctcctcaaa gaccgagtcc agcttgcggg gcagcgcggg ccacttgtcg    1740
gcgataagga agggggccctg cggccggctc ccctgccct cagagaatcg ccagtacttc    1800
ctgagaaagc gaggagggaa aggacgggct ctaagccttg gacacaggc cagtgggcgg    1860 gaagggacgg gcagcccctc cgcaaagccc cctcccgcat ccacacaacc ccgcctcctc    1920
acccatcctt gaacaaatac agctggttcc caatc                                1955
```

<210> SEQ ID NO 5
<211> LENGTH: 730
<212> TYPE: PRT
<213> ORGANISM: Mus musculus

<400> SEQUENCE: 5

```
Met Ser Pro Trp Gln Pro Leu Leu Leu Ala Leu Leu Ala Phe Gly Cys
1               5                   10                  15

Ser Ser Ala Ala Pro Tyr Gln Arg Gln Pro Thr Phe Val Val Phe Pro
            20                  25                  30

Lys Asp Leu Lys Thr Ser Asn Leu Thr Asp Thr Gln Leu Ala Glu Ala
        35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Gln Thr Leu Lys Ala Ile Arg
                85                  90                  95

Thr Pro Arg Cys Gly Val Pro Asp Val Gly Arg Phe Gln Thr Phe Lys
            100                 105                 110

Gly Leu Lys Trp Asp His His Asn Ile Thr Tyr Trp Ile Gln Asn Tyr
        115                 120                 125

Ser Glu Asp Leu Pro Arg Asp Met Ile Asp Asp Ala Phe Ala Arg Ala
    130                 135                 140

Phe Ala Val Trp Gly Glu Val Ala Pro Leu Thr Phe Thr Arg Val Tyr
145                 150                 155                 160

Gly Pro Glu Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Ala Gly Val Gln Gly Asp Ala His Phe Asp Asp Asp Glu
        195                 200                 205

Leu Trp Ser Leu Gly Lys Gly Val Val Ile Pro Thr Tyr Tyr Gly Asn
    210                 215                 220

Ser Asn Gly Ala Pro Cys His Phe Pro Phe Thr Phe Glu Gly Arg Ser
225                 230                 235                 240

Tyr Ser Ala Cys Thr Thr Asp Gly Arg Asn Asp Gly Thr Pro Trp Cys
                245                 250                 255
```

```
Ser Thr Thr Ala Asp Tyr Asp Lys Asp Gly Lys Phe Gly Phe Cys Pro
            260                 265                 270

Ser Glu Arg Leu Tyr Thr Glu His Gly Asn Gly Glu Gly Lys Pro Cys
        275                 280                 285

Val Phe Pro Phe Ile Phe Glu Gly Arg Ser Tyr Ser Ala Cys Thr Thr
    290                 295                 300

Lys Gly Arg Ser Asp Gly Tyr Arg Trp Cys Ala Thr Thr Ala Asn Tyr
305                 310                 315                 320

Asp Gln Asp Lys Leu Tyr Gly Phe Cys Pro Thr Arg Val Asp Ala Thr
                325                 330                 335

Val Val Gly Gly Asn Ser Ala Gly Glu Leu Cys Val Phe Pro Phe Val
            340                 345                 350

Phe Leu Gly Lys Gln Tyr Ser Ser Cys Thr Ser Asp Gly Arg Arg Asp
        355                 360                 365

Gly Arg Leu Trp Cys Ala Thr Thr Ser Asn Phe Asp Thr Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Leu Tyr Ser Tyr Leu Glu Gly Phe Pro Leu Asn
            420                 425                 430

Lys Asp Asp Ile Asp Gly Ile Gln Tyr Leu Tyr Gly Arg Gly Ser Lys
        435                 440                 445

Pro Asp Pro Arg Pro Pro Ala Thr Thr Thr Thr Glu Pro Gln Pro Thr
    450                 455                 460

Ala Pro Pro Thr Met Cys Pro Thr Ile Pro Pro Thr Ala Tyr Pro Thr
465                 470                 475                 480

Val Gly Pro Thr Val Gly Pro Thr Gly Ala Pro Ser Pro Gly Pro Thr
                485                 490                 495

Ser Ser Pro Ser Pro Gly Pro Thr Gly Ala Pro Ser Pro Gly Pro Thr
            500                 505                 510

Ala Pro Pro Thr Ala Gly Ser Ser Glu Ala Ser Thr Glu Ser Leu Ser
        515                 520                 525

Pro Ala Asp Asn Pro Cys Asn Val Asp Val Phe Asp Ala Ile Ala Glu
    530                 535                 540

Ile Gln Gly Ala Leu His Phe Phe Lys Asp Gly Trp Tyr Trp Lys Phe
545                 550                 555                 560

Leu Asn His Arg Gly Ser Pro Leu Gln Gly Pro Phe Leu Thr Ala Arg
                565                 570                 575

Thr Trp Pro Ala Leu Pro Ala Thr Leu Asp Ser Ala Phe Glu Asp Pro
            580                 585                 590

Gln Thr Lys Arg Val Phe Phe Phe Ser Gly Arg Gln Met Trp Val Tyr
        595                 600                 605

Thr Gly Lys Thr Val Leu Gly Pro Arg Ser Leu Asp Lys Leu Gly Leu
    610                 615                 620

Gly Pro Glu Val Thr His Val Ser Gly Leu Leu Pro Arg Arg Leu Gly
625                 630                 635                 640

Lys Ala Leu Leu Phe Ser Lys Gly Arg Val Trp Arg Phe Asp Leu Lys
                645                 650                 655

Ser Gln Lys Val Asp Pro Gln Ser Val Ile Arg Val Asp Lys Glu Phe
            660                 665                 670

Ser Gly Val Pro Trp Asn Ser His Asp Ile Phe Gln Tyr Gln Asp Lys
```

|  |  |  |
|---|---|---|
| Ala Tyr Phe Cys His Gly Lys Phe Phe Trp Arg Val Ser Phe Gln Asn | | |
| 690 | 695 | 700 |
| Glu Val Asn Lys Val Asp His Glu Val Asn Gln Val Asp Asp Val Gly | | |
| 705 | 710 | 715 | 720 |
| Tyr Val Thr Tyr Asp Leu Leu Gln Cys Pro | | |
| 725 | 730 | |

<210> SEQ ID NO 6
<211> LENGTH: 3185
<212> TYPE: DNA
<213> ORGANISM: Mus musculus

<400> SEQUENCE: 6

| | |
|---|---|
| ctcaccatga gtccctggca gccctgctc ctggctctcc tggctttcgg ctgcagctct | 60 |
| gctgccctt accagcgcca gccgactttt gtggtcttcc ccaaagacct gaaaacctcc | 120 |
| aacctcacgg acacccagct ggcagaggca tacttgtacc gctatggtta cacccggcc | 180 |
| gcccagatga tgggagagaa gcagtctcta cggccggctt tgctgatgct tcagaagcag | 240 |
| ctctccctgc cccagactgg tgagctggac agccagacac taaaggccat tcgaacacca | 300 |
| cgctgtggtg tcccagacgt gggtcgattc caaaccttca aaggcctcaa gtgggaccat | 360 |
| cataacatca catactggat ccaaaactac tctgaagact gccgcgaga catgatcgat | 420 |
| gacgccttcg cgcgcgcctt cgcggtgtgg ggcgaggtgg caccctcac cttcacccgc | 480 |
| gtgtacggac ccaagcgga cattgtcatc cagtttggtg tcgcggagca cggagacggg | 540 |
| tatcccttcg acggcaagga cggccttctg gcacacgcct ttccccctgg cgccggcgtt | 600 |
| cagggagatg cccatttcga cgacgacgag ttgtggtcgc tgggcaaagg cgtcgtgatc | 660 |
| cccacttact atggaaactc aaatggtgcc ccatgtcact ttcccttcac cttcgaggga | 720 |
| cgctcctatt cggcctgcac cacagacggc cgcaacgacg gcacgccttg tgtagcaca | 780 |
| acagctgact acgataagga cggcaaattt ggtttctgcc ctagtgagag actctacacg | 840 |
| gagcacggca acgagaagg caaaccctgt gtgttcccgt tcatctttga gggccgctcc | 900 |
| tactctgcct gcaccactaa aggccgctcg gatggttacc gctggtgcgc caccacagcc | 960 |
| aactatgacc aggataaact gtatggcttc tgcctaccc gagtggacgc gaccgtagtt | 1020 |
| gggggcaact cggcaggaga gctgtgcgtc ttcccccttcg tcttcctggg caagcagtac | 1080 |
| tcttcctgta ccagcgacgg ccgcagggat gggcgcctct ggtgtgcgac acatcgaac | 1140 |
| ttcgacactg acaagaagtg gggtttctgt ccagaccaag ggtacagcct gttcctggtg | 1200 |
| gcagcgcacg agttcggcca tgcactgggc ttagatcatt ccagcgtgcc ggaagcgctc | 1260 |
| atgtacccgc tgtatagcta cctcgagggc ttccctctga ataaagacga catagacggc | 1320 |
| atccagtatc tgtatggtcg tggctctaag cctgacccaa ggcctccagc caccaccaca | 1380 |
| actgaaccac agccgacagc acctccact atgtgtccca ctatacctcc cacggcctat | 1440 |
| cccacagtgg gccccacggt tgccctaca ggcgcccct cacctggccc cacaagcagc | 1500 |
| ccgtcacctg gcctacagg cgccccctca cctggccta cagcgcccc tactgcgggc | 1560 |
| tcttctgagg cctctacaga gtctttgagt ccggcagaca atccttgcaa tgtggatgtt | 1620 |
| tttgatgcta ttgctgagat ccagggcgct ctgcatttct tcaaggacgg ttggtactgg | 1680 |
| aagttcctga atcatagagg aagcccatta cagggcccct tccttactgc ccgcacgtgg | 1740 |
| ccagccctgc ctgcaacgct ggactccgcc tttgaggatc gcagaccaa gagggttttc | 1800 |
| ttcttctctg gacgtcaaat gtgggtgtac acaggcaaga ccgtgctggg ccccaggagt | 1860 |

```
ctggataagt tgggtctagg cccagaggta acccacgtca gcgggcttct cccgcgtcgt    1920
ctcgggaagg ctctgctgtt cagcaagggg cgtgtctgga gattcgactt gaagtctcag    1980
aaggtggatc cccagagcgt cattcgcgtg gataaggagt tctctggtgt gccctggaac    2040
tcacacgaca tcttccagta ccaagacaaa gcctatttct gccatggcaa attcttctgg    2100
cgtgtgagtt tccaaaatga ggtgaacaag gtggaccatg aggtgaacca ggtggacgac    2160
gtgggctacg tgacctacga cctcctgcag tgcccttgaa ctagggctcc ttctttgctt    2220
caaccgtgca gtgcaagtct ctagagacca ccaccaccac caccacacac aaacccatc     2280
cgagggaaag gtgctagctg gccaggtaca gactggtgat ctcttctaga gactgggaag    2340
gagtggaggc aggcagggct ctctctgccc accgtccttt cttgttggac tgtttctaat    2400
aaacacggat ccccaacctt ttccagctac tttagtcaat cagcttatct gtagttgcag    2460
atgcatccga gcaagaagac aactttgtag ggtggattct gacctttat ttttgtgtgg     2520
cgtctgagaa ttgaatcagc tggcttttgt gacaggcact tcaccggcta aaccacctct    2580
cccgactcca gccctttat ttattatgta tgaggttatg ttcacatgca tgtatttaac      2640
ccacagaatg cttactgtgt gtcgggcgcg gctccaaccg ctgcataaat attaaggtat    2700
tcagttgccc ctactggaag gtattatgta actatttctc tcttacattg gagaacacca    2760
ccgagctatc cactcatcaa acatttattg agagcatccc tagggagcca ggctctctac    2820
tgggcgttag ggacagaaat gttggttctt ccttcaagga ttgctcagag attctccgtg    2880
tcctgtaaat ctgctgaaac cagaccccag actcctctct ctcccgagag tccaactcac    2940
tcactgtggt tgctggcagc tgcagcatgc gtatacagca tgtgtgctag agaggtagag    3000
ggggtctgtg cgttatggtt caggtcgac tgtgtcctcc aggtgagatg accccctcagc    3060
tggaactgat ccaggaagga taaccaagtg tcttcctggc agtcttttt aaataaatga      3120
ataaatgaat atttacttaa aaaaaaaaaa aaaaaaaaaa aaaaaaaaaa aaaaaaaaaa    3180
aaaaa                                                                3185
```

<210> SEQ ID NO 7
<211> LENGTH: 730
<212> TYPE: PRT
<213> ORGANISM: Mus musculus

<400> SEQUENCE: 7

```
Met Ser Pro Trp Gln Pro Leu Leu Ala Leu Leu Ala Phe Gly Cys
1               5                   10                  15

Ser Ser Ala Ala Pro Tyr Gln Arg Gln Pro Thr Phe Val Val Phe Pro
                20                  25                  30

Lys Asp Leu Lys Thr Ser Asn Leu Thr Asp Thr Gln Leu Ala Glu Ala
            35                  40                  45

Tyr Leu Tyr Arg Tyr Gly Tyr Thr Arg Ala Ala Gln Met Met Gly Glu
        50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Gln Thr Leu Lys Ala Ile Arg
                85                  90                  95

Thr Pro Arg Cys Gly Val Pro Asp Val Gly Arg Phe Gln Thr Phe Lys
            100                 105                 110

Gly Leu Lys Trp Asp His His Asn Ile Thr Tyr Trp Ile Gln Asn Tyr
        115                 120                 125

Ser Glu Asp Leu Pro Arg Asp Met Ile Asp Asp Ala Phe Ala Arg Ala
```

```
                130              135              140
Phe Ala Val Trp Gly Glu Val Ala Pro Leu Thr Phe Thr Arg Val Tyr
145              150              155              160
Gly Pro Glu Ala Asp Ile Val Ile Gln Phe Gly Val Ala Glu His Gly
                 165              170              175
Asp Gly Tyr Pro Phe Asp Gly Lys Asp Gly Leu Leu Ala His Ala Phe
            180              185              190
Pro Pro Gly Ala Gly Val Gln Gly Asp Ala His Phe Asp Asp Asp Glu
        195              200              205
Leu Trp Ser Leu Gly Lys Gly Val Val Ile Pro Thr Tyr Tyr Gly Asn
210              215              220
Ser Asn Gly Ala Pro Cys His Phe Pro Phe Thr Phe Glu Gly Arg Ser
225              230              235              240
Tyr Ser Ala Cys Thr Thr Asp Gly Arg Asn Asp Gly Thr Pro Trp Cys
                 245              250              255
Ser Thr Thr Ala Asp Tyr Asp Lys Asp Gly Lys Phe Gly Phe Cys Pro
            260              265              270
Ser Glu Arg Leu Tyr Thr Glu His Gly Asn Gly Glu Gly Lys Pro Cys
        275              280              285
Val Phe Pro Phe Ile Phe Glu Gly Arg Ser Tyr Ser Ala Cys Thr Thr
290              295              300
Lys Gly Arg Ser Asp Gly Tyr Arg Trp Cys Ala Thr Thr Ala Asn Tyr
305              310              315              320
Asp Gln Asp Lys Leu Tyr Gly Phe Cys Pro Thr Arg Val Asp Ala Thr
                 325              330              335
Val Val Gly Gly Asn Ser Ala Gly Glu Leu Cys Val Phe Pro Phe Val
            340              345              350
Phe Leu Gly Lys Gln Tyr Ser Ser Cys Thr Ser Asp Gly Arg Arg Asp
        355              360              365
Gly Arg Leu Trp Cys Ala Thr Thr Ser Asn Phe Asp Thr Asp Lys Lys
370              375              380
Trp Gly Phe Cys Pro Asp Gln Gly Tyr Ser Leu Phe Leu Val Ala Ala
385              390              395              400
His Glu Phe Gly His Ala Leu Gly Leu Asp His Ser Ser Val Pro Glu
                 405              410              415
Ala Leu Met Tyr Pro Leu Tyr Ser Tyr Leu Glu Gly Phe Pro Leu Asn
            420              425              430
Lys Asp Asp Ile Asp Gly Ile Gln Tyr Leu Tyr Gly Arg Gly Ser Lys
        435              440              445
Pro Asp Pro Arg Pro Pro Ala Thr Thr Thr Thr Glu Pro Gln Pro Thr
450              455              460
Ala Pro Pro Thr Met Cys Pro Thr Ile Pro Pro Thr Ala Tyr Pro Thr
465              470              475              480
Val Gly Pro Thr Val Gly Pro Thr Gly Ala Pro Ser Pro Gly Pro Thr
                 485              490              495
Ser Ser Pro Ser Pro Gly Pro Thr Gly Ala Pro Ser Pro Gly Pro Thr
            500              505              510
Ala Pro Pro Thr Ala Gly Ser Ser Glu Ala Ser Thr Glu Ser Leu Ser
        515              520              525
Pro Ala Asp Asn Pro Cys Asn Val Asp Val Phe Asp Ala Ile Ala Glu
530              535              540
Ile Gln Gly Ala Leu His Phe Phe Lys Asp Gly Trp Tyr Trp Lys Phe
545              550              555              560
```

```
Leu Asn His Arg Gly Ser Pro Leu Gln Gly Pro Phe Leu Thr Ala Arg
                565                 570                 575

Thr Trp Pro Ala Leu Pro Ala Thr Leu Asp Ser Ala Phe Glu Asp Pro
            580                 585                 590

Gln Thr Lys Arg Val Phe Phe Phe Ser Gly Arg Gln Met Trp Val Tyr
        595                 600                 605

Thr Gly Lys Thr Val Leu Gly Pro Arg Ser Leu Asp Lys Leu Gly Leu
    610                 615                 620

Gly Pro Glu Val Thr His Val Ser Gly Leu Leu Pro Arg Arg Leu Gly
625                 630                 635                 640

Lys Ala Leu Leu Phe Ser Lys Gly Arg Val Trp Arg Phe Asp Leu Lys
                645                 650                 655

Ser Gln Lys Val Asp Pro Gln Ser Val Ile Arg Val Asp Lys Glu Phe
            660                 665                 670

Ser Gly Val Pro Trp Asn Ser His Asp Ile Phe Gln Tyr Gln Asp Lys
        675                 680                 685

Ala Tyr Phe Cys His Gly Lys Phe Phe Trp Arg Val Ser Phe Gln Asn
    690                 695                 700

Glu Val Asn Lys Val Asp His Glu Val Asn Gln Val Asp Asp Val Gly
705                 710                 715                 720

Tyr Val Thr Tyr Asp Leu Leu Gln Cys Pro
                725                 730

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
gacuugccgc gagacaugat t                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ucaugucucg cggcaaguct t                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
gacuucgcgg gacacaugat t                                            21
```

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
ucaugugucc cgcgaaguct t                                              21

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Phe Tyr Ser His Ser Ala Gln Ser Glu Leu Thr Gln Pro Pro Ser Ala
1               5                   10                  15

Ser Ala Ala Pro Gly Gln Arg Val Thr Ile Ser Cys Ser Gly Ser Ser
            20                  25                  30

Ser Asn Ile Gly Ser Asn Thr Val Thr Trp Tyr Gln Lys Leu Pro Gly
        35                  40                  45

Thr Ala Pro Lys Leu Leu Ile Tyr Asn Asn Tyr Glu Arg Pro Ser Gly
    50                  55                  60

Val Pro Ala Arg Phe Ser Gly Ser Lys Ser Gly Thr Ser Ala Ser Leu
65                  70                  75                  80

Ala Ile Ser Gly Leu Gln Ser Glu Asp Glu Ala Asp Tyr Tyr Cys Ala
                85                  90                  95

Thr Trp Asp Asp Ser Leu Ile Ala Asn Tyr Val Phe Gly Ser Gly Thr
            100                 105                 110

Lys Val Thr Val Leu Gly Gln Pro Lys Ala Asn Pro
        115                 120

<210> SEQ ID NO 13
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Lys Leu Leu Phe Ala Ile Pro Leu Val Val Pro Phe Val Ala
1               5                   10                  15

Gln Pro Ala Met Ala Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Pro Tyr Leu Met Asn Trp Val Arg Gln Ala Pro Gly Lys
    50                  55                  60

Gly Leu Glu Trp Val Ser Ser Ile Tyr Ser Ser Gly Gly Thr Gly
65                  70                  75                  80

Tyr Ala Asp Ser Val Lys Gly Arg Phe Thr Ile Ser Arg Asp Asn Ser
                85                  90                  95

```
Lys Asn Thr Leu Tyr Leu Gln Met Asn Ser Leu Arg Ala Glu Asp Thr
            100                 105                 110

Ala Val Tyr Tyr Cys Ala Arg Ile Tyr His Ser Ser Gly Pro Phe
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Gly Thr Ser Ser Asp Val Gly Gly Tyr Asn Tyr Val Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Ser Lys Arg Pro Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ser Tyr Ala Gly Ser Tyr Thr Leu Val
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Tyr Gln Met Val
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 18

Val Ile Tyr Pro Ser Gly Gly Pro Thr Val Tyr Ala Asp Ser Val Lys
1               5                   10                  15

Gly

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Glu Asp Tyr Tyr Asp Ser Ser Gly Pro Gly Ala Phe Asp Ile
1               5                   10                  15

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Phe Tyr Ser His Ser Ala Gln Asp Ile Gln Met Thr Gln Ser Pro Ala
1               5                   10                  15

Thr Leu Ser Leu Ser Pro Gly Glu Arg Ala Thr Leu Ser Cys Arg Ala
            20                  25                  30

Ser Gln Ser Ile Ser Ser Phe Leu Ala Trp Tyr Gln Gln Lys Pro Gly
        35                  40                  45

Gln Ala Pro Arg Leu Leu Ile Tyr Asp Ala Ser Tyr Arg Ala Thr Gly
    50                  55                  60

Ile Pro Ala Arg Phe Ser Gly Ser Gly Ser Gly Thr Asp Phe Thr Leu
65                  70                  75                  80

Thr Ile Ser Ser Leu Glu Pro Glu Asp Tyr Ala Val Tyr Tyr Cys Gln
                85                  90                  95

Gln Arg Gly Asn Trp Pro Ile Thr Phe Gly Gln Gly Thr Arg Leu Glu
            100                 105                 110

Ile Lys Arg Thr Val Ala Ala Pro Ser
        115                 120

<210> SEQ ID NO 21
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Lys Lys Leu Leu Phe Ala Ile Pro Leu Val Val Pro Phe Val Ala
1               5                   10                  15

Gln Pro Ala Met Ala Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Gln Tyr Pro Met Trp Trp Val Arg Gln Ala Pro Gly Lys
    50                  55                  60

Gly Leu Glu Trp Val Ser Tyr Ile Val Pro Ser Gly Gly Arg Thr Tyr
```

```
                65                  70                  75                  80
Tyr Ala Asp Ser Val Lys Gly Arg Phe Thr Ile Ser Arg Asp Asn Ser
                    85                  90                  95
Lys Asn Thr Leu Tyr Leu Gln Met Asn Ser Leu Arg Ala Glu Asp Thr
                    100                 105                 110
Ala Val Tyr Tyr Cys Ala Lys Asp Arg Ala Tyr Gly Asp Tyr Val Gly
                    115                 120                 125
Trp Asn Gly Phe Asp Tyr Trp Gly Gln Gly Thr Leu Val Thr Val Ser
            130                 135                 140
Ser Ala Ser Thr Lys Gly Pro Ser Val Phe Pro Leu Ala Pro Ser Ser
145                 150                 155                 160
Lys Ser

<210> SEQ ID NO 22
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Leu Tyr
            20                  25                  30
Ser Met Asn Trp Val Arg Gln Ala Pro Gly Lys Gly Leu Glu Trp Val
        35                  40                  45
Ser Ser Ile Tyr Ser Ser Gly Gly Ser Thr Leu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Arg Ala Phe Asp Ile Trp Gly Gln Gly Thr Met Val Thr
            100                 105                 110
Val Ser Ser
        115

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Val Gly Thr Tyr
            20                  25                  30
Leu Asn Trp Tyr Gln Gln Lys Pro Gly Lys Ala Pro Lys Leu Leu Ile
        35                  40                  45
Tyr Ala Thr Ser Asn Leu Arg Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Ile Pro Arg
                85                  90                  95

Phe Thr Phe Gly Pro Gly Thr Lys Val Asp Ile Lys
            100                 105
```

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Gly Met Val Trp Val Arg Gln Ala Pro Gly Lys Gly Leu Glu Trp Val
        35                  40                  45

Ser Val Ile Ser Ser Ser Gly Gly Ser Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Phe Ser Arg Arg Tyr Gly Val Phe Asp Tyr Trp Gly Gln
            100                 105                 110

Gly Thr Leu Val Thr Val Ser Ser
        115                 120
```

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Phe
            20                  25                  30

Leu Ala Trp Tyr Gln Gln Lys Pro Gly Lys Val Pro Lys Leu Leu Ile
        35                  40                  45

Tyr Gly Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Gly Val Pro Leu
                85                  90                  95

Thr Phe Gly Gly Gly Thr Lys Val Glu Ile Lys
            100                 105
```

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 26

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 29
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 31
<211> LENGTH: 330
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 31 cag tac gaa ttg act cag cct cgc tca gtg tcc ggg tct cct gga cag      48
Gln Tyr Glu Leu Thr Gln Pro Arg Ser Val Ser Gly Ser Pro Gly Gln
1               5                   10                  15 tca gtc acc atc tcc tgc act gga acc agc agt gat gtt ggt ggt tat      96
Ser Val Thr Ile Ser Cys Thr Gly Thr Ser Ser Asp Val Gly Gly Tyr
            20                  25                  30 aac tat gtc tcc tgg tac caa cag cac cca ggc aaa gcc ccc aaa ctc     144
Asn Tyr Val Ser Trp Tyr Gln Gln His Pro Gly Lys Ala Pro Lys Leu
        35                  40                  45 atg att tat gat gtc agt aag cgg ccc tca ggg gtc cct gat cgc ttc     192
Met Ile Tyr Asp Val Ser Lys Arg Pro Ser Gly Val Pro Asp Arg Phe
    50                  55                  60 tct ggc tcc aag tct ggc aac acg gcc tcc ctg acc atc tct ggg ctc     240
Ser Gly Ser Lys Ser Gly Asn Thr Ala Ser Leu Thr Ile Ser Gly Leu
65                  70                  75                  80 cag gct gag gat gag gct gat tat tac tgc tgc tca tat gca ggc agc     288
Gln Ala Glu Asp Glu Ala Asp Tyr Tyr Cys Cys Ser Tyr Ala Gly Ser
                85                  90                  95 tac act ttg gtg ttc ggc gga ggg acc aag ctg acc gtc cta             330
Tyr Thr Leu Val Phe Gly Gly Gly Thr Lys Leu Thr Val Leu
            100                 105                 110

<210> SEQ ID NO 32
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120

<210> SEQ ID NO 33
<211> LENGTH: 372
<212> TYPE: DNA
<213> ORGANISM: Artificial Sequence
<220> FEATURE:
<223> OTHER INFORMATION: Description of Artificial Sequence: Synthetic
```

```
        polynucleotide
<220> FEATURE:
<221> NAME/KEY: CDS
<222> LOCATION: (1)..(372)

<400> SEQUENCE: 33 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct act tac      96
Ser Leu Arg Leu Ser Cys Ala Ala Ser Gly Phe Thr Phe Ser Thr Tyr
            20                  25                  30 cag atg gtt tgg gtt cgc caa gct cct ggt aaa ggt ttg gag tgg gtt     144
Gln Met Val Trp Val Arg Gln Ala Pro Gly Lys Gly Leu Glu Trp Val
        35                  40                  45 tct gtt atc tat cct tct ggt ggc cct act gtt tat gct gac tcc gtt     192
Ser Val Ile Tyr Pro Ser Gly Gly Pro Thr Val Tyr Ala Asp Ser Val
    50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
65                  70                  75                  80 ttg cag atg aac agc tta agg gct gag gac acg gcc gtg tat tac tgt     288
Leu Gln Met Asn Ser Leu Arg Ala Glu Asp Thr Ala Val Tyr Tyr Cys
                85                  90                  95 gcg aga ggg gag gac tac tat gat agt agt ggc ccg ggg gct ttt gat     336
Ala Arg Gly Glu Asp Tyr Tyr Asp Ser Ser Gly Pro Gly Ala Phe Asp
            100                 105                 110 atc tgg ggc caa ggg aca atg gtc acc gtc tca agc                     372
Ile Trp Gly Gln Gly Thr Met Val Thr Val Ser Ser
        115                 120

<210> SEQ ID NO 34
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 35
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120
```

<210> SEQ ID NO 36
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 36

```
cag agc gcc ctg acc cag ccc aga agc gtg tcc ggc agc cca ggc cag      48
Gln Ser Ala Leu Thr Gln Pro Arg Ser Val Ser Gly Ser Pro Gly Gln
1               5                   10                  15 agc gtg acc atc agc tgc acc ggc acc agc agc gac gtg ggc ggc tac      96
Ser Val Thr Ile Ser Cys Thr Gly Thr Ser Ser Asp Val Gly Gly Tyr
            20                  25                  30 aac tac gtg tcc tgg tat cag cag cac ccc ggc aag gcc ccc aag ctg     144
Asn Tyr Val Ser Trp Tyr Gln Gln His Pro Gly Lys Ala Pro Lys Leu
        35                  40                  45 atg atc tac gac gtg tcc aag agg ccc agc ggc gtg ccc gac agg ttc     192
Met Ile Tyr Asp Val Ser Lys Arg Pro Ser Gly Val Pro Asp Arg Phe
    50                  55                  60 agc ggc agc aag agc ggc aac acc gcc agc ctg acc atc tcc gga ctg     240
Ser Gly Ser Lys Ser Gly Asn Thr Ala Ser Leu Thr Ile Ser Gly Leu
65                  70                  75                  80 cag gcc gag gac gag gcc gac tac tac tgc tgc agc tac gcc ggc agc     288
Gln Ala Glu Asp Glu Ala Asp Tyr Tyr Cys Cys Ser Tyr Ala Gly Ser
                85                  90                  95 tac acc ctg gtg ttc ggc gga ggg acc aag ctg acc gtg ctg              330
Tyr Thr Leu Val Phe Gly Gly Gly Thr Lys Leu Thr Val Leu
            100                 105                 110
```

<210> SEQ ID NO 37
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ser Ala Leu Thr Gln Pro Arg Ser Val Ser Gly Ser Pro Gly Gln

```
1               5                   10                  15
Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 38
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 38 gag gtg caa ttg ctg gaa agc ggc gga gga ctg gtg cag cca ggc ggc      48
Glu Val Gln Leu Leu Glu Ser Gly Gly Gly Leu Val Gln Pro Gly Gly
1               5                   10                  15 agc ctg agg ctg tcc tgc gcc gcc agc ggc ttc acc ttc agc acc tac      96
Ser Leu Arg Leu Ser Cys Ala Ala Ser Gly Phe Thr Phe Ser Thr Tyr
            20                  25                  30 cag atg gtg tgg gtg cgc cag gcc cca ggc aag ggc ctg gaa tgg gtg     144
Gln Met Val Trp Val Arg Gln Ala Pro Gly Lys Gly Leu Glu Trp Val
            35                  40                  45 tcc gtg atc tac ccc agc ggc gga ccc acc gtg tac gcc gac agc gtg     192
Ser Val Ile Tyr Pro Ser Gly Gly Pro Thr Val Tyr Ala Asp Ser Val
            50                  55                  60 aag ggc agg ttc acc atc agc agg gac aac agc aag aac acc ctg tac     240
Lys Gly Arg Phe Thr Ile Ser Arg Asp Asn Ser Lys Asn Thr Leu Tyr
65                  70                  75                  80 ctg cag atg aac agc ctg agg gcc gag gac acc gcc gtg tac tac tgc     288
Leu Gln Met Asn Ser Leu Arg Ala Glu Asp Thr Ala Val Tyr Tyr Cys
                85                  90                  95 gcc agg ggc gag gac tac tac gac agc agc ggc cca ggc gcc ttc gac     336
Ala Arg Gly Glu Asp Tyr Tyr Asp Ser Ser Gly Pro Gly Ala Phe Asp
            100                 105                 110 atc tgg ggc cag ggc aca atg gtg acc gtg tcc agc                     372
Ile Trp Gly Gln Gly Thr Met Val Thr Val Ser Ser
            115                 120

<210> SEQ ID NO 39
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Thr Tyr
            20                  25                  30
Gln Met Val Trp Val Arg Gln Ala Pro Gly Lys Gly Leu Glu Trp Val
         35                  40                  45
Ser Val Ile Tyr Pro Ser Gly Gly Pro Thr Val Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Glu Asp Tyr Tyr Asp Ser Ser Gly Pro Gly Ala Phe Asp
            100                 105                 110
Ile Trp Gly Gln Gly Thr Met Val Thr Val Ser Ser
        115                 120
```

<210> SEQ ID NO 40
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
cagagcgccc tgacccagcc cagaagcgtg tccggcagcc aggccagag cgtgaccatc      60
agctgcaccg gcaccagcag cgacgtgggc ggctacaact acgtgtcctg gtatcagcag    120
caccccggca aggccccaa gctgatgatc tacgacgtgt ccaagaggcc cagcggcgtg    180
cccgacaggt tcagcggcag caagagcggc aacaccgcca gcctgaccat ctccggactg    240
caggccgagg acgaggccga ctactactgc tgcagctacg ccggcagcta caccctggtg    300
ttcggcggag ggaccaagct gaccgtgctg ggccagccca aggctgcccc cagcgtgacc    360
ctgttccccc ccagcagcga ggaactgcag gccaacaagg ccacactggt gtgcctgatc    420
agcgacttct acccaggcgc cgtgaccgtg gcctggaagg ccgacagcag ccccgtgaag    480
gccggcgtgg agacaaccac ccccagcaag cagagcaaca caagtacgc cgccagcagc    540
tacctgagcc tgaccccga gcagtggaag tcccacaggt cctacagctg ccaggtgacc    600
cacgagggca gcaccgtgga gaaaaccgtg gccccccacc g agtgtagctg atga          654
```

<210> SEQ ID NO 41
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gaggtgcaat gctggaaag cggcggagga ctggtgcagc caggcggcag cctgaggctg       60
tcctgcgccg ccagcggctt caccttcagc acctaccaga tggtgtgggt cgccaggcc     120
ccaggcaagg gcctggaatg ggtgtccgtg atctacccca cggcggacc caccgtgtac    180
gccgacagcg tgaagggcag gttcaccatc agcagggaca acagcaagaa cccctgtac    240
ctgcagatga acagcctgag ggccgaggac accgccgtgt actactgcgc caggggcgag   300
gactactacg acagcagcgg cccaggcgcc ttcgacatct ggggccaggg cacaatggtg   360
accgtgtcca gcgccagcac caagggcccc agcgtgttcc cgctagcacc ttcctccaag   420
tccaccctcttg gcggcaccgc cgctctgggc tgcctggtga aggactactt ccctgagcct   480
```

```
gtgaccgtga gctggaactc tggcgccctg acctccggcg tgcataccct cccctgccgtg      540 ctgcagtcct ccggcctgta ctccctgtcc tccgtggtga cagtgccttc ctcctccctg      600
ggcacccaga cctacatctg caacgtgaac cacaagcctt ccaacaccaa ggtggacaag      660
cgggtggagc ctaagtcctg cgacaagacc cacacctgcc ctccctgccc tgcccctgag      720
ctgctgggcg acccctccgt gttcctgttc cctcctaagc ctaaggacac cctgatgatc      780
tcccggaccc ctgaggtgac ctgcgtggtg gtggacgtgt cccacgagga cccagaggtg      840
aagtttaatt ggtatgtgga cggcgtggag gtccacaacg ccaagaccaa gcctcgggag      900
gaacagtaca actccaccta ccgggtggtg tccgtgctga ccgtgctgca ccaggactgg      960
ctgaacggca aggaatacaa gtgcaaagtc tccaacaagg ccctgcctgc cccatcgag      1020 aaaaccatct ccaaggccaa gggccagcct cgcgagcctc aggtgtacac cctgcctcct      1080
agccgggagg aaatgaccaa gaaccaggtg tccctgacct gtctggtgaa gggcttctac      1140
ccttccgata tcgccgtgga gtgggagtcc aacggccagc tgagaacaa ctacaagacc       1200 accoctcctg tgctggactc cgacggctcc ttcttcctgt actccaagct gaccgtggac      1260
aagtcccggt ggcagcaggg caacgtgttc tcctgctccg tgatgcacga ggccctgcac      1320
aaccactaca cccagaagtc cctgtccctg agccctggca agtga                      1365
```

<210> SEQ ID NO 42
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205
```

```
Thr Val Ala Pro Thr Glu Cys Ser Ser Ser
    210                 215
```

<210> SEQ ID NO 43
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

```
Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys Ser
            450                 455

<210> SEQ ID NO 44
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Gly Trp Val Arg Gln Ala Pro Gly Lys Gly Leu Glu Trp Val
        35                  40                  45

Ser Ser Ile Val Ser Ser Gly Gly Leu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Tyr Asp Ile Leu Thr Gly Gln Gly Ala Pro
            100                 105                 110

Phe Asp Tyr Trp Gly Gln Gly Thr Leu Val Thr Val Ser Ser
        115                 120                 125

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Tyr Tyr Leu Asp Trp Tyr Leu Gln Lys Pro Gly Gln
        35                  40                  45

Ser Pro Gln Leu Leu Ile Tyr Leu Gly Ser Tyr Arg Ala Ser Gly Val
    50                  55                  60
```

```
Pro Asp Arg Phe Ser Gly Ser Gly Ser Gly Thr Asp Phe Thr Leu Lys
 65                  70                  75                  80

Ile Ser Ser Val Glu Ala Glu Asp Val Gly Val Tyr Tyr Cys Met Gln
                 85                  90                  95

Ala Leu Gln Thr Pro Leu Thr Phe Gly Gly Gly Thr Arg Val Asp Ile
            100                 105                 110

Lys
```

```
<210> SEQ ID NO 46
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Glu Met His Trp Val Arg Gln Ala Pro Gly Lys Gly Leu Glu Trp Val
         35                  40                  45

Ser Ser Ile Tyr Ser Ser Gly Gly Trp Thr Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gln Gln Tyr Tyr Asp Phe Ser Ser Arg Tyr Tyr Gly Met
            100                 105                 110

Asp Val Trp Gly Gln Gly Thr Thr Val Thr Val Ser Ser
            115                 120                 125
```

```
<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ser Glu Leu Thr Gln Pro Pro Ser Val Ser Gly Thr Pro Gly Gln
 1               5                  10                  15

Arg Val Thr Ile Ser Cys Ser Gly Thr Ser Ala Asn Ile Gly Arg Asn
             20                  25                  30

Ala Val His Trp Tyr Gln Gln Leu Pro Gly Thr Ala Pro Lys Leu Leu
         35                  40                  45

Ile His Ser Asn Asn Arg Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Glu Asn Ser Leu
                 85                  90                  95

Asn Ala Phe Tyr Val Phe Gly Thr Gly Thr Lys Val Thr Val Leu
            100                 105                 110
```

```
<210> SEQ ID NO 48
```

<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Gly Met Val Trp Val Arg Gln Ala Pro Gly Lys Gly Leu Glu Trp Val
        35                  40                  45

Ser Val Ile Ser Ser Ser Gly Gly Ser Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Pro Phe Ser Arg Arg Tyr Gly Val Phe Asp Tyr Trp Gly Gln
            100                 105                 110

Gly Thr Leu Val Thr Val Ser Ser
        115                 120

<210> SEQ ID NO 49
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Phe Leu Ala Trp Tyr Gln Gln Lys Pro Gly Lys Val Pro Lys Leu Leu
        35                  40                  45

Val Phe Gly Ala Ser Ala Leu Gln Ser Gly Val Pro Ser Arg Phe Ser
    50                  55                  60

Gly Ser Gly Ser Gly Thr Asp Phe Thr Leu Thr Ile Ser Gly Leu Gln
65                  70                  75                  80

Pro Glu Asp Val Ala Thr Tyr Tyr Cys Gln Lys Tyr Asn Gly Val Pro
                85                  90                  95

Leu Thr Phe Gly Gly Gly Thr Lys Val Glu Ile Lys
            100                 105

<210> SEQ ID NO 50
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr

```
            20                  25                  30
Glu Met Phe Trp Val Arg Gln Ala Pro Gly Lys Gly Leu Glu Trp Val
            35                  40                  45

Ser Ser Ile Ser Pro Ser Gly Gly Gln Thr His Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Thr Asp Arg Thr Tyr Tyr Asp Phe Trp Ser Gly Tyr Gly Pro Leu
            100                 105                 110

Trp Tyr Trp Gly Gln Gly Thr Leu Val Thr Val Ser Ser
            115                 120                 125

<210> SEQ ID NO 51
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Asp Ile Gln Met Thr Gln Ser Pro Leu Ser Leu Pro Val Thr Leu
 1               5                  10                  15

Gly Glu Ser Ala Ser Val Ser Cys Arg Ser Ser Gln Ser Leu Leu His
            20                  25                  30

Glu Asn Gly His Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
 65                 70                  75                  80

Ile Ser Arg Val Glu Ala Glu Asp Val Gly Val Tyr Tyr Cys Met Gln
                85                  90                  95

Ser Leu Lys Thr Pro Pro Thr Phe Gly Pro Gly Thr Lys Val Glu Ile
            100                 105                 110

Lys

<210> SEQ ID NO 52
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Met Tyr
            20                  25                  30

Met Met Ile Trp Val Arg Gln Ala Pro Gly Lys Gly Leu Glu Trp Val
        35                  40                  45

Ser Ser Ile Tyr Pro Ser Gly Gly Asn Thr Met Tyr Ala Asp Ser Val
    50                  55                  60

Lys Gly Arg Phe Thr Ile Ser Arg Asp Asn Ser Lys Asn Thr Leu Tyr
 65                 70                  75                  80
```

```
Leu Gln Met Asn Ser Leu Arg Ala Glu Asp Thr Ala Val Tyr Tyr Cys
                85                  90                  95

Ala Thr Gly Val Leu Arg Tyr Phe Asp Trp Asp Ala Gly Ser Gly Met
            100                 105                 110

Asp Val Trp Gly Gln Gly Thr Thr Val Thr Val Ser Ser
        115                 120                 125

<210> SEQ ID NO 53
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Asp Leu Gly Trp Tyr Gln Gln Lys Pro Gly Lys Ala Pro Lys Arg Leu
        35                  40                  45

Ile Tyr Val Ala Ser Ser Leu Gln Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Trp Thr Phe Gly Gln Gly Thr Lys Val Glu Ile Lys
            100                 105

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Val Met His Trp Val Arg Gln Ala Pro Gly Lys Gly Leu Glu Trp Val
        35                  40                  45

Ser Ser Ile Ser Pro Ser Gly Gly Trp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Arg Gly Thr Gly Ala Tyr Gly Met Asp Val Trp Gly Gln Gly Thr
            100                 105                 110

Thr Val Thr Val Ser Ser
        115

<210> SEQ ID NO 55
<211> LENGTH: 109
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 55

Gln Asp Ile Gln Met Thr Gln Ser Pro Gly Thr Leu Ser Leu Ser Pro
1               5                   10                  15

Gly Asp Arg Ala Thr Leu Ser Cys Gly Ala Ser Gln Leu Val Val Ser
            20                  25                  30

Asn Tyr Ile Ala Trp Tyr Gln Gln Lys Pro Gly Gln Ala Pro Arg Leu
        35                  40                  45

Leu Met Tyr Ala Gly Ser Ile Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Ile Tyr Tyr Cys Gln Gln Arg Ser Asn Trp
                85                  90                  95

Pro Trp Thr Phe Gly Gln Gly Thr Lys Val Glu Ile Lys
            100                 105

<210> SEQ ID NO 56
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Asp Ile Gln Met Thr Gln Ser Pro Ser Ser Leu Ser Ala Phe Val
1               5                   10                  15

Gly Asp Lys Val Thr Ile Thr Cys Arg Ala Ser Gln Ser Val Gly Thr
            20                  25                  30

Tyr Leu Asn Trp Tyr Gln Gln Lys Ala Gly Lys Ala Pro Glu Leu Leu
        35                  40                  45

Ile Tyr Ala Thr Ser Asn Leu Arg Ser Gly Val Pro Ser Arg Phe Ser
    50                  55                  60

Gly Ser Gly Ser Gly Thr Asp Phe Thr Leu Thr Ile Asn Thr Leu Gln
65                  70                  75                  80

Pro Glu Asp Phe Ala Thr Tyr Tyr Cys Gln Gln Ser Tyr Ser Ile Pro
                85                  90                  95

Arg Phe Thr Phe Gly Pro Gly Thr Lys Val Asp Ile Lys
            100                 105

<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Lys Met Trp Trp Val Arg Gln Ala Pro Gly Lys Gly Leu Glu Trp Val
        35                  40                  45
```

```
Ser Gly Ile Arg Pro Ser Gly Leu Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Asp Tyr Val Gly Gly Phe Asp Tyr Trp Gly Gln Gly
            100                 105                 110

Thr Leu Val Thr Val Ser Ser
        115

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln His Tyr Gly Gly Ser
                85                  90                  95

Gln Ala Phe Gly Gly Gly Thr Lys Val Glu Ile Lys
            100                 105

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Gly Trp Val Arg Gln Ala Pro Gly Lys Gly Leu Glu Trp Val
        35                  40                  45

Ser Ser Ile Ser Ser Ser Gly Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Arg Gly Phe Asp Tyr Trp Gly Gln Gly Thr Leu
            100                 105                 110

Val Thr Val Ser Ser
```

```
<210> SEQ ID NO 60
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Asp Ile Gln Met Thr Gln Ser Pro Ala Thr Leu Ser Val Ser Pro
1               5                   10                  15

Gly Glu Arg Ala Thr Leu Ser Cys Arg Ala Ser Glu Ser Val Lys Asn
            20                  25                  30

Asn Leu Ala Trp Tyr Gln Gln Lys Pro Gly Gln Ala Pro Arg Leu Leu
        35                  40                  45

Ile Tyr Gly Val Ser Thr Arg Ala Pro Gly Ile Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Pro Val Thr Phe Gly Gln Gly Thr Arg Leu Glu Ile Lys
            100                 105

<210> SEQ ID NO 61
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Gly Met Tyr Trp Val Arg Gln Ala Pro Gly Lys Gly Leu Glu Trp Val
        35                  40                  45

Ser Ser Ile Ser Ser Ser Gly Gly Tyr Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ile Lys Tyr Tyr Asp Ile Glu Gly Glu Gly Ala Phe Asp
            100                 105                 110

Ile Trp Gly Gln Gly Thr Met Val Thr Val Ser Ser
        115                 120

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62
```

Gln Asp Ile Val Met Thr Gln Thr Pro Pro Ser Leu Pro Val Asn Pro
1               5                   10                  15

Gly Glu Pro Ala Ser Ile Ser Cys Arg Ser Ser Gln Ser Leu Leu His
                20                  25                  30

Arg Asn Gly Tyr Asn Tyr Leu Asp Trp Tyr Leu Gln Lys Pro Gly Gln
            35                  40                  45

Ser Pro Gln Leu Leu Ile His Leu Gly Ser Tyr Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Pro Leu Gln Thr Pro Phe Thr Phe Gly Pro Gly Thr Lys Val Asp Ile
            100                 105                 110

Lys

<210> SEQ ID NO 63
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30

Val Met Phe Trp Val Arg Gln Ala Pro Gly Lys Gly Leu Glu Trp Val
            35                  40                  45

Ser Arg Ile Val Pro Ser Gly Gly Ala Thr Met Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Leu Tyr Asp Ser Ser Gly Tyr Val Asp Tyr Trp
            100                 105                 110

Gly Gln Gly Thr Leu Val Thr Val Ser Ser
        115                 120

<210> SEQ ID NO 64
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Asp Lys Ala Pro Lys Leu
            35                  40                  45

Ile Ile Tyr Asn Val Asn Glu Arg Pro Ser Gly Val Pro Asp Arg Phe
        50                  55                  60

```
Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Thr Ser Tyr Ala Gly Ser
                 85                  90                  95

Asn Lys Ile Gly Val Ser Gly Thr Gly Thr Lys Val Thr Val Leu
            100                 105                 110

<210> SEQ ID NO 65
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Phe Trp Val Arg Gln Ala Pro Gly Lys Gly Leu Glu Trp Val
        35                  40                  45

Ser Gly Ile Tyr Ser Ser Gly Gly Pro Thr Asp Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Asp Thr Leu Gly Arg Tyr Tyr Asp Phe Trp Ser Gly Tyr Ser
            100                 105                 110

Tyr Gly Met Asp Val Trp Gly Gln Gly Thr Thr Val Thr Val Ser Ser
        115                 120                 125

<210> SEQ ID NO 66
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Arg Ala Thr Gly Ile Pro Asp Arg Phe
    50                  55                  60

Ser Gly Ser Gly Ser Gly Thr Asp Phe Thr Leu Thr Ile Ser Arg Leu
 65                 70                  75                  80

Glu Pro Glu Asp Phe Ala Val Tyr Tyr Cys Gln Ser Gly Val Thr Phe
                85                  90                  95

Gly Gly Gly Thr Lys Val Glu Ile Lys
            100                 105

<210> SEQ ID NO 67
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ala Ser Gln Ser Val Ser Ser Tyr Leu Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ala Ser Asn Arg Ala Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Arg Gly Asn Trp Pro Ile Thr
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Tyr Arg Met Ser
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Ile Gly Ser Ser Gly Gly Gln Thr Ser Tyr Ala Asp Ser Val Lys
1               5                   10                  15

Gly

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72
```

```
Glu Pro Pro Gly Tyr Tyr Phe Asp Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln Arg Ser Asn Trp Pro Ile Thr
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Tyr Gly Met Val
1               5

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Ile Arg Ser Ser Gly Gly Pro Thr Ser Tyr Ala Asp Ser Val Lys
1               5                   10                  15

Gly

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Gly Gly Gly Thr Tyr Leu Asp Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Arg Ser Asn Trp Pro Leu Thr
1               5

<210> SEQ ID NO 78
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 78

His Tyr Arg Met Tyr
1               5

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Ile Gly Ser Ser Gly Gly Met Thr Ser Tyr Ala Asp Ser Val Lys
1               5                   10                  15
Gly

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ala Ser Gln Ser Val Ser Thr Phe Leu Ala
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Tyr Ala Ser Pro Pro Arg Thr
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Tyr Tyr Met Ser
1               5

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Ser Gly Gln Thr Phe Tyr Tyr Ala Phe Asp Ile
1               5                   10
```

```
<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Thr Ser His Asn Val Ala Asn Phe Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ala Tyr Asn Arg Ala Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Arg Ala Asn Trp Pro Leu Ser
1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Tyr Pro Met Glu
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Ile Ser Ser Ser Gly Gly Trp Thr Ser Tyr Ala Asp Ser Val Lys
1               5                   10                  15

Gly

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 89

Asp Gly Leu Glu Leu Phe Gly Gly Trp Leu Glu Ser
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 90

Arg Thr Ser Gln Ser Val Ser Asp Ser Leu Ala
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 91

Gln Gln Arg Gly Ser Trp Pro Ile Thr
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 92

Asn Tyr Arg Met Met
1               5

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 93

Glu Thr Asn Trp Asn Asp Leu Gly Arg Tyr Phe Asp Tyr
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 94

Arg Ala Ser Gln Ser Ile Ser Ser Ser Phe Leu Ala
1               5                   10

<210> SEQ ID NO 95
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ala Ser Ser Arg Ala Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Thr Tyr Ser Thr Pro Leu Thr
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Tyr Ser Met Val
1               5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val Ile Ser Pro Ser Gly Gly Tyr Thr Gly Tyr Ala Asp Ser Val Lys
1               5                   10                  15

Gly

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Met Arg Val Pro Ala Ala Ile Gly Gly Trp Leu Asp Pro
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100
```

Arg Ala Ser Gln Ser Val Ser Ser Asn Leu Ala
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ala Ser Thr Arg Ala Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

His Gln Tyr Asn Asp Trp Pro Leu Thr
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Tyr Lys Met Tyr
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Gly Tyr Ser Ser Gly Pro Leu Arg Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ala Ser Glu Ser Ile Ser Arg Asn Leu Ala
1               5                   10

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 106

Met Tyr Arg Met Ser
1               5

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Ile Gly Ser Ser Gly Gly Pro Thr Ala Tyr Ala Asp Ser Val Lys
1               5                   10                  15
Gly

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Gly Asp Ala Arg Val Pro Ala Ala Ile Gly Tyr
1               5                   10

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Ser Ser Gln Asn Val Leu Leu Ser Ser Asn Ser Lys Asn Tyr Leu
1               5                   10                  15
Ala

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Ala Ser Thr Arg Glu Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Tyr Tyr Ser Ile Pro Trp Ser
1               5
```

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asn Tyr Arg Met Ser
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Ile Gly Ser Ser Gly Gly Gln Thr Met Tyr Ala Asp Ser Val Lys
1               5                   10                  15

Gly

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser His Pro Val Ser Gly Gly Val Phe Asp Phe
1               5                   10

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Ser Ser Gln Ser Ile Leu Tyr Ser Ser Asn Asn Arg Asn Tyr Leu
1               5                   10                  15

Ala

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln His Tyr Tyr Thr Ala Pro Tyr Thr
1               5

<210> SEQ ID NO 117
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 117

Gly Tyr Ser Met His
1               5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ser Ile Trp Pro Ser Gly Gly Tyr Thr Arg Tyr Ala Asp Ser Val Lys
1               5                   10                  15
Gly

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Asn Asp Ser Asp Ser Phe Ala Tyr Arg Phe
1               5                   10

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Lys Ser Ser Gln Ser Val Leu Tyr Ser Ser Asn Asn Lys Asn Tyr Leu
1               5                   10                  15
Ala

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln Tyr Tyr Ser Thr Pro Leu Thr
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

```
Glu Tyr Arg Met Thr
1               5

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Tyr Ile Gly Ser Ser Gly Gly Met Thr Thr Tyr Ala Asp Ser Val Lys
1               5                   10                  15

Gly

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Ser Gly Ser Gly Tyr Asp Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gln Ser Tyr Ser Thr Pro Leu Thr
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Tyr Arg Met His
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Thr Val Thr Thr Leu Asp Tyr
1               5

<210> SEQ ID NO 128
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 128

Gln Gln Tyr Asn Lys Trp Pro Gln Thr
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ile Tyr Arg Met His
1               5

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Ile Gly Ser Ser Gly Gly Asn Thr Ser Tyr Ala Asp Ser Val Lys
1               5                   10                  15

Gly

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Trp Val Gly Ser Ser Ala Ala Leu Asp Tyr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Ala Ser Gln Thr Ile Ser Ser Tyr Tyr Leu Ala
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ala Ser Ser Arg Ala Ala
1               5
```

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Gln Tyr Gly Val Ser Pro Pro Tyr Ser
1               5                   10

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Tyr Asn Met Val
1               5

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Val Ile Ser Pro Ser Gly Gly Trp Thr Pro Tyr Ala Asp Ser Val Lys
1               5                   10                  15

Gly

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Val Gly Gly Ser Gly Trp Leu Gly Asp Ala Phe Asp Ile
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Ala Ser Gln Ser Val Gly Ser Asp Tyr Leu Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic

```
                                      peptide

<400> SEQUENCE: 139

Ala Ala Ser Thr Arg Ala Thr
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Gln Arg Ser Ser Trp Pro Pro Thr
1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Lys Tyr Tyr Met Val
1               5

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Ile Ser Pro Ser Gly Gly Thr Tyr Tyr Ala Asp Ser Val Lys
1               5                   10                  15

Gly

<210> SEQ ID NO 143
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asn Tyr Tyr Asp Ser Ser Gly Thr Arg Gly Ala Phe Asp Ile
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Ala Ser Glu Thr Val Arg Tyr Gly Gln Val Ala
1               5                   10
```

```
<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Ala Ser Lys Arg Ala Thr
1               5

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Tyr Arg Met Asn
1               5

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Tyr Ile Gly Ser Ser Gly Gly Ala Thr Ala Tyr Ala Asp Ser Val Lys
1               5                   10                  15

Gly

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Met Arg Gly Gly His Leu Asp Ser
1               5

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Ala Ser His Ser Val Gly Gly Gly Tyr Leu Ala
1               5                   10

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 150

Asp Ala Phe Asn Arg Ala Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Gln Arg Ser Glu Trp Pro Trp Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Tyr Lys Met Ser
1               5

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Leu Thr Ala Thr Gly Tyr Phe Asp Tyr
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Ala Ser Gln Ser Ile Ser Ser His Leu Ala
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Ala Ser Asn Arg Ala Thr
1               5

<210> SEQ ID NO 156
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 156

Gln Gln Arg Ser Asn Trp Pro Pro Thr
1               5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Tyr Arg Met Gln
1               5

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Ile Gly Ser Ser Gly Gly Gln Thr Ser Tyr Ala Asp Ser Val Lys
1               5                   10                  15

Gly

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Pro Val Gly Ala Lys Tyr Tyr Gly Met Asp Val
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ala Ser Gln Ser Val Ser Ser Ser Tyr Leu Ala
1               5                   10

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asn Tyr Arg Met His
1               5
```

```
<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Ile Ser Ser Ser Gly Gly Pro Thr Ser Tyr Ala Asp Ser Val Lys
1               5                   10                  15
Gly

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Ser Tyr Arg His Asn Asn Val Phe Asp Ile
1               5                   10

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Ala Ser Ser Arg
1               5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Tyr Arg Met Phe
1               5

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Met Gly Tyr Gly Asp Ala Phe Asp Ile
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
          peptide

<400> SEQUENCE: 167

Arg Ala Ser Gln Thr Val Ser Arg Asn Tyr Leu Ala
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Ala Ser Gln Ser Val Ser Ser Asp Leu Ala
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Val Ser Thr Lys Ala Thr
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gln Gln Tyr His Asn Trp Pro Pro Leu Thr
1               5                   10

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Tyr Thr Met Glu
1               5

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Trp Ile Ser Pro Ser Gly Gly Tyr Thr Phe Tyr Ala Asp Ser Val Lys
1               5                   10                  15

Gly
```

```
<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Tyr Ser Tyr Gly Ser Ile Asp Leu
1               5

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Ser Ser Gln Ser Leu Val Ser Ser Asn Gly Asn Thr Tyr Leu Asn
1               5                   10                  15

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Tyr Lys Val Ser Asn Arg Asp Ser
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Met Gln Gly Thr His Trp Pro Tyr Thr
1               5

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Met Tyr Arg Met Met
1               5

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178
```

```
Asp Ser Val Phe Arg Gly Glu Arg Asp Ala Phe Asp Ile
1               5                   10
```

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Arg Ala Ser Gln Asn Ile Gly Lys Phe Leu Ala
1               5                   10
```

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Gly Ala Ser Thr Leu Gln Leu
1               5
```

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Gln Lys Tyr Asp Ser Ala Leu Trp Thr
1               5
```

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Gly Tyr Gly Met Trp
1               5
```

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Ser Ile Ser Pro Ser Gly Gly Trp Thr Phe Tyr Ala Asp Ser Val Lys
1               5                   10                  15

Gly
```

<210> SEQ ID NO 184
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 184

Val Lys Val Arg His Gly Gly Gly Phe Asp Tyr
1               5                   10

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Ser Ser Glu Ser Leu Leu Gln Ser Ser Gly His Thr Arg Phe Asp
1               5                   10                  15

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Leu Gly Phe Asn Arg Ala Ser
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Met His Ala Leu Glu Pro Pro Tyr Thr
1               5

<210> SEQ ID NO 188
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Tyr Tyr Gln Met Met
1               5

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Tyr Ile Ser Pro Ser Gly Gly Met Thr Leu Tyr Ala Asp Ser Val Lys
1               5                   10                  15

Gly
```

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Trp Gly Tyr Phe Asp Tyr
1               5

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Ala Ser Gln Ser Ile Asp Thr Tyr Leu Asn
1               5                   10

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Ala Ser Lys Leu Glu Asp
1               5

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Gln Ser Tyr Ser Ser Pro Gly Ile Thr
1               5                   10

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

His Tyr Asp Met Ser
1               5

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 195

Ser Ile Trp Pro Ser Gly Gly Val Thr Trp Tyr Ala Asp Ser Val Lys
1               5                   10                  15

Gly

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Gly Tyr Asn Asn Tyr Tyr Tyr Ala Leu Asp Val
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Arg Ala Ser Gln Asp Ile Arg Ser Ser Leu Ala
1               5                   10

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Ala Ser Ser Leu Gln Ser
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Gln Ala Asn Ser Phe Pro Pro Thr
1               5

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Tyr Arg Met Gln
1               5

<210> SEQ ID NO 201
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Ser Trp Arg Gly Gly Ser Gln Tyr Phe Asp Tyr
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ala Ser Gln Ser Ile Ser Ser Tyr Leu Asn
1               5                   10

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Gln Ser Tyr Ser Thr Pro Arg Thr
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

His Tyr Val Met Ser
1               5

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Ile Gly Ser Ser Gly Gly Asp Thr His Tyr Ala Asp Ser Val Lys
1               5                   10                  15

Gly

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206
```

Val Trp Ile Ser Gly Ser Tyr Leu Asp Ala Phe Asp Ile
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Ala Ser Gln Ser Thr Ser Asn Ser Leu Ser
1               5                   10

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Ala Ser Arg Leu Gln Ser
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Gln Ser Trp Arg Thr Pro Leu Thr
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Tyr Trp Met Thr
1               5

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Ile Gly Pro Ser Gly Gly Pro Thr Thr Tyr Ala Asp Ser Val Lys
1               5                   10                  15

Gly

<210> SEQ ID NO 212
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 212

His Ser Thr Thr Val Thr Thr Asn Phe Asp Tyr
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Arg Ala Ser Gln Gly Ile Arg Asn Asp Leu Asp
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Ala Ser Asn Leu Gln Ser
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Leu Gln His Asn Ser Phe Pro Leu Thr
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Ala Trp Tyr Leu Asp Ser
1               5

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ala Ser Gln Gly Ile Arg Asn Asp Leu Gly
1               5                   10
```

```
<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Gln Thr Ile Thr Phe Pro Leu Thr
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Tyr Arg Met Met
1               5

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Ile Ser Ser Ser Gly Gly Ser Thr Gly Tyr Ala Asp Ser Val Lys
1               5                   10                  15

Gly

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Thr Val Thr Arg Val Gly Ser Phe Tyr Phe Asp Leu
1               5                   10

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Gln Leu Asn Ser Tyr Pro Pro Thr
1               5

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 223

Pro Tyr Arg Met His
1               5

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Arg Ile Gly Ser Ser Gly Gly Ala Thr Ser Tyr Ala Asp Ser Val Lys
1               5                   10                  15
Gly

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Gly Ile Ala Val Ala Gly Ile Ala Phe Asp Ile
1               5                   10

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Ala Ser Gln Gly Ile Ser Ser Ala Leu Ala
1               5                   10

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Ala Ser Ser Leu Glu Ser
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Gln Phe His Thr Tyr Pro Phe Thr
1               5

<210> SEQ ID NO 229
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Thr Tyr Arg Met Val
1               5

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Tyr Ile Gly Ser Ser Gly Gly Gln Thr Ala Tyr Ala Asp Ser Val Lys
1               5                   10                  15

Gly

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

His Asn Arg Ala Ile Gly Thr Phe Asp Tyr
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Arg Ala Ser Gln Gly Val Ser Asn Tyr Leu Ala
1               5                   10

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Ala Ser Thr Leu Gln Ser
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234
```

```
Gln Lys Tyr Asn Ser Ala Pro Tyr Thr
1               5
```

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

```
Asn Tyr Ser Met Gly
1               5
```

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Gly Ile Tyr Ser Ser Gly Gly Tyr Thr Gln Tyr Ala Asp Ser Val Lys
1               5                   10                  15

Gly
```

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

```
Gly His Tyr Val Trp Asp Ser Gly Trp Tyr Ser Ala Phe Asp Ile
1               5                   10                  15
```

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Arg Ala Ser Gln Asn Ile Ala Gly Leu Leu Ala
1               5                   10
```

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

```
Lys Ala Ser Thr Leu Glu Ser
1               5
```

<210> SEQ ID NO 240
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 240

Gln Gln Tyr Ser Phe Asn Ser Gly Thr
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Lys Tyr His Met His
1               5

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Ile Ser Pro Ser Gly Gly Val Thr Ser Tyr Ala Asp Ser Val Lys
1               5                   10                  15

Gly

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Arg Ala Ser Gln Arg Ile Ser Ile Tyr Leu Asn
1               5                   10

<210> SEQ ID NO 244
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Ala Tyr Asn Leu Gln Ser
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
```

```
<400> SEQUENCE: 245

Gln Gln Ser Asp Ser Ser Pro Xaa Thr
1               5

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Arg Ala Ser Gln Ser Ile Ser Ser Asp Leu Asn
1               5                   10

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gln Gln Ser Tyr Ser Thr Pro Val Thr
1               5

<210> SEQ ID NO 248
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Tyr Arg Met Phe
1               5

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ser Ile Ser Ser Ser Gly Gly Phe Thr Asn Tyr Ala Asp Ser Val Lys
1               5                   10                  15

Gly

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Asp Gln Gly Gly Thr Val Val Val Ala Thr Ala Asp Tyr
1               5                   10

<210> SEQ ID NO 251
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Arg Ala Ser Gln Ser Ile Ser Ser Thr Ile Thr Tyr Leu Asn
1               5                   10

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Ala Ser Asn Arg Ala Thr
1               5

<210> SEQ ID NO 253
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Tyr Lys Met Trp
1               5

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ser Ile Arg Ser Ser Gly Gly Pro Ile Gly Tyr Ala Asp Ser Val Lys
1               5                   10                  15

Gly

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Thr Asn Gln Met Gly Met Asp Val
1               5

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256
```

```
Arg Ala Ser Gln Ser Ile Ser Ser Trp Leu Ala
1               5                   10
```

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

```
Lys Ala Ser Ser Leu Glu Ser
1               5
```

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

```
Gln Gln Tyr Asn Ser Tyr Pro Trp Thr
1               5
```

<210> SEQ ID NO 259
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

```
Lys Tyr Lys Met Phe
1               5
```

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

```
Ser Ile Gly Ser Ser Gly Gly Ala Thr Ser Tyr Ala Asp Ser Val Lys
1               5                   10                  15

Gly
```

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Gly Gly Phe Trp Ser Gly Tyr Tyr Gly Tyr
1               5                   10
```

<210> SEQ ID NO 262
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 262

His Tyr Pro Met Ser
1               5

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Tyr Ile Tyr Ser Ser Gly Gly Asp Thr Glu Tyr Ala Asp Ser Val Lys
1               5                   10                  15

Gly

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Tyr Gly Ser Gly Gly Trp Met Thr Tyr Gly Leu Asp Val
1               5                   10

<210> SEQ ID NO 265
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Met Tyr Tyr Met Tyr
1               5

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Ile Arg Ser Ser Gly Gly Glu Thr Gln Tyr Ala Asp Ser Val Lys
1               5                   10                  15

Gly

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267
```

```
Gly Ala Ser Ser Leu Gln Ser
1               5
```

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

```
Gln Gln Ser Tyr Ser Ile Pro Arg Thr
1               5
```

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Trp Tyr Lys Met Ala
1               5
```

<210> SEQ ID NO 270
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

```
Val Ile Tyr Pro Ser Gly Gly Pro Thr Phe Tyr Ala Asp Ser Val Lys
1               5                   10                  15

Gly
```

<210> SEQ ID NO 271
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Gly Gln Arg Gly Tyr Asn Tyr Asp Arg Ser Ser Tyr Ser Tyr His Tyr
1               5                   10                  15

Tyr Tyr Gly Met Asp Val
                20
```

<210> SEQ ID NO 272
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

```
Arg Ala Thr Gln Tyr Ile Ser Asn Tyr Val Asn
1               5                   10
```

<210> SEQ ID NO 273

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Tyr Ser Met His
1               5

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Leu Gly Ser Ser Gly Gly Pro Thr Ser Tyr Ala Asp Ser Val Lys
1               5                   10                  15

Gly

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Ser Ser Tyr Gly Arg Gly Phe Asp Tyr
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Arg Ala Ser Gln Gly Ile Ser Asn Tyr Leu Ala
1               5                   10

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Ala Ser Asn Leu Gln Ser
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278
```

```
Gln Gln Tyr Lys Thr Tyr Pro Phe Thr
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ala Arg Ala Gly Thr Phe Phe Asp Ser
1               5

<210> SEQ ID NO 280
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Arg Ala Ser Gln Gly Ile Ser Arg Trp Leu Ala
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Gln Arg Ser Asn Trp Pro Pro Arg Leu Thr
1               5                   10

<210> SEQ ID NO 282
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Phe Tyr His Met Ser
1               5

<210> SEQ ID NO 283
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Ile Gly Pro Ser Gly Gly Trp Thr Asn Tyr Ala Asp Ser Val Lys
1               5                   10                  15

Gly

<210> SEQ ID NO 284
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 284

Asp Gly Gly Leu Glu Gly Met Asp Val
1               5

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Ala Ser Gln Gly Ile Ser Ser Trp Leu Ala
1               5                   10

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gln Gln Ala Asn Ser Phe Pro Tyr Leu Thr
1               5                   10

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Thr Tyr Met Met Met
1               5

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Ile Trp Ser Ser Gly Gly Ser Thr Phe Tyr Ala Asp Ser Val Lys
1               5                   10                  15

Gly

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly Val Val Val Pro Ala Leu Asp Tyr
```

```
<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Pro Thr Tyr Ser Thr Ser Trp Thr
1               5

<210> SEQ ID NO 291
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Thr Tyr Ser Met Val
1               5

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Ile Gly Ser Ser Gly Gly Asp Thr Phe Tyr Ala Asp Ser Val Lys
1               5                   10                  15

Gly

<210> SEQ ID NO 293
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asp Arg Ala Asp Thr Val Val Thr Ala Gly Asp Tyr Tyr Tyr Tyr
1               5                   10                  15

Tyr Gly Met Asp Val
            20

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Ala Ser Ser Leu Glu Ser
1               5

<210> SEQ ID NO 295
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asp Tyr Arg Met Thr
1               5

<210> SEQ ID NO 296
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Trp Ile Gly Ser Ser Gly Gly Gln Thr Ser Tyr Ala Asp Ser Val Lys
1               5                   10                  15

Gly

<210> SEQ ID NO 297
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Thr Pro Arg Val Ala Ser Tyr Phe Asp Tyr
1               5                   10

<210> SEQ ID NO 298
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asn Tyr Lys Met His
1               5

<210> SEQ ID NO 299
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ser Ile Gly Ser Ser Gly Gly Met Thr Ser Tyr Ala Asp Ser Val Lys
1               5                   10                  15

Gly

<210> SEQ ID NO 300
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 300

Arg Asp Trp Gln His Leu Ala Gly Asp Ala Phe Asp Phe
1               5                   10

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Tyr Ala Thr Ser Ser Leu Gln Ser
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gln Gln Ser Lys Ser Phe Pro Pro Thr
1               5

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Arg Tyr Arg Met Asn
1               5

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Tyr Ile Gly Ser Ser Gly Gly Asn Thr Ala Tyr Ala Asp Ser Val Lys
1               5                   10                  15

Gly

<210> SEQ ID NO 305
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Arg Arg Ile Gly Val Gly Ala Lys Gly Gly Thr Phe Asp Ile
1               5                   10                  15

<210> SEQ ID NO 306
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Ala Ser Gln Asp Ile Gly Asn Tyr Leu Asn
1               5                   10

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asp Thr Ser Ile Leu Lys Lys
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 308

Gln Gln Ala Asn Ser Phe Xaa Leu Thr
1               5

<210> SEQ ID NO 309
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Leu Tyr Asn Met Trp
1               5

<210> SEQ ID NO 310
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Ile Ser Ser Ser Gly Gly Asn Thr Lys Tyr Ala Asp Ser Val Lys
1               5                   10                  15

Gly

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 311

Gly Ala Pro Tyr Tyr Leu Gln Leu
1               5

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Asp Val Ser Asn Arg Ala Thr
1               5

<210> SEQ ID NO 313
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Met Tyr Arg Met Ile
1               5

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Leu Trp Cys Asp Asn
1               5

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Ser Gly Asp Lys Leu Gly Asp Lys Tyr Ala Ser
1               5                   10

<210> SEQ ID NO 316
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Asp Arg Lys Arg Pro Ser
1               5

<210> SEQ ID NO 317
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Ala Trp Asp Ser Asn Thr Val Val
1               5

<210> SEQ ID NO 318
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

His Tyr Asp Met Trp
1               5

<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Arg Ile Val Pro Ser Gly Gly Leu Thr Thr Tyr Ala Asp Ser Val Lys
1               5                   10                  15

Gly

<210> SEQ ID NO 320
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

His Ser Phe Trp Ser Gly Tyr Tyr Gly Ala Phe Asp Ile
1               5                   10

<210> SEQ ID NO 321
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Thr Gly Thr Ser Ser Asp Val Gly Tyr Tyr Asn Tyr Val Ser
1               5                   10

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322
```

```
Asp Val Ser Ala Arg Pro Ser
1               5

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Cys Ser Tyr Ala Gly Ser Tyr Thr Tyr Val
1               5                   10

<210> SEQ ID NO 324
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Met Tyr Tyr Met Gln
1               5

<210> SEQ ID NO 325
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ser Ile Arg Ser Ser Gly Gly Phe Thr Ser Tyr Ala Asp Ser Val Lys
1               5                   10                  15

Gly

<210> SEQ ID NO 326
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Leu Arg Leu Asp Met
1               5

<210> SEQ ID NO 327
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Arg Tyr His Met Phe
1               5

<210> SEQ ID NO 328
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 328

Tyr Ile Ser Pro Ser Gly Gly Val Thr Met Tyr Ala Asp Ser Val Lys
1               5                   10                  15

Gly

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Ala Pro Ser Gly Thr Phe Phe Asp Tyr
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Asp Ala Ser Thr Arg Ala Thr
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

His Gln Arg Ser Asn Trp Pro Gln Thr
1               5

<210> SEQ ID NO 332
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Arg Tyr Arg Met Leu
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Arg Ala Lys Lys Gly Ala Phe Asp Ile
1               5
```

```
<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Ala Ser Gln Ser Val Thr Asn Asn Leu Ala
1               5                   10

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gln Gln Tyr Asn Asn Trp Pro Arg Thr
1               5

<210> SEQ ID NO 336
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Glu Tyr Met Met Trp
1               5

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Ile Gly Ser Ser Gly Gly Ile Thr Ser Tyr Ala Asp Ser Val Lys
1               5                   10                  15

Gly

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln His Tyr Gly Asp Tyr Asp Tyr
1               5

<210> SEQ ID NO 339
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 339

Ile Tyr Asn Met Tyr
1               5

<210> SEQ ID NO 340
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Tyr Ile Tyr Ser Ser Gly Gly Pro Thr Ala Tyr Ala Asp Ser Val Lys
1               5                   10                  15

Gly

<210> SEQ ID NO 341
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Arg Gly Tyr Tyr Asp Ser Ser Gly Tyr Trp Gly Ala Phe Asp Ile
1               5                   10                  15

<210> SEQ ID NO 342
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Gln Gln Tyr Gly Ser Ser His Thr
1               5

<210> SEQ ID NO 343
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

His Tyr Leu Met Val
1               5

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Ile Val Ser Ser Gly Gly Tyr Thr Ala Tyr Ala Asp Ser Val Lys
1               5                   10                  15

Gly

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Ala Tyr Asp Ser Ser Gly Ile Val Phe Asp Tyr
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Arg Ala Ser Gln Ser Val Ser Ile Asn Leu Ala
1               5                   10

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gln Gln Tyr Asp Asn Trp Trp Thr
1               5

<210> SEQ ID NO 348
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gln Tyr Val Met Ser
1               5

<210> SEQ ID NO 349
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ser Ile Val Pro Ser Gly Gly Tyr Thr Ser Tyr Ala Asp Ser Val Lys
1               5                   10                  15

Gly

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Ser Leu Arg Pro Gly Phe Gly Glu Leu Pro Gly Tyr
1               5                   10

<210> SEQ ID NO 351
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Arg Ser Ser Gln Ser Leu Leu His Asn Asn Gly Tyr Asn Tyr Leu Asp
1               5                   10                  15

<210> SEQ ID NO 352
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Leu Gly Ser Tyr Arg Ala Ser
1               5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Met Gln Ala Leu Gln Thr Pro Ile Thr
1               5

<210> SEQ ID NO 354
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Glu Tyr Ala Met Leu
1               5

<210> SEQ ID NO 355
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Tyr Ile Ser Pro Ser Gly Gly Ser Thr Phe Tyr Ala Asp Ser Val Lys
1               5                   10                  15
Gly

```
<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gly Gly Thr Lys Lys Ser Ile
1               5

<210> SEQ ID NO 357
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Arg Ser Ser Gln Ser Leu Leu His Arg Asn Gly Gln Asn Tyr Leu Asp
1               5                   10                  15

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Leu Gly Ser Asn Arg Ala Ser
1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Met Gln Gly Leu Gln Thr Pro Arg Thr
1               5

<210> SEQ ID NO 360
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Met Tyr Glu Met Gln
1               5

<210> SEQ ID NO 361
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361
```

```
Gly Ile Ser Pro Ser Gly Gly Lys Thr Tyr Ala Asp Ser Val Lys
1               5                   10                  15

Gly

<210> SEQ ID NO 362
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Arg Tyr Ser Gly Ser Tyr Phe Pro Pro Gly Gly Ser His Phe Asp
1               5                   10                  15

Tyr

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gln Gln Ser Tyr Ser Thr Pro Trp Thr
1               5

<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Pro Tyr Ala Met Val
1               5

<210> SEQ ID NO 365
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Trp Ile Ser Pro Ser Gly Gly Asp Thr Asp Tyr Ala Asp Ser Val Lys
1               5                   10                  15

Gly

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gly Phe Gly Trp Phe Asp Asp Ala Phe Asp Ile
1               5                   10
```

```
<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Trp Ala Ser Gln Asp Val Ser Ser Phe Phe Ala
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ser Ala Ser Thr Leu Gln Gly
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gln Gln Tyr Asn Thr Phe Pro Trp Thr
1               5

<210> SEQ ID NO 370
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Met Tyr Asn Met Ile
1               5

<210> SEQ ID NO 371
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Val Val Gly Ala Ala Gly Ile Leu Gln Pro Phe Asp Tyr
1               5                   10

<210> SEQ ID NO 372
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372
```

```
Arg Tyr Gly Met Gly
1               5

<210> SEQ ID NO 373
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Val Ile Trp Pro Ser Gly Gly Ser Thr Tyr Tyr Ala Asp Ser Val Lys
1               5                   10                  15

Gly

<210> SEQ ID NO 374
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Val Arg Asp Tyr Tyr Asp Ser Ser Gly His Tyr Phe Ser Asp Ala Phe
1               5                   10                  15

Asp Ile

<210> SEQ ID NO 375
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gln Ala Ser Gln Asp Ile Ser Asn Tyr Leu Asn
1               5                   10

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Asp Ala Ser Ser Leu Gln Ser
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Glu Gln Ala Asn Ser Phe Pro Leu Thr
1               5

<210> SEQ ID NO 378
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ser Tyr Asp Met Asn
1               5

<210> SEQ ID NO 379
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gly Ile Gly Ser Ser Gly Gly Leu Thr Glu Tyr Ala Asp Ser Ile Lys
1               5                   10                  15

Gly

<210> SEQ ID NO 380
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Asp Arg Gly Tyr Asn Asn Tyr Tyr Tyr Gly Met Asp Val
1               5                   10

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Arg Ala Ser His Gly Ala Arg Val Asp Leu Ala
1               5                   10

<210> SEQ ID NO 382
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gly Thr Ser Ser Leu Gln Arg
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383
```

```
Leu Gln His Asn Ser Tyr Pro Leu Thr
1               5
```

```
<210> SEQ ID NO 384
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Met Tyr Asp Met Ser
1               5
```

```
<210> SEQ ID NO 385
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Tyr Ile Ser Ser Ser Gly Gly Phe Thr Met Tyr Ala Asp Ser Val Lys
1               5                   10                  15
Gly
```

```
<210> SEQ ID NO 386
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Asp Leu Asn Ser Ser Ser Pro Pro Gly Ser Asn Asp Ala Phe Asp Ile
1               5                   10                  15
```

```
<210> SEQ ID NO 387
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Arg Ala Ser Gln Asp Ile Ser Asn Tyr Leu Ala
1               5                   10
```

```
<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gln Gln Ser Tyr Ser Ala Pro Phe Thr
1               5
```

```
<210> SEQ ID NO 389
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 389

Lys Tyr Leu Met Asn
1               5

<210> SEQ ID NO 390
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ser Ile Ser Pro Ser Gly Gly Met Thr Ala Tyr Ala Asp Ser Val Lys
1               5                   10                  15
Gly

<210> SEQ ID NO 391
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Met Met Lys Glu Thr Glu Tyr Asp Thr Asn Trp Tyr Phe Ala Phe Asp
1               5                   10                  15
Tyr

<210> SEQ ID NO 392
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Arg Ala Ser Gln Gly Ile Ser Thr Phe Leu Ala
1               5                   10

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Ala Ser Thr Leu Gln Ser
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394
```

-continued

```
Gln Lys Tyr Asn Ser Ala Pro Phe Thr
1               5

<210> SEQ ID NO 395
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Lys Tyr Gln Met Gln
1               5

<210> SEQ ID NO 396
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Tyr Ile Val Pro Ser Gly Gly Leu Thr Asp Tyr Ala Asp Ser Val Lys
1               5                   10                  15

Gly

<210> SEQ ID NO 397
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Gly Arg Gly Gly Tyr Thr His Phe Asp Phe
1               5                   10

<210> SEQ ID NO 398
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Arg Ala Ser Gln Ser Ile Ser Arg Tyr Leu Asn
1               5                   10

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ala Ala Ala Ser Leu Gln Ser
1               5

<210> SEQ ID NO 400
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 400

Gln Gln Ser Tyr Ser Thr Pro Pro Leu Thr
1               5                   10

<210> SEQ ID NO 401
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Tyr Gly Met Ala
1               5

<210> SEQ ID NO 402
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gly Ile Tyr Ser Ser Gly Gly Trp Thr Ala Tyr Ala Asp Ser Val Lys
1               5                   10                  15

Gly

<210> SEQ ID NO 403
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Asp Leu Ser Gly Ser Tyr Ser Asp
1               5

<210> SEQ ID NO 404
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Arg Ala Ser Gln Gly Ile Ser Asn Trp Leu Ala
1               5                   10

<210> SEQ ID NO 405
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Phe Gly Ala Ser Asn Leu Gln Ser
1               5
```

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gln Gln Ala Asp Ser Phe Pro Ile Thr
1               5

<210> SEQ ID NO 407
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

His Tyr Ser Met Val
1               5

<210> SEQ ID NO 408
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Tyr Ile Trp Pro Ser Gly Gly Thr Thr Lys Tyr Ala Asp Ser Val Lys
1               5                   10                  15

Gly

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gly Trp Phe Thr Asp Ala Phe Asp Ile
1               5

<210> SEQ ID NO 410
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Arg Ala Asn Gln Arg Ile Ser Thr Tyr Leu Ala
1               5                   10

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 411

Ala Gly Ser Thr Leu Gln Ser
1               5

<210> SEQ ID NO 412
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ser Tyr Thr Met Ser
1               5

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Ser Ile Ser Ser Ser Gly Gly Phe Thr Val Tyr Ala Asp Ser Ala Lys
1               5                   10                  15

Gly

<210> SEQ ID NO 414
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Glu Gly Gly Thr Phe Pro Val Tyr Tyr Phe Asp Asn
1               5                   10

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gln Gln Ala Asn Ser Phe Pro Leu Thr
1               5

<210> SEQ ID NO 416
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Tyr Ile Gly Pro Ser Gly Gly Tyr Thr Ala Tyr Ala Asp Ser Val Lys
1               5                   10                  15

Gly
```

<210> SEQ ID NO 417
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Asp Pro Ser Tyr Tyr Asp Ser Ser Gly Tyr Asp Ala Phe Asp Ile
1               5                   10                  15

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gln Gln Ala Asn Ser Phe Pro Ile Thr
1               5

<210> SEQ ID NO 419
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Pro Tyr Asp Met His
1               5

<210> SEQ ID NO 420
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ser Ile Gly Pro Ser Gly Gly Val Thr Phe Tyr Ala Asp Ser Val Lys
1               5                   10                  15

Gly

<210> SEQ ID NO 421
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Glu Ile Pro Gly Asp Ser Gly Tyr Asp Asp Tyr
1               5                   10

<210> SEQ ID NO 422
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 422

Arg Ala Ser Gln Gly Ile Thr Thr Trp Leu Ala
1               5                   10

<210> SEQ ID NO 423
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Ser Ala Ser Thr Leu His Ser
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gln Gln Ala Asn Asn Phe Pro Tyr Thr
1               5

<210> SEQ ID NO 425
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ala Tyr Ser Met Gly
1               5

<210> SEQ ID NO 426
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Val Ile Gly Ser Ser Gly Gly Tyr Thr Asn Tyr Ala Asp Ser Val Lys
1               5                   10                  15

Gly

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Arg Pro His Ser Thr Gly Thr Asp Ala Phe Asp Ile
1               5                   10

```
<210> SEQ ID NO 428
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Arg Ala Ser Gln Ser Ile Gly Ser Trp Leu Ala
1               5                   10

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Lys Ala Ser Ser Leu Glu Gly
1               5

<210> SEQ ID NO 430
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly Tyr Ile Met Gly
1               5

<210> SEQ ID NO 431
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ser Ile Ser Pro Ser Gly Gly Ile Thr Met Tyr Ala Asp Ser Val Lys
1               5                   10                  15

Gly

<210> SEQ ID NO 432
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Asp Asn Trp Asn Asp Gly Ala Phe Asp Ile
1               5                   10

<210> SEQ ID NO 433
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 433

Arg Ala Ser Gln Tyr Ile Arg Asn Asp Leu Gly
1               5                   10

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Leu Gln Asp Tyr Ser Tyr Pro Gln Thr
1               5

<210> SEQ ID NO 435
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Tyr Tyr Pro Met Gly
1               5

<210> SEQ ID NO 436
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Ser Ile Tyr Ser Ser Gly Gly Lys Thr Gln Tyr Ala Asp Ser Val Lys
1               5                   10                  15

Gly

<210> SEQ ID NO 437
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Arg Tyr Gly Asp Phe Asp Tyr
1               5

<210> SEQ ID NO 438
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Arg Ser Ser Gln Ser Leu Val His Ser Asp Gly Asn Thr Tyr Leu Asn
1               5                   10                  15

<210> SEQ ID NO 439
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Lys Val Ser Asn Arg Asp Ser
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Met Gln Gly Thr His Trp Pro Trp Thr
1               5

<210> SEQ ID NO 441
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Asn Tyr Thr Met Phe
1               5

<210> SEQ ID NO 442
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Val Ile Ser Pro Ser Gly Gly Asn Thr Ala Tyr Ala Asp Ser Val Lys
1               5                   10                  15

Gly

<210> SEQ ID NO 443
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Phe Ala Gly Lys Asn
1               5

<210> SEQ ID NO 444
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444
```

```
Ser Gly Ser Ser Ser Asn Ile Gly Ser Asn Thr Val Tyr
1               5                   10
```

<210> SEQ ID NO 445
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

```
Arg Asn Asn Gln Arg Pro Leu
1               5
```

<210> SEQ ID NO 446
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

```
Ala Ala Trp Asp Asp Ser Leu Ser Thr Trp Val
1               5                   10
```

<210> SEQ ID NO 447
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

```
Val Tyr Asp Met Met
1               5
```

<210> SEQ ID NO 448
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

```
Gly Ile Ser Pro Ser Gly Gly Tyr Thr Lys Tyr Ala Asp Ser Val Lys
1               5                   10                  15

Gly
```

<210> SEQ ID NO 449
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

```
His Arg Leu Arg Phe Leu Glu Asp Ala Phe Asp Ile
1               5                   10
```